(12) United States Patent
Novek

(10) Patent No.: US 11,897,840 B2
(45) Date of Patent: *Feb. 13, 2024

(54) PROCESSES FOR THE PRODUCTION OF CITRIC ACID

(71) Applicant: INNOVATOR ENERGY, LLC, Houston, TX (US)

(72) Inventor: Ethan Novek, Houston, TX (US)

(73) Assignee: INNOVATOR ENERGY. LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,483

(22) Filed: Feb. 1, 2022

(65) Prior Publication Data

US 2022/0259130 A1 Aug. 18, 2022

Related U.S. Application Data

(63) Continuation of application No. 17/243,714, filed on Apr. 29, 2021, now Pat. No. 11,236,033, which is a
(Continued)

(51) Int. Cl.
 C07C 51/02 (2006.01)
 C07C 51/47 (2006.01)
(Continued)

(52) U.S. Cl.
 CPC .............. *C07C 51/02* (2013.01); *C01F 11/02* (2013.01); *C01F 11/04* (2013.01); *C01F 11/06* (2013.01); *C07C 51/47* (2013.01)

(58) Field of Classification Search
 None
 See application file for complete search history.

(56) References Cited

U.S. PATENT DOCUMENTS 11,236,033 B2 * 2/2022 Novek ................. C01F 11/04
11,512,036 B2 * 11/2022 Novek ................. C01B 17/50
(Continued)

FOREIGN PATENT DOCUMENTS

WO 2020150449 A1 7/2020
WO 2020186178 A1 9/2020

OTHER PUBLICATIONS

Payne et al., "The Chemical and Preservative Properties of Sulfur Dioxide Solution for Brining Fruit." Agricultural Experiment Station, Oregon State University, Corvallis, Jun. 1969.*
International Search Report and Written opinion dated Jul. 27, 2022 issued in PCT/US2022/26907.

*Primary Examiner* — Daniel Berns
(74) *Attorney, Agent, or Firm* — Hunton Andrews Kurth LLP

(57) ABSTRACT

The present application pertains to methods for making metal oxides and/or citric acid. In one embodiment, the application pertains to a process for producing calcium oxide, magnesium oxide, or both from a material comprising calcium and magnesium. The process may include reacting a material comprising calcium carbonate and magnesium carbonate. Separating, concentrating, and calcining may lead to the production of oxides such as calcium oxide or magnesium oxide. In other embodiments the application pertains to methods for producing an alkaline-earth oxide and a carboxylic acid from an alkaline earth cation-carboxylic acid anion salt. Such processes may include, for example, reacting an alkaline-earth cation-carboxylic acid anion salt with aqueous sulfur dioxide to produce aqueous alkaline-earth-bisulfite and aqueous carboxylic acid solution. Other useful steps may include desorbing, separating, and/or calcining.

27 Claims, 13 Drawing Sheets

Related U.S. Application Data continuation-in-part of application No. 16/944,850, filed on Jul. 31, 2020, now Pat. No. 11,034,619.

(60) Provisional application No. 63/179,822, filed on Apr. 26, 2021, provisional application No. 63/157,847, filed on Mar. 8, 2021, provisional application No. 63/163,993, filed on Mar. 22, 2021, provisional application No. 63/147,286, filed on Feb. 9, 2021, provisional application No. 63/153,461, filed on Feb. 25, 2021, provisional application No. 62/895,557, filed on Sep. 4, 2019, provisional application No. 63/042,397, filed on Jun. 22, 2020.

(51) Int. Cl.
*C01F 11/02* (2006.01)
*C01F 11/04* (2006.01)
*C01F 11/06* (2006.01)

(56) References Cited

U.S. PATENT DOCUMENTS

| | | |
|---|---|---|
| 2011/0301072 A1 | 12/2011 | Smith et al. |
| 2016/0221834 A1 | 8/2016 | Hasinoff et al. |
| 2021/0061706 A1 | 3/2021 | Novek |

* cited by examiner

US 11,897,840 B2

PROCESSES FOR THE PRODUCTION OF CITRIC ACID

CROSS-REFERENCE TO RELATED APPLICATIONS

This application is a continuation of Ser. No. 17/243,714 filed on Apr. 29, 2021 issuing as U.S. Pat. No. 11,236,033 on Feb. 1, 2022 which application is a continuation in part of U.S. application Ser. No. 16/944,850 filed Jul. 31, 2020 which application claims priority to U.S. provisional application No. 62/895,557 filed Sep. 4, 2019 and U.S. provisional application No. 63/042,397 filed Jun. 22, 2020 and U.S. provisional application No. 62/890,254 filed Aug. 22, 2019. This Application also claims priority to U.S. Provisional Application No. 63/147,286 filed on Feb. 9, 2021. All applications are incorporated by reference in their entirety.

BACKGROUND AND SUMMARY

CaO is currently produced by heating CaCO3 or limestone to decompose it into CaO and CO2 in a process called calcining. Calcining is energy intensive and CO2 emission intensive. The process of calcining produces CO2 in the form of flue gas. A similar process is currently used in the production of cement, such as portant cement. For CO2 to be useful from calcining, the CO2 must be separated from the flue gas by a post-combustion CO2 capture system, which requires very high capital and operating costs, which generally exceed the value of said CO2. Alternatively, a calciner may be powered by fuel combusted in pure oxygen (oxy-combustion) from an air separation unit. Oxy-combustion has high capital and operating costs due to the required air separation unit and the significantly higher operating temperature required for decomposing CaCO3 in a pure environment CO2.

The present invention may react SO2 (gas or liquid or aqueous solution or non-aqueous solution or supercritical or solid or a combination thereof) with CaCO3, which may result in the formation of CaSO3 and CO2. The resulting CO2 may undergo further purification to remove, for example, at least a portion of SO2 or any other gases present from the CO2. CO2 may be sold or used for one or more applications of high pressure and/or purity CO2. CaSO3 may be thermally decomposed into CaO and SO2. The thermal decomposition of CaSO3 may involve an oxygen free or ultra-low oxygen environment. The thermal decomposition of CaSO3 may be conducted in the presence of a combustion flue gas or a carrier gas or a combination thereof. SO2 may be separated and may be recovered or regenerated for re-use internally. Advantageously, SO2 possesses a significantly greater solubility in water and/or other physical solvents than CO2, which may enable the use of physical solvents to separate SO2 and/or may enable the use of a SO2 wash solution to react SO2 with CaCO3. CaO may be sold or used for one or more applications of CaO. The process may be batch, semi-batch, semi-continuous, continuous, or a combination thereof.

The present invention may pertain to systems, methods, and processes for producing calcium oxide or magnesium oxide or lime or sodium oxide or potassium oxide other oxide salt from a carbonate salt while intrinsically generating relatively high partial pressure CO2 and/or relatively high purity CO2. The present invention may pertain to systems, methods, and processes for producing cement from a carbonate salt while intrinsically generating relatively high partial pressure CO2 and/or relatively high purity CO2. Calcium and magnesium salts may be provided as example salts, although other cations capable of forming carbonate, bicarbonate, or oxide salts or ionic compounds are applicable to the present invention. Some embodiments may involve reacting a regenerable acid or regenerable acid gas with calcium carbonate and/or magnesium carbonate to produce an intermediate comprising calcium-acid gas and/or magnesium-acid gas and an output comprising captured CO2. Said calcium-acid gas and/or magnesium-acid gas intermediate may be converted into an intermediate comprising regenerable acid gas and an output comprising calcium oxide or magnesium oxide or cement. Some embodiments may employ a regenerable acid gas which may be regenerated using, for example, including, but not limited to, heat, electricity, light, condensation, absorption, gas-forming reaction, gas-forming decomposition, electrodialysis, or a combination thereof.

The present invention may involve employing acid gases with regeneration or recovery properties which may be more desirable or advantageous than, for example, CO2. For example, sulfur dioxide (SO2) is significantly more soluble in water than CO2 at the same vapor pressure and temperature, and/or sulfurous acid (aqueous sulfur dioxide) displaces CO2 in carbonate salts to form sulfite or bisulfite or metabisulfite salts. Sulfite or bisulfite or metabisulfite salts may possess decomposition temperatures and enthalpies of decomposition similar to carbonate salts. Said more desirable or advantageous properties may include, but are not limited to, solubility in water, solubility in one or more solvents or liquids, enthalpy of desorption, enthalpy of absorption, enthalpy of reaction, or a combination thereof. Some embodiments may involve systems and methods for preventing oxidation or degradation or contamination of the acid gas, or preventing oxidation or degradation or contamination of the calcium oxide, or preventing degradation or contamination of the carbon dioxide, or preventing degradation or contamination of a physical solvent or a combination thereof.

The present invention also may comprise a process for producing calcium oxide and/or magnesium oxide from a material comprising calcium and/or magnesium. The present invention may comprise a process for calcium oxide and/or magnesium oxide and/or captured carbon dioxide from a material comprising calcium carbonate and/or magnesium carbonate. The present invention may include processes for separating at least a portion of magnesium from a material comprising calcium and magnesium. The present invention may include processes for separating at least a portion of calcium from a material comprising calcium and magnesium. The present invention may include processes for producing high purity carbon dioxide, or high partial pressure carbon dioxide, or both. The present invention may include processes forming an aqueous magnesium sulfite solution. The present invention may include processes for producing magnesium sulfite solid from an aqueous solution comprising magnesium sulfite. The present invention may include processes for separating impurities from a solution comprising magnesium sulfite. The present invention may include processes for drying or dehydrating magnesium sulfite solid, or calcium sulfite solid, or both. The present invention may include low energy, or low cost, or low CAPEX, or low OPEX, or a combination thereof processes for drying or dehydrating magnesium sulfite solid, or calcium sulfite solid, or both.

DETAILED DESCRIPTION OF THE INVENTION

Example Definitions

Figure 1:
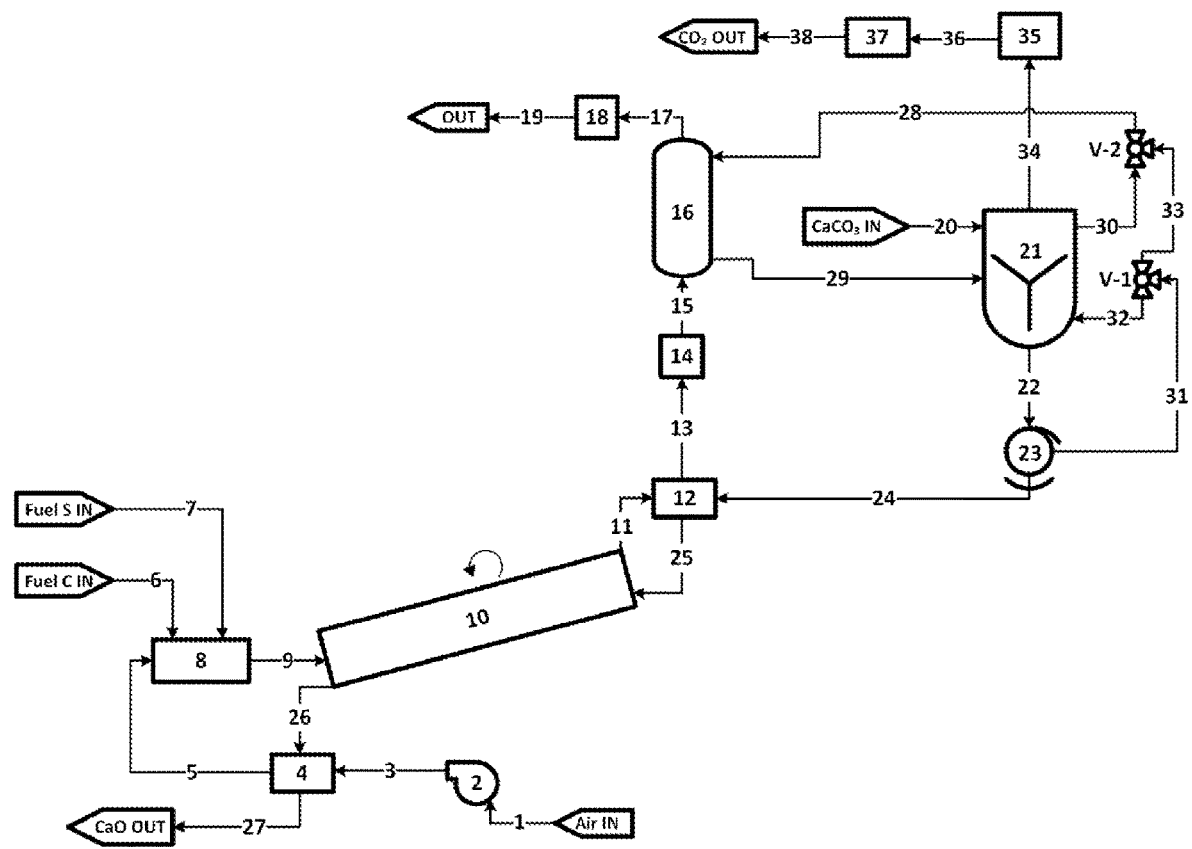
FIG. 1 shows an embodiment of a process for continuous production of CaO from CaCO3 or limestone or other typical CaO feedstocks.

Regenerable Acid Gas or Regenerable Acid: A regenerable acid may comprise an acidic chemical which can form a salt and is capable of being regenerated from said salt into its original acidic chemical form. For example, a regenerable acid may comprise an acid which can be reacted to form a salt and can be regenerated from said salt by, for example, thermal decomposition of said salt, which may involve, for example, a gas forming decomposition. For example, a regenerable acid may comprise an acid which can be reacted to form a salt and can be regenerated from said salt by, for example, electrochemical means, which may include, but is not limited to, electrodialysis. A regenerable acid gas may be an acid which is generally at a gas phase when said acid is at an isolated state under certain conditions. Regenerable acid and regenerable acid gas may be used interchangeably. Example regenerable acid gases or acids may include, but are not limited to, one or more or a combination of the following: sulfur dioxide, nitrogen dioxide, nitrogen monoxide, hydrogen sulfide, silicic acids, or orthosilicic acid. Example regenerable cation-acid gas salts may include, but are not limited to, one or more or a combination of the following: sulfites, bisulfites, metabisulfites, nitrites, carbonates, silicates, calcium sulfite, magnesium sulfite, calcium bisulfite, magnesium bisulfite, calcium nitrite, magnesium nitrite, calcium nitrate, magnesium nitrate, calcium carbonate, magnesium carbonate, calcium bicarbonate, magnesium bicarbonate, calcium silicates, magnesium silicates, sodium sulfite, sodium bisulfite, sodium metabisulfite, sodium nitrate, sodium nitrite, sodium carbonate, sodium bicarbonate, sodium sequicarbonate, sodium silicates, alkaline-earth metal cation salts, alkaline-earth metal cation salts withs anions described herein, alkali metal cation salts, alkali metal cation salts with anions described herein.

CaO: CaO may comprise calcium oxide. CaO may also be provided as an example oxide salt and may represent other oxide salts, which may include, but are not limited to, oxide salts of calcium, magnesium, sodium, potassium, lithium, ammonia, iron, zinc, aluminum, copper, or a combination thereof. CaO may also represent cement, which may include, but is not limited to, one or more or a combination of the following: hydraulic cement, non-hydraulic cement, or Portland cement. CaO may comprise a CO2-lean alkaline-earth.

CaCO3: CaCO3 may comprise calcium carbonate. CaCO3 may also be provided as an example carbon dioxide salt and may represent other carbon dioxide salts, which may include, but are not limited to, carbon dioxide salts of calcium, magnesium, sodium, potassium, lithium, ammonia, amine, iron, zinc, copper, or a combination thereof. CaCO3 may comprise limestone. CaCO3 may comprise a CO2-rich alkaline-earth.

CaSO3: CaSO3 may comprise calcium sulfite. CaSO3 may also be provided as an example regenerable acid gas salt and may represent other regenerable acid gas salts, which may include, but are not limited to, carbon dioxide salts of calcium, magnesium, sodium, potassium, lithium, ammonia, amine, iron, zinc, copper, or a combination thereof.

Carbon Dioxide Salt: A salt originating from or containing or comprising carbon dioxide. A carbon dioxide salt may include, but is not limited to, carbonates, bicarbonates, carbamates, sesquicarbonates, or a combination thereof.

Intermediate: An intermediate may comprise a reagent which is internally regenerated. An intermediate may comprise a reagent which is at least a portion regenerated inside the process. An intermediate may comprise a reagent which is not a primary input or output of the process. An intermediate may comprise a catalyst. Example intermediates may include, but are not limited to, one or more or a combination of the following: a regenerable acid gas or an absorption solution.

Combustion Gases or Post-Combustion Gases: Combustion gases or post-combustion gases may comprise gases or a gas mixture forming as a result of the combustion of one or more fuels.

Fuel-Rich Mixture: A mixture of fuel and an oxidant which possess a higher ratio of fuel to oxidant relative to a fuel-lean mixture. For example, mixture of fuel and an oxidant which possesses a ratio of fuel to oxidant which is close to, or equal to, or greater than the stoichiometric ratio of fuel to oxidant for complete combustion. Oxidant may comprise diatomic oxygen, air, or other oxidant.

Fuel-Lean Mixture: A mixture of fuel and an oxidant which possess a lower ratio of fuel to oxidant relative to a fuel-lean mixture. For example, mixture of fuel and an oxidant which possesses a ratio of fuel to oxidant which is close to, or equal to, or less than the stoichiometric ratio of fuel to oxidant for complete combustion. Oxidant may comprise diatomic oxygen, air, or other oxidant.

Low Oxygen Environment or Low Oxygen Atmosphere or Low Diatomic Oxygen Environment or Low Diatomic Oxygen: May comprise one or more or a combination of the following:

Comprises a diatomic oxygen concentration less than 20 vol %, or less than 15 vol %, or less than 10 vol %, or less than 9 vol %, or less than 8 vol %, or less than 7 vol %, or less than 6 vol %, or less than 5 vol %, or less than 4 vol %, or less than 3 vol %, or less than 2 vol %, or less than 1 vol %, or less than 0.5 vol %, or less than 0.25 vol %, or less than 0.1 vol %, or less than 0.05 vol %, or less than 0.01 vol %, or less than 0.005 vol %, or less than 0.001 vol %, or less than 0.0001 vol %.

A volume-percent concentration of gaseous diatomic oxygen less than average concentration of oxygen in air or a diatomic oxygen concentration of less than or equal to 21 vol %

Low Dissolved Oxygen Concentration or Low Dissolved Diatomic Oxygen Concentration:

A dissolved oxygen concentration less than 10,000 PPM, or less than 5,000 PPM, or less than 1,000 PPM, or less than 500 PPM, or less than 250 PPM, or less than 100 PPM, or less than 50 PPM, or less than 25 PPM, or less than 10 PPM, or less than 7.5 PPM, or less than 5 PPM, or less than 2.5 PPM, or less than 1 PPM.

Less than the saturated solubility of dissolved oxygen at the vapor pressure of diatomic oxygen in the headspace above a solution.

Carbonaceous Fuel: A fuel comprising carbon. A carbonaceous fuel may comprise a hydrocarbon, a carbon containing compound, elemental carbon, a mixture with carbon, or a combination thereof Sulfurous Fuel: A fuel comprising sulfur. A sulfurous fuel may include, but is not limited to, sulfur, elemental sulfur, hydrogen sulfide, hydrocarbons comprising sulfur, sulfur dioxide, sulfur trioxide, sulfides, salts comprising sulfur, mercaptans, organosulfur compounds, nitrogenous sulfur compound, ammonium sulfate, ammonium sulfite, ammonium sulfide, or a combination thereof.

Nitrogenous Fuel: A fuel comprising nitrogen. A nitrogenous fuel may include, but is not limited to, ammonia, amine, ammonia salts, ammonium salts, ammonium nitrate, ammonium nitrite, ammonium sulfite, ammonium sulfide, ammonium carbonate, ammonium carbamate, urea, ammonia derivatives, organic nitrogen compounds, hydrocarbons comprising nitrogen, or a combination thereof Hydrogen Fuel: A fuel comprising hydrogen. Hydrogen fuel may comprise diatomic hydrogen or derivatives of hydrogen.

Other Cement Feedstocks: Other cement feedstocks may comprise input materials for the production of cement other than calcium carbonate. For example, other cement feedstocks may include, but are not limited to, one or more or a combination of the following: clay, or silicon dioxide, or aluminum oxide, or iron oxide, or iron carbonate, or magnesium carbonate, or magnesium oxide, or silicates, or silicon oxides, or aluminates, or shale, or sand, or fly ash, or ash, or slag, or sulfur oxides.

Solid Material Undergoing Calcination: May comprise solid materials undergoing thermal decomposition and/or calcination. May comprise solid materials in a calciner. May comprise solid materials entering or exiting a calciner.

Calcining Products: Calcining products may comprise outputs of a calcination process. Calcining Products may refer to solid phase products exiting a calcination process, which may include, but are not limited to, alkaline-earth oxides, alkali oxides, calcium oxide, magnesium oxide, cement, or a combination thereof. Calcining products may refer to gaseous phase products exiting a calcination process, which may include, but are not limited to, sulfur dioxide, regenerable acid gas, carbon dioxide, or a combination thereof.

Thermal Decomposition: May comprise calcination reactions. May comprise an endothermic or temperature driven gas forming reaction. May comprise other calcination reactions. Other calcination reactions may include, but are not limited to, the formation of calcium silicates and/or calcium aluminates and/or sulfur based compounds.

First Combustion Step:

A first combustion step may comprise the combustion of a fuel in a gas or oxidant or both in at least a portion of a fresh gas or a gas mixture which previously did not undergo combustion.

May comprise combustion which decreases the gas phase diatomic oxygen concentration from 10-100 vol % to less than 20 vol %, or less than 19 vol %, or less than 18 vol %, or less than 17 vol %, or less than 16 vol %, or less than 15 vol %, or less than 14 vol %, or less than 13 vol %, or less than 12 vol %, or less than 11 vol %, or less than 10 vol %, or less than 9 vol %, or less than 8 vol %, or less than 7 vol %, or less than 6 vol %, or less than 5 vol %, or less than 4 vol %, or less than 3 vol %, or less than 2 vol %, or less than 1 vol %. Vol % of diatomic oxygen means the volume-percent concentration of diatomic oxygen in the gas phase.

Second Combustion Step:

A second combustion step may comprise the combustion of a fuel in a gas or oxidant or both in a gas or gas mixture which previously underwent combustion.

May comprise combustion which decreases diatomic oxygen concentration from 0.1-20 vol % to less than 20 vol %, or less than 15 vol %, or less than 10 vol %, or less than 9 vol %, or less than 8 vol %, or less than 7 vol %, or less than 6 vol %, or less than 5 vol %, or less than 4 vol %, or less than 3 vol %, or less than 2 vol %, or less than 1 vol %, or less than 0.5 vol %, or less than 0.25 vol %, or less than 0.1 vol %, or less than 0.05 vol %, or less than 0.01 vol %, or less than 0.005 vol %, or less than 0.001 vol %, or less than 0.0001 vol %.

Diatomic Oxygen-Rich Gas: A gas or gas mixture comprising a higher partial pressure or concentration or both of diatomic oxygen relative to a Diatomic Oxygen-Lean Gas. May comprise at least a portion of a gas or gas mixture which previously did not undergo combustion.

Diatomic Oxygen-Lean Gas: A gas or gas mixture comprising a higher partial pressure or concentration or both of diatomic oxygen relative to a Diatomic Oxygen-Ultra-Lean Gas. May comprise at least a portion of a gas or gas mixture which previously underwent combustion in a first combustion step.

Diatomic Oxygen-Ultra-Lean Gas: A gas or gas mixture comprising a lower partial pressure or concentration or both of diatomic oxygen relative to a Diatomic Oxygen-Lean Gas. May comprise at least a portion of a gas or gas mixture which underwent combustion in a second combustion step.

Combustion Step: A combustion step may comprise the combustion of a fuel. A combustion step may comprise the combustion of a fuel which results in a decrease in the partial pressure and/or concentration of diatomic oxygen in a gas stream. A combustion step may comprise the combustion of a fuel which results in the increase in temperature of a gas stream or is exothermic. A combustion step may comprise the combustion of a fuel until the fuel ceases to combust.

Carbon Dioxide Generation Step: A carbon dioxide generation step may comprise a reaction between a carbon dioxide salt and a regenerable acid gas, which results in the formation of carbon dioxide. Said formed carbon dioxide may be at a gaseous state.

Calcining Step: A calcining step may comprise a step involving heat input or thermal decomposition or an endothermic gas forming reaction or a temperature driven gas forming reaction or a combination thereof.

Acid Gas Recovery Step: An acid gas recovery step may comprise absorbing, separating, or capturing a regenerable acid gas.

Alkali: An alkali may comprise reagents comprising elements in the alkali metal group in the periodic table.

Alkaline-Earth: An alkaline-earth may comprise reagents comprising elements in the alkaline-earth metal group in the periodic table.

High Purity of Carbon Dioxide: A volume-percent (vol %) concentration of carbon dioxide greater than or equal to 30 vol %, or 40 vol %, or 50 vol %, or 60 vol %, or 70 vol %, or 80 vol %, or 90 vol %, or 95 vol %, or 99 vol %, or 100 vol %.

High Pressure: A partial pressure greater than or equal to 0.1 atm, or 0.5 atm, or 1 atm, or 1.5 atm, 2 atm, or 3 atm, or 4 atm, or 5 atm, or 6 atm, or 7 atm, or 8 atm, or 9 atm, or 10 atm, or 15 atm, or 20 atm.

Low Concentration of Water Vapor:
  A water vapor pressure less than or equal to 1 atm, or 0.75 atm, or 0.5 atm, or 0.25 atm, or 0.175 atm, or 0.1 atm, or 0.09 atm, or 0.08 atm, or 0.07 atm, or 0.06 atm, or 0.05 atm, or 0.04 atm, or 0.03 atm, or 0.02 atm, or 0.01 atm, or 0.005 atm.
  A water vapor vol % concentration less than or equal to 50 vol %, or 25 vol %, or 15 vol %, or 10 vol %, or 9 vol %, or 8 vol %, or 7 vol %, or 6 vol %, or 5 vol %, or 4 vol %, or 3 vol %, or 2 vol %, or 1 vol %.

Mild Temperature: A temperature less than or equal to 150° C., or 100° C., or 90° C., or 80° C., or 70° C., or 60° C., or 50° C., or 40° C., or 35° C. A temperature greater than or equal to −50° C., or −40° C., or −30° C., or −20° C., or −10° C., or 0° C.

CO2-Rich Alkaline-Earth Solid: An alkaline earth compound with a greater molar ratio of CO2 to alkaline-earth than CO2-Lean Alkaline-Earth Solid. May comprise calcium carbonate or magnesium carbonate or a combination thereof CO2-Lean Alkaline-Earth Solid: An alkaline earth compound with a lower molar ratio of CO2 to alkaline-earth than CO2-Lean Alkaline-Earth Solid. May comprise calcium oxide or magnesium oxide or cement or a silicate or a combination thereof.

Physical Absorbent or Physical Solvent or Solvent: A liquid or surface or a combination thereof wherein regenerable acid gas is soluble. A physical absorbent may comprise a non-aqueous solution. A physical absorbent may comprise water. A physical absorbent may comprise a mixture of a non-water reagent with water. A physical absorbent may comprise an aqueous solution.

Physical Absorbent Wash or Physical Solvent Wash or Solvent Wash: An absorption column or wash or contactor or scrubber or a gas-liquid contactor which employs physical absorbent as an absorption solution.

Middle Concentration: A concentration greater than a lean concentration and less than a rich concentration.

Example Chemistry

| Example Summary of Inputs and Outputs for the Present Invention | |
| --- | --- |
| Inputs | Outputs |
| CaCO$_3$ and/or Other Cement Feedstocks | CaO and/or Cement |
| Fuel (Carbonaceous Fuel and/or Sulfurous Fuel and/or Hydrogen Fuel and/or Nitrogenous Fuel) | Captured CO$_2$ |
| | Sulfurous Salt Waste-Product or Useful Byproduct |

Please note—the Sulfurous Fuel and Sulfurous Salt Waste-Product or Useful Byproduct may comprise significantly smaller mass or amounts than other inputs and outputs.

Reaction 1: Conversion of CaCO3 and SO2 or SO2 Solution into CaSO3 and Captured CO2

CaCO$_3$(s)+SO$_2$(rich-aq)⇒CaSO$_3$(s)+SO$_2$(lean-aq)+ CO$_2$(g)

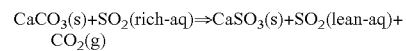

Description: The present reaction may involve reacting a carbon dioxide containing salt or carbonate salt, such as calcium carbonate, with a regenerable acid gas, such as sulfur dioxide, to form pressurized or high concentration or nearly pure CO2 and a regenerable acid gas salt, such as calcium sulfite. If desired, the present reaction may be conducted under mild temperature conditions, which may include, but are not limited to, room temperature, 0-100° C., or less than 200° C., or less than 190° C., or less than 180° C., or less than 170° C., or less than 160° C., or less than 150° C., less than 140° C., less than 130° C., or less than 120° C., less than 110° C., or less than 100° C., or less than 90° C., or less than 80° C., or less than 70° C., or less than 60° C., or less than 50° C., or less than 40° C., or less than 30° C. Alternatively, or additionally, it may be desirable to conduct the present step at relatively colder temperatures, to, for example, minimize the vapor pressure or concentration of SO2 in the headspace or gas phase. Relatively colder temperatures may include, but are not limited to, less than 50° C., or less than 45° C., or less than 40° C., or less than 35° C., or less than 30° C., or less than 25° C., less than 20° C., less than 15° C., or less than 10° C., or less than 5° C. The CO2 generated may comprise substantially lower concentrations of water vapor and/or other contaminants relative to desorbed carbon dioxide in some post-combustion CO2 capture systems, which may enable less or lower cost post-treatment and/or compression. The CO2 generated may be present at relatively high pressures, which may enable lower compression costs and/or lower compression energy demand if subsequent compression is desired. It may be desirable for the present reaction to be conducted in a low diatomic oxygen or diatomic oxygen free environment to, for example, prevent the formation of more permanent sulfur oxides, such as sulfates and/or sulfur trioxide. The present reaction may occur at a yield of 100% or may occur at a yield less than 100%. If the yield of the present reaction is less than 100%, a portion of calcium carbonate may be present in the solid reaction product. The sulfur dioxide may be dissolved in water. The sulfur dioxide may be dissolved in a solution comprising a physical absorbent. Said physical absorbent may comprise a one or more or a combination of reagents in which sulfur dioxide and/or other acid gases is soluble.

Conditions: It may be desirable to mix the input reagents under standard conditions, which may include, but are not limited to, room temperature pressure conditions. Alternatively, or additionally, reagents may be mixed under high pressure conditions to enable a higher partial pressure of CO2 during desorption and/or a lower vol % concentration of water vapor and/or SO2 relative to CO2 in the reactor headspace or atmosphere. It may be desirable to conduct the present reaction under a pure or nearly pure or high concentration CO2 atmosphere to, for example, enable the process to generate high quality or high concentration or high purity or a combination thereof captured CO2 and/or to minimize the need for additional treatment or compression during or after CO2 generation. Note that during the present reaction, temperatures and pressures may increase or decrease or a combination thereof. Reaction 1 may be exothermic and may be a gas forming reaction—temperatures and/or pressures may increase during Reaction 1. It may be desirable to facilitate an increase in temperatures and/or pressures, or it may be desirable to relieve an increase in temperatures and/or pressures.

Proof: 6 wt % aqueous SO2 (sulfurous acid purchased from Sigma Aldrich) was diluted to 0.3 wt % aqueous SO2 with DI water. The 0.3 wt % aqueous SO2 was mixed with 98% purity CaCO3(s) (purchased from Sigma Aldrich) at room temperature and pressure. 0.3 wt % aqueous SO2 is within or less than the likely concentration range of SO2 in the SO2-Rich solution based on SO2 solubility in water according to Henry's Law. Greater concentrations than 0.3 wt % SO2(aq) are possible and 0.3 wt % was tested as a conservative example. A gas forming reaction occurred. Using FTIR, the resulting gas phase was determined to comprise CO2. Using FTIR, the resulting solid phase was determined to comprise CaSO3.

Reaction 2: Calcination or Thermal Decomposition of CaSO3 into CaO and SO2

$$CaSO_3(s) \Rightarrow CaO(s) + SO_2(g)$$

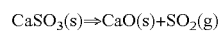

Reaction occurs at or above 780° C.

Description: Reaction 2 involves producing CaO and regenerating the acid gas. Reaction 2 may involve the thermal decomposition of calcium sulfite into calcium oxide and sulfur dioxide. Reaction 2 may be conducted in the presence of other cement feedstocks. Reaction 2 may produce cement as an output instead of, or in addition to, calcium oxide. For example, the present reaction may be conducted in the presence of other cement feedstocks to produce cement or Portland cement. The present reaction may be conducted in a kiln or other system employed for calcination. The present reaction may be retrofitted into or conducted in infrastructure designed for the calcination of cement or calcium carbonate or limestone or a combination thereof. The present reaction may be facilitated by a carrier gas, which may comprise hot combustion gases or a hot recirculated carrier gas or a combination thereof.

Note: A portion of sulfur dioxide or other sulfur compounds may be absorbed or reacted into the solid material undergoing calcination and/or may be present in the calcined products or at least a portion of the calcined products.

Note: Sulfur dioxide may be absorbed into other cement feedstocks and/or the calcined products if, for example, the present reaction is employed for the production of cement. Sulfur dioxide exiting the calciner as gaseous sulfur dioxide may comprise less sulfur dioxide than the amount of sulfur dioxide in the form of 'sulfite' present in the calcium sulfite input.

Conditions: The present thermal decomposition reaction may be conducted at elevated temperatures, which may include, but is not limited to, temperatures greater than 700° C., or greater than 720° C., or greater than 750° C., or greater than 780° C. The temperature range of the present reaction may be similar to the temperature range employed in the calcination of calcium carbonate. Heat may be supplied to power the thermal decomposition process, by, for example, including, but not limited to, hot combustion flue gases or hot carrier gases or a combination thereof, which may be passed over or through or in direct contact with the calcium sulfite. It may be desirable for the present reaction to be conducted in a low diatomic oxygen or diatomic oxygen free environment to, for example, prevent the formation of relatively permanent sulfur oxides, such as sulfates and/or sulfur trioxide. For example, said hot combustion flue gases may possess low concentrations of diatomic oxygen or may be diatomic oxygen free. If the reaction yield in 'Reaction 1' is less than 100%, there may be calcium carbonate present in the input calcium sulfite. Some calcination conditions of the calcium sulfite may be similar and/or applicable to the calcination conditions employed for calcium carbonate, enabling residual calcium carbonate to be thermally decomposed into calcium oxide and/or cement simultaneous to the thermal decomposition of calcium sulfite into calcium oxide during 'Reaction 2'.

The present reaction step may be conducted in the presence of clay, silicates or other reagents or materials present in a cement kiln during the production of cement, or a combination thereof. For example, calcium sulfite may be employed as a substitute for a portion of the calcium carbonate or calcium oxide or a combination thereof employed as an input feedstock during the production of cement. The resulting cement may comprise the same or similar composition or properties to Portland cement or other cements known in the art. The resulting cement may comprise the same or similar or superior properties to cements known in the art.

The present invention and/or the present reaction step may comprise a process for the production of cement. Said cement may comprise Portland cement. Said cement may comprise calcium oxide or other oxide salt, which may be carbonated or hydrated or otherwise reacted in a manner during the curing of said cement or plaster.

Proof: The thermal decomposition temperature and enthalpy of formation of calcium sulfite are documented in literature. Cubicciotti et al. (Cubicciotti, D., Sanjurjo, A., & Hildenbrand, D. L. (1977). The thermal decomposition of $CaSO_3$ and its enthalpy of formation. *Journal of The Electrochemical Society*, 124(6), 933) determined the decomposition temperature of calcium sulfite is 723° C. to 767° C. and its enthalpy of formation is −277 Kcal per mole, or −1159 kJ per mole. Matsuzaki et al. (Matsuzaki, R., Masumizu, H., Murakami, N., & Saeki, Y. (1978). The Thermal Decomposition Process of Calcium Sulfite. Bulletin of the Chemical Society of Japan, 51(1), 121-122. doi:10.1246/bcsj 0.51.121) found calcium sulfite starts decomposing at 640° C. and fully decomposes into calcium oxide and sulfur dioxide above 780° C.

Reaction 3: Absorption of SO2 into SO2-Lean Solution, Recovering SO2

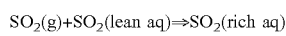

$SO_2(g) + SO_2(\text{lean aq}) \Rightarrow SO_2(\text{rich aq})$ $\Delta H = -23.2 \text{ kJ/mol}$ Absorption may occur at, for example, room temperature conditions or relatively cool conditions Description: Reaction 3 involves absorbing acid gas or separating acid gas from a gas mixture or a combination thereof. Reaction 3 may involve absorbing sulfur dioxide into an aqueous solution, separating at least a portion of the sulfur dioxide from a gas mixture, which may comprise post-combustion gases or flue gases. The resulting sulfur dioxide rich aqueous solution may comprise a suitable form of sulfur dioxide to employed in Reaction 1. At least a portion or all of the sulfur dioxide absorbed in Reaction 3 may be employed in Reaction 1. Sulfur dioxide may be reused internally, as may, for example, be expressed in Reactions 1-3. SO2(aq) from Reaction 3 may comprise the same SO2(aq) as is an input to Reaction 1.

The present reaction and/or the entire process may benefit or harness the greater solubility of SO2(aq) in water relative to carbon dioxide and/or the ability for SO2 to be continuously recirculated in the system. Unlike carbon dioxide, at gas partial pressures less than 1 atm and temperatures above 0° C., sulfur dioxide is soluble in water and may form a solution with a substantial concentration of dissolved SO2 (e.g. greater than 0.01 wt %). For example, 10 vol % SO2 in a gas stream with a total pressure of 1 atm can dissolve in water to form a solution with 0.826 wt % SO2 at 25° C. (according to Henry's Law), while a 10 vol % CO2 in a gas stream with a total pressure of 1 atm can dissolve in water to form a solution with 0.014 wt % CO2 at 25° C. Based on Henry's Law, SO2 possesses about 59 times or 5,900% greater solubility in water than CO2. The significantly greater solubility of SO2 relative to CO2 may be leveraged in the present process to produce captured CO2 and/or valuable oxide salts and/or valuable other salts by, for example, including, but not limited to, the ability to separate SO2(g) from gas streams with relatively low partial pressures of SO2(g) through dissolution in water and/or the react the resulting SO2(aq) directly with a CO2-containing salt to produce high partial pressure CO2(g) and a thermally decomposable SO2-containing salt. Advantageously, SO2 can be regenerated from the SO2-containing salt (such as Reactions 2 and 3) while producing a desired product oxide salt (Reaction 2).

Conditions: The present reaction or step may be conducted under conditions suitable or advantageous to enable the dissolution or absorption of an acid gas, such as SO2, into water or aqueous solution. For example, the present reaction may be conducted near or at or above atmospheric pressure and/or near or at or below atmospheric temperature. For example, the present reaction may conducted under conditions which may provide an desired or optimal balance between absorption rate and absorption capacity. For example, the present reaction may conducted under conditions which may provide greater absorption capacity, such as lower temperatures and/or greater pressures. For example, the present reaction may conducted under conditions which may provide greater absorption rate, such as higher temperatures and/or greater pressures. For example, the present reaction may conducted under conditions which are sufficiently cool to enable absorption capacity, such as, including, but is not limited to, one or more or a combination of the following temperature ranges: less than 100° C., or less than 90° C., or less than 80° C., or less than 70° C., or less than 60° C., or less than 50° C., or less than 40° C., or less than 30° C., or less than 25° C., or less than 20° C., or less than 15° C., or less than 10° C., or less than 5° C., or less than 0° C. For example, the present reaction may conducted under conditions which are sufficiently warm to prevent the formation of a solid phase, such as ice, which may include, but is not limited to, one or more or a combination of the following: greater than −15° C., greater than −10° C., greater than −5° C., or greater than 0° C. For example, the present reaction may be conducted with partial pressures or volume % concentrations or combinations thereof of acid gas which are sufficient to enable a sufficiently concentrated acid gas solution, which may include, but is not limited to, one or more or a combination of the following: greater than 10 PPM, or greater than 100 PPM, or greater than 1000 PPM, or greater than 0.1%, or greater than 0.5%, or greater than 1%, or greater than 2%, or greater than 3%, or greater than 4%, or greater than 5%, or greater than 6%, or greater than 7%, or greater than 8%, or greater than 9%, or greater than 10%.

Proof: According to Henry's Law, a 10 vol % SO2 in a gas stream with a total pressure of 1 atm can dissolve in water to form a solution with 0.826 wt % SO2(aq) at 25° C. 0.826 wt % SO2(aq) is a greater concentration than the weight-percent concentration of SO2(aq) in the experimental proof for Reaction 1.

Note: A sufficiently concentrated acid gas solution may comprise a solution with a concentration of dissolved acid gas comprising greater than or equal to one or more or a combination of the following concentrations: 0.0001 wt %, or 0.001 wt %, or 0.01 wt %, or 0.05 wt %, or 0.1 wt %, or 0.2 wt %, or 0.3 wt %, or 0.4 wt %, or 0.5 wt %, or 0.6 wt %, or 0.7 wt %, or 0.8 wt %, or 0.9 wt %, or 1 wt %, or 1.1 wt %, or 1.2 wt %, or 1.3 wt %, or 1.4 wt %, or 1.5 wt %, or 1.6 wt %, or 1.7 wt %, or 1.8 wt %, 1.9 wt %, or 2.0 wt %, or 2.5 wt %, or 3 wt %, or 3.5 wt %, or 4 wt %, or 4.5 wt %, or 5 wt %.

Note: During or before or after one or more or a combination of the above reactions, a portion of the sulfur oxides may be exposed to oxygen and may form a portion of more permanent oxides, such as sulfates or sulfur trioxide. Said exposure to diatomic oxygen may be inadvertent or incidental or unintentional or accidental. The presence of more permanent sulfur oxides may have a minimal impact or may be beneficial to the output calcium oxide or cement, especially if said more permanent sulfur oxides exist at a relatively low concentration. A relatively low concentration may include, but is not limited to, one or more or a combination of the following: less than 1 wt %, or less than 2 wt %, or less than 3 wt %, or less than 4 wt %, or less than 5 wt %, or less than 6 wt %, or less than 7 wt %, or less than 8 wt %, or less than 9 wt %, or less than 10 wt %, or less than 15 wt %, or less than 20 wt %, or less than 30 wt %, or less than 40 wt %, or less than 50 wt %.

Heat Input Requirements

| Reactions Requiring Heat | Heat Input Required |
|---|---|
| $CaSO_3(s) \Rightarrow CaO(s) + SO_2(g)$ | $\Delta H = +226.3 \frac{kJ}{mol}$ |
| | or |
| | 4,035.5 MJ per Metric Ton of CaO |
| Total | 4,035.5 MJ per Metric Ton of CaO |

| Comparison of Heat Input Required | | |
|---|---|---|
| Reaction (Representative of Type of Process) | $CaSO_3(s) \Rightarrow CaO(s) + SO_2(g)$ | $CaCO_3(s) \Rightarrow CaO(s) + CO_2(g)$ |
| Heat Input Temperature | >780° C. | >900° C. |
| Heat Input Required | $\Delta H = +226.3 \frac{kJ}{mol}$ | $\Delta H = +172 \frac{kJ}{mol}$ |
| | or | or |
| | 4,035.5 MJ per Metric Ton CaO | 3,067.2 MJ per Metric Ton CaO |

CO2 Emissions

| Comparison of $CO_2$ Emissions by Reaction | | |
|---|---|---|
| Reaction (Representative of Type of Process) | $CaSO_3(s) \Rightarrow CaO(s) + SO_2(g)$ | $CaCO_3(s) \Rightarrow CaO(s) + CO_2(g)$ |
| Heat Input Temperature | >780° C. | >900° C. |
| Heat Input Required | $\Delta H = +226.3 \frac{kJ}{mol}$ | $\Delta H = +172 \frac{kJ}{mol}$ |
| | or | or |
| | 4,035.5 MJ per Metric Ton CaO | 3,067.2 MJ per Metric Ton CaO |
| $CO_2$ Emissions from Heat (if Fuel is Natural Gas) | 0.199 Metric Ton $CO_2$ per Metric Ton CaO | 0.151 Metric Ton $CO_2$ per Metric Ton CaO |
| $CO_2$ Emissions from Heat (if Fuel is Coal) | 0.618 Metric Ton $CO_2$ per Metric Ton CaO | 0.470 Metric Ton $CO_2$ per Metric Ton CaO |
| $CO_2$ Emissions from Heat (if Fuel is Carbon-Free) | 0 Metric Ton $CO_2$ per Metric Ton CaO | 0 Metric Ton $CO_2$ per Metric Ton CaO |
| $CO_2$ Emissions from Thermal Decomposition Reaction | 0 Metric Tons $CO_2$ per Metric Ton CaO | 0.784 Metric Ton $CO_2$ per Metric Ton CaO |
| Total $CO_2$ Emissions (if Natural Gas is Fuel) | 0.199 Metric Ton $CO_2$ per Metric Ton CaO | 0.935 Metric Ton $CO_2$ per Metric Ton CaO |
| Total $CO_2$ Emissions (if Coal is Fuel) | 0.618 Metric Ton $CO_2$ per Metric Ton CaO | 1.254 Metric Ton $CO_2$ per Metric Ton CaO |

-continued

Comparison of $CO_2$ Emissions by Reaction

| Reaction (Representative of Type of Process) | $CaSO_3(s) \Rightarrow CaO(s) + SO_2(g)$ | $CaCO_3(s) \Rightarrow CaO(s) + CO_2(g)$ |
|---|---|---|
| Total $CO_2$ Emissions (if Fuel is Carbon-Free) | 0 Metric Ton $CO_2$ per Metric Ton CaO | 0.784 Metric Ton $CO_2$ per Metric Ton CaO |

Note: CO2 emissions may be net negative if the full lifecycle, including the absorption of CO2 from the air during downstream uses of CaO, such as in cement, non-hydraulic cement, plaster, or quicklime.

Note: CO2 emissions from the production of CaSO3 may be net zero because, for example, the CO2 generated from the reaction converting CaCO3 to CaSO3 is high purity, captured CO2, which may be directly employed in utilization, conversion, and/or sequestration.

Cost of Inputs, Value of Outputs, and Operating Profit

| Reaction (Representative of Type of Process) | $CaSO_3(s) \Rightarrow CaO(s) + SO_2(g)$ | $CaSO_3(s) \Rightarrow CaO(s) + CO_2(g)$ |
|---|---|---|
| Inputs and Cost of Inputs | 1.783 Metric Tons of $CaCO_3$ = $89.15<br>0.199 Metric Tons of Nat. Gas = $10.38 | 1.783 Metric Tons of $CaCO_3$ = $89.15<br>0.151 Metric Tons of Nat. Gas = $7.87 |
| Total Cost (Inputs) | $99.53 per metric ton of CaO Produced | $97.02 per metric ton of CaO Produced |
| Outputs and Value of Outputs | 1 Metric Tons of CaO = $117.80<br>0.784 Metric Tons of Pure $CO_2$ = $27.21 (without 45Q)<br>0.784 Metric Tons of Pure $CO_2$ = $54.42 (with 45Q) | 1 Metric Tons of CaO = $117.80<br>0.784 Metric Tons $CO_2$ Flue Gas = $0 |
| Total Value (Outputs) | $145.02 (without 45Q) per metric ton of CaO Produced<br>$172.23 (with 45Q) per metric ton of CaO Produced | $117.80 per metric ton of CaO Produced |
| Net Profit | $45.49 (without 45Q) per metric ton of CaO Produced<br>$72.70 (with 45Q) per metric ton of CaO Produced | $20.78 per metric ton of CaO Produced |

Example Figure Descriptions

FIG. 1: Embodiment of a process for continuous production of CaO from CaCO3 or limestone or other typical CaO feedstocks. SO2 is provided as an example regenerable acid gas.

Figure 2:
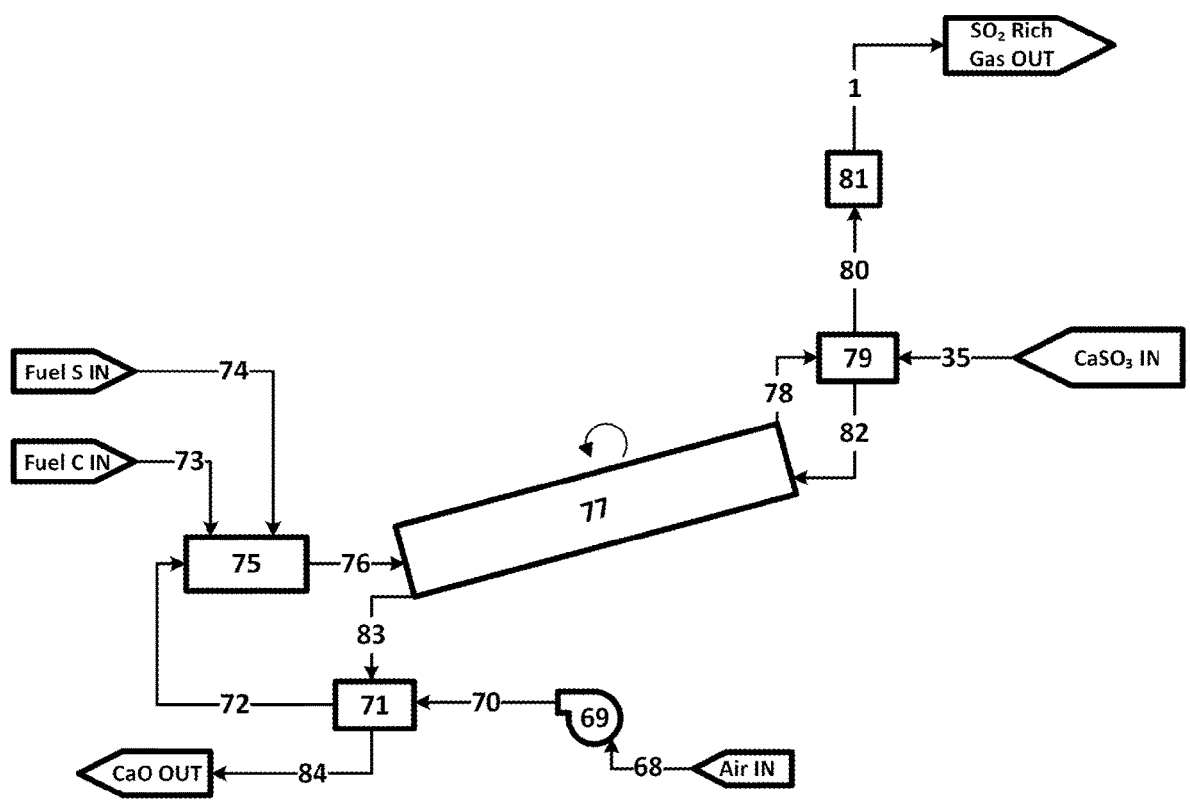
FIG. 2 shows an embodiment comprising a process for producing CaO from CaSO3.

FIG. 2: Embodiment comprising a process for producing CaO from CaSO3. The present embodiment may comprise a portion of an overall process for the production of CaO from CaCO3 or limestone or other typical CaO feedstocks. For example, the present embodiment may comprise a portion of an overall process for the production of CaO wherein other portions of the process may comprise a batch or semi-batch or continuously stirred reactor (CSTR) or continuous process or a combination thereof, such as embodiments shown in FIGS. 3A-3C.

Figure 3A:
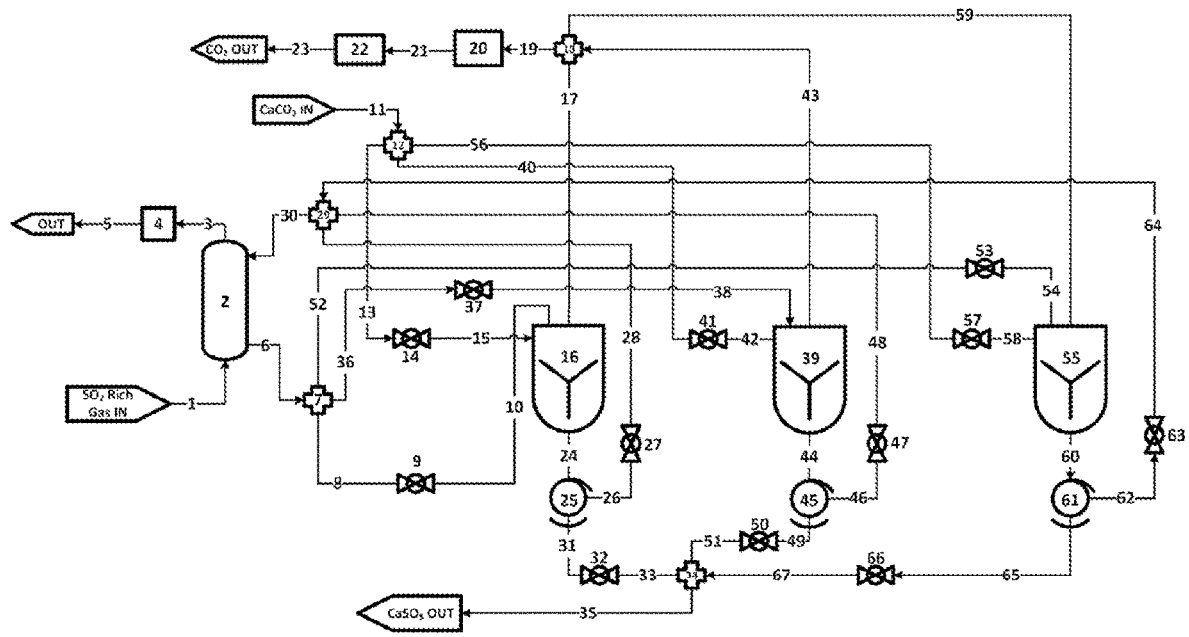
FIG. 3A shows an embodiment comprising a process for producing CaSO3 and CO2 from CaCO3 and SO2.

FIG. 3A: Embodiment comprising a process for producing CaSO3 and CO2 from CaCO3 and SO2. For example, the present embodiment may comprise a portion of an overall process for the production of CaO from CaCO3 and may comprise the present figure combined with FIG. 2. The present figure may comprise a batch or semi-batch or semi-continuous configuration. The present figure may show the present embodiment in a stage of a sequence of stages.

For example, the stages in a sequence may comprise:

1. First Stage: CaCO3 may be added to the first reactor ('16')
2. Second Stage: H2SO3 or SO2(aq) or dissolved SO2 or liquid SO2 or gaseous SO2 or SO2 or a combination thereof may be added to the second reactor ('39') which may result in the production of CO2 and the formation of CaSO3(s)
3. Third Stage: CaSO3(s) and remaining water or remaining solution may be drained or removed from the third reactor ('55'). The CaSO3(s) may be separated ('61') from the remaining water or solution.

Figure 3B:
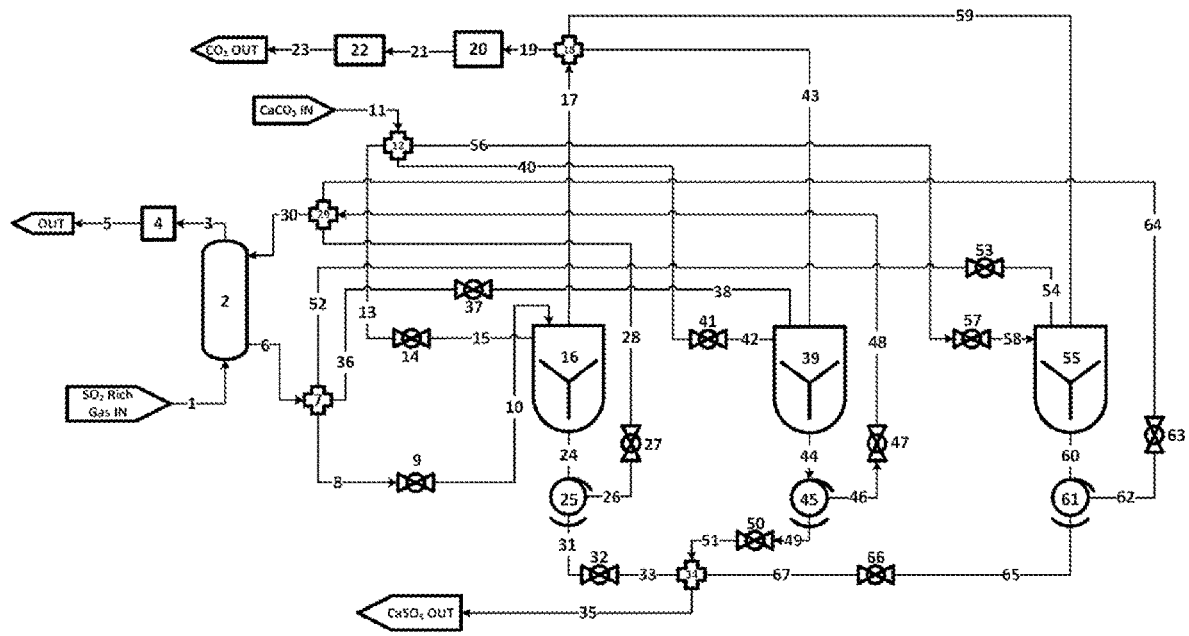
FIG. 3B shows an embodiment comprising a process for producing CaSO3 and CO2 from CaCO3 and SO2 with each reactor undergoing a different stage than in FIG. 3A.

FIG. 3B: Same embodiment as FIG. 3A. The present figure shows each reactor undergoing a different stage than in FIG. 3A. In the present embodiment, the sequence of stages may comprise multiple stages. For example, the present embodiment may involve the sequence of stages described in the figure description of FIG. 3A.

Figure 3C:
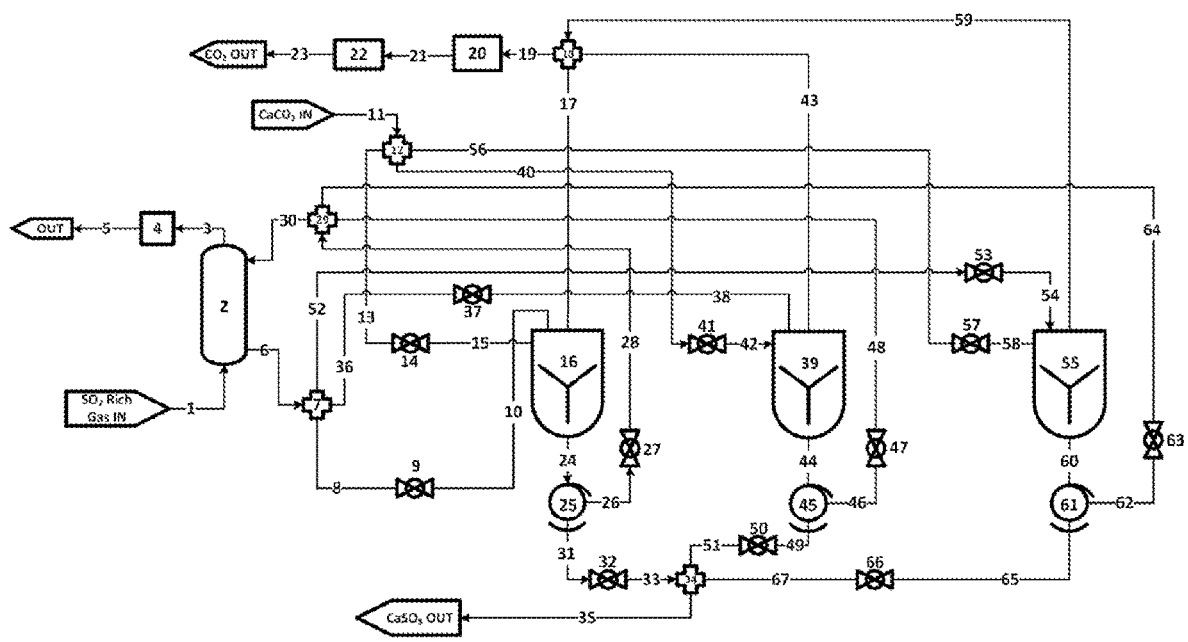
FIG. 3C shows an embodiment comprising a process for producing CaSO3 and CO2 from CaCO3 and SO2 with each reactor undergoing a different stage than in FIG. 3A.
Figure 4:
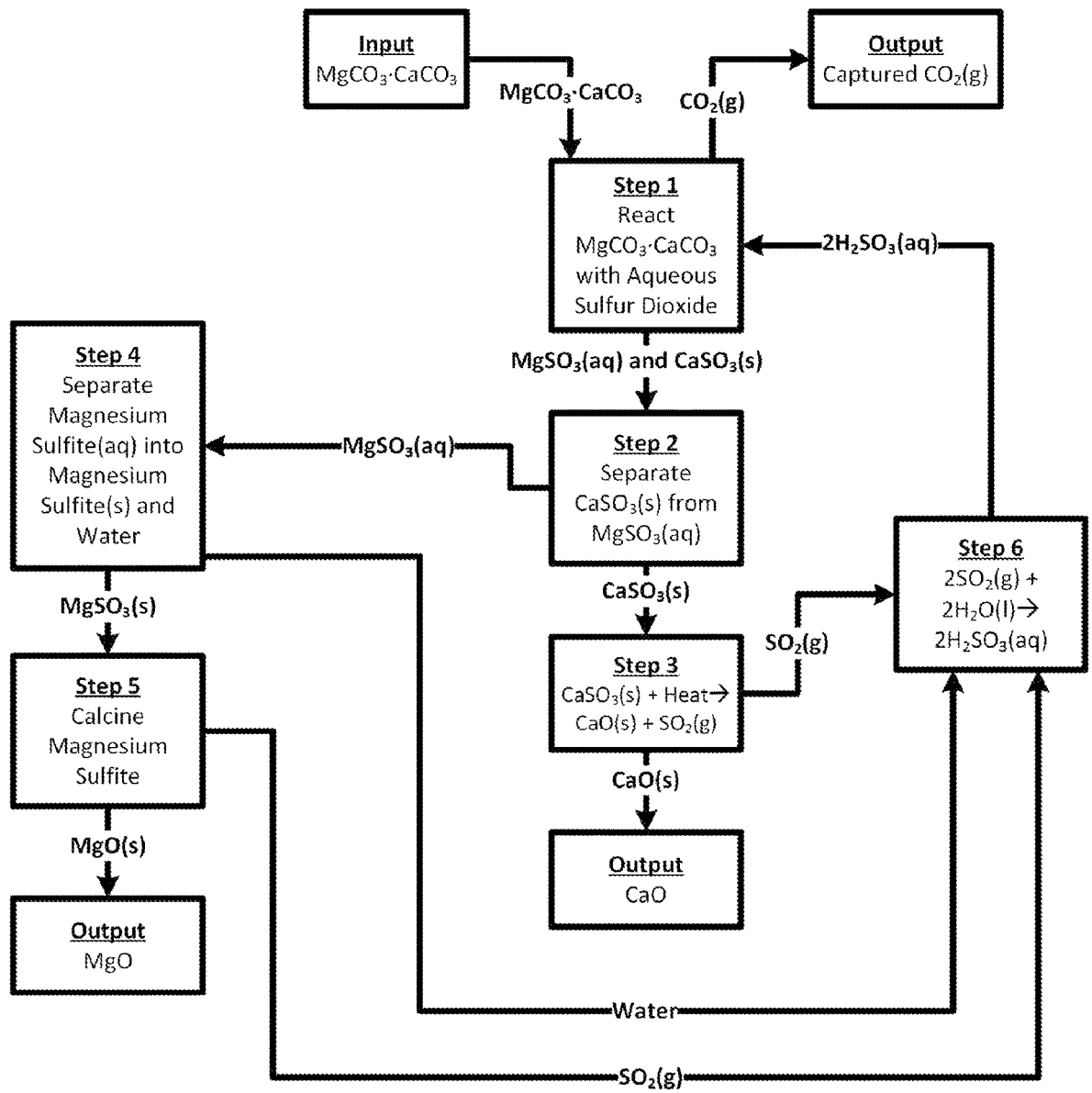
FIG. 4: A process for producing calcium oxide and magnesium oxide from a material comprising calcium and magnesium which may involve a process for concentrating and/or precipitating magnesium sulfite, and/or may involve calcining wet calcium sulfite and/or wet magnesium sulfite, and/or may involve producing captured carbon dioxide.
Figure 5:
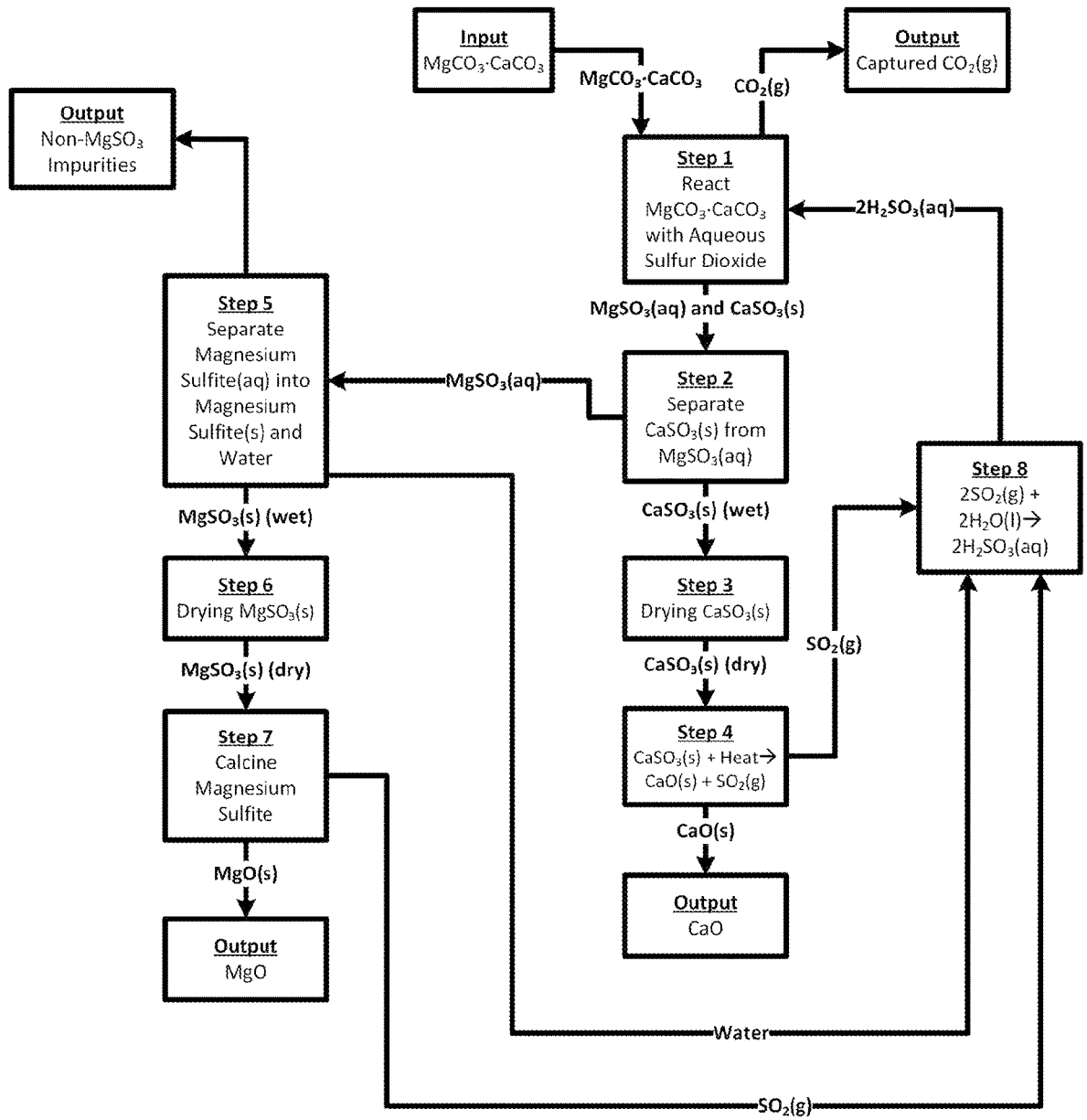
FIG. 5: A process for producing calcium oxide and magnesium oxide from a material comprising calcium and magnesium which may involve a process for drying wet calcium sulfite and/or wet magnesium sulfite before calcining calcium sulfite and/or magnesium sulfite and/or may involve absorbing sulfur dioxide gas in a permeate comprising water produced from a membrane-based process.
Figure 6:
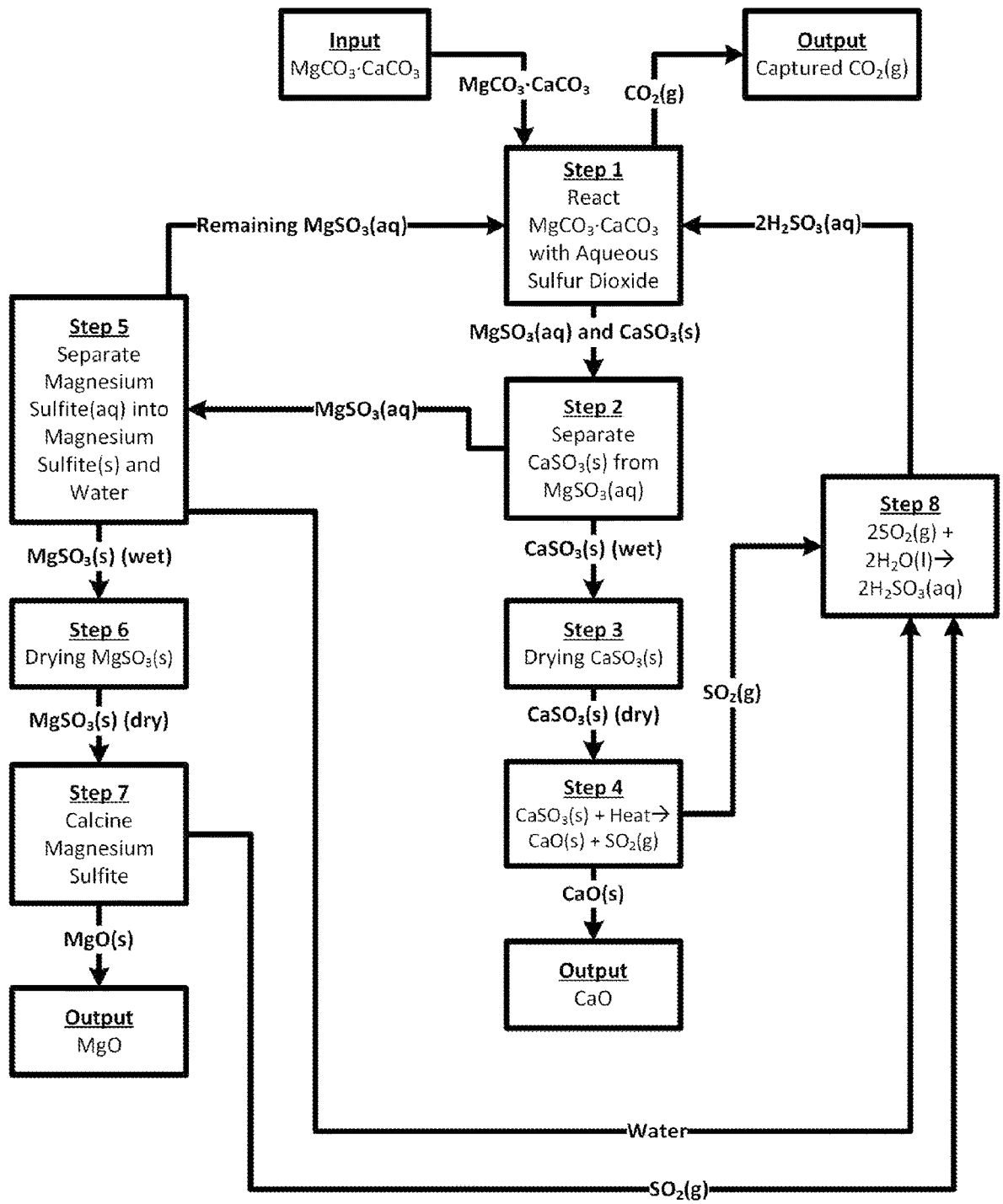
FIG. 6: A process for producing calcium oxide and magnesium oxide from a material comprising calcium and magnesium which may involve recirculating residual aqueous magnesium sulfite.
Figure 7:
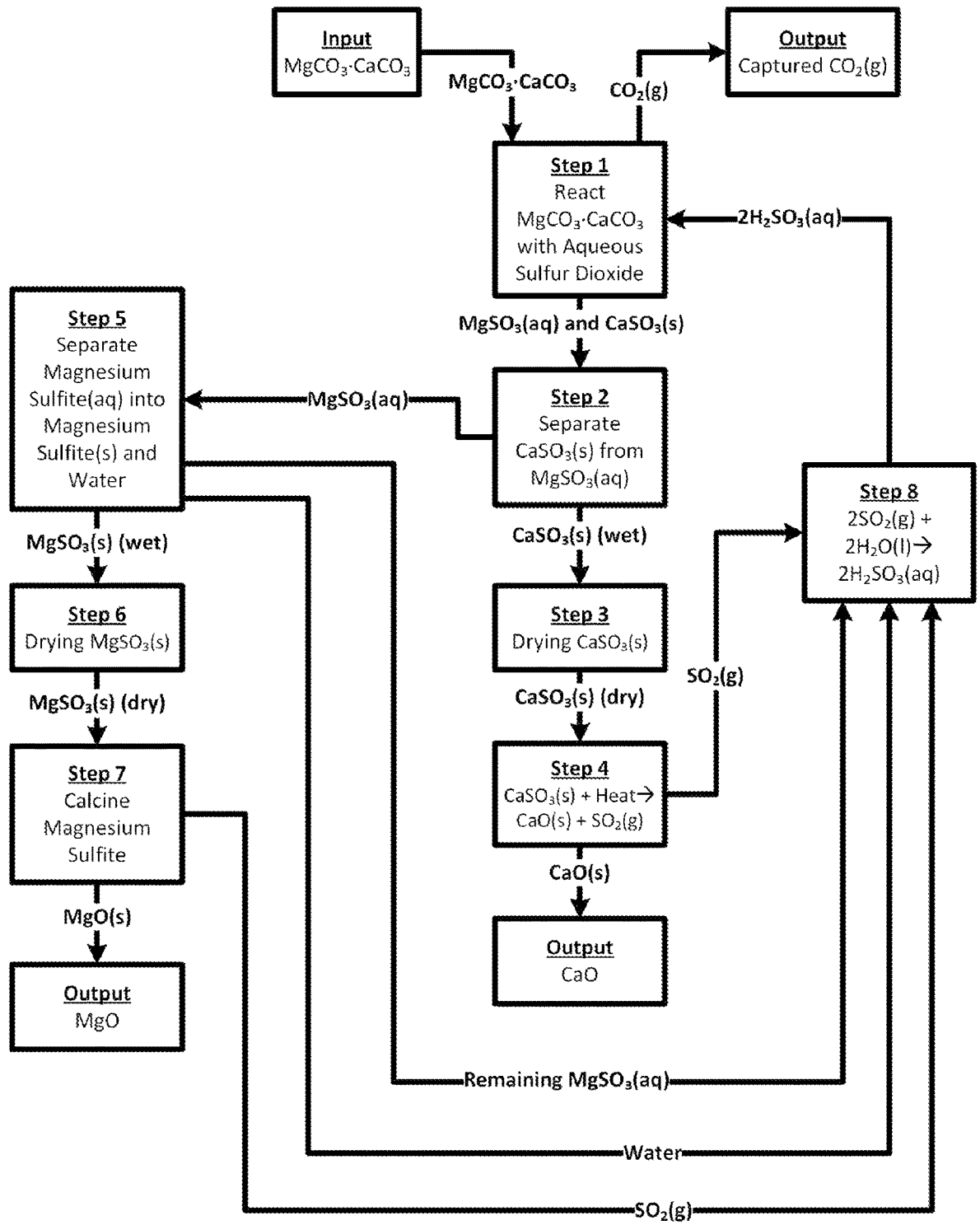
FIG. 7: A process for producing calcium oxide and magnesium oxide from a material comprising calcium and magnesium which may involve transferring residual aqueous magnesium sulfite to a sulfur dioxide absorption process.
Figure 8:
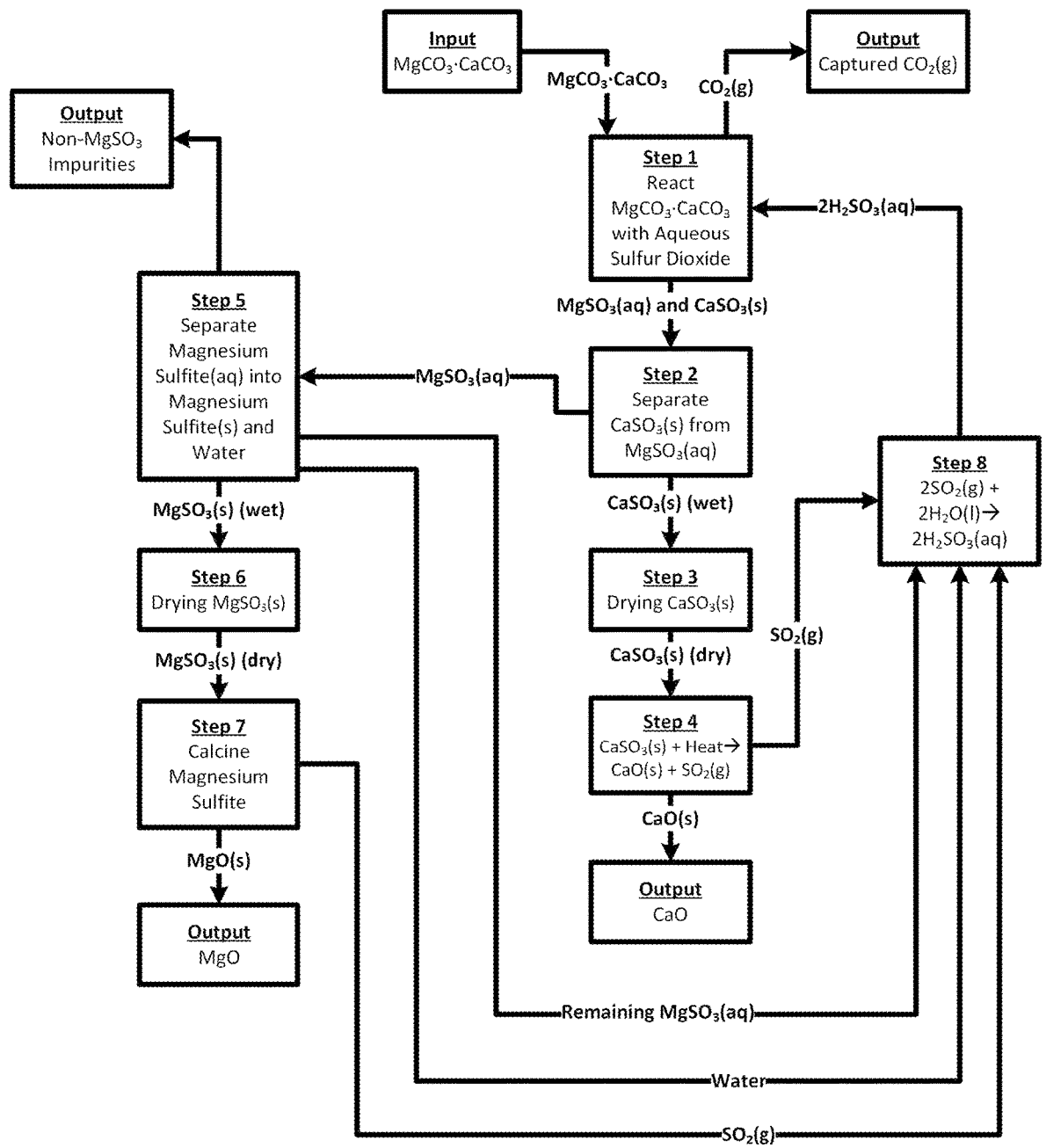
FIG. 8: A process for producing calcium oxide and magnesium oxide from a material comprising calcium and magnesium which may involve a process for removing at least a portion of non-magnesium sulfite impurities from a solution comprising aqueous magnesium sulfite.
Figure 9:
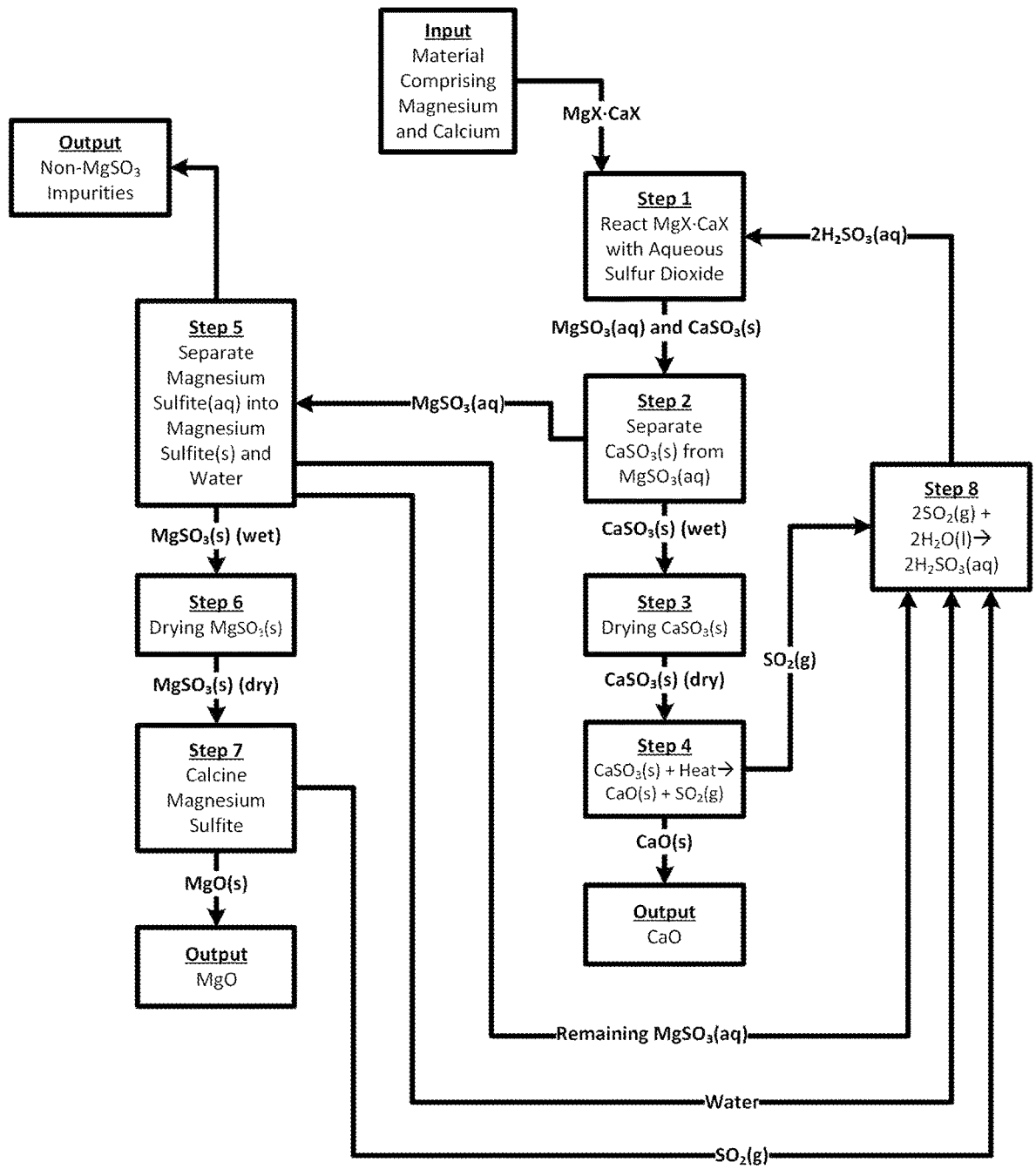
FIG. 9: A process for producing calcium oxide and magnesium oxide from a material comprising calcium and magnesium which may involve producing calcium oxide and/or magnesium oxide without a captured CO2 co-product during the reaction of the material comprising calcium and/or magnesium with aqueous sulfur dioxide.
Figure 10:
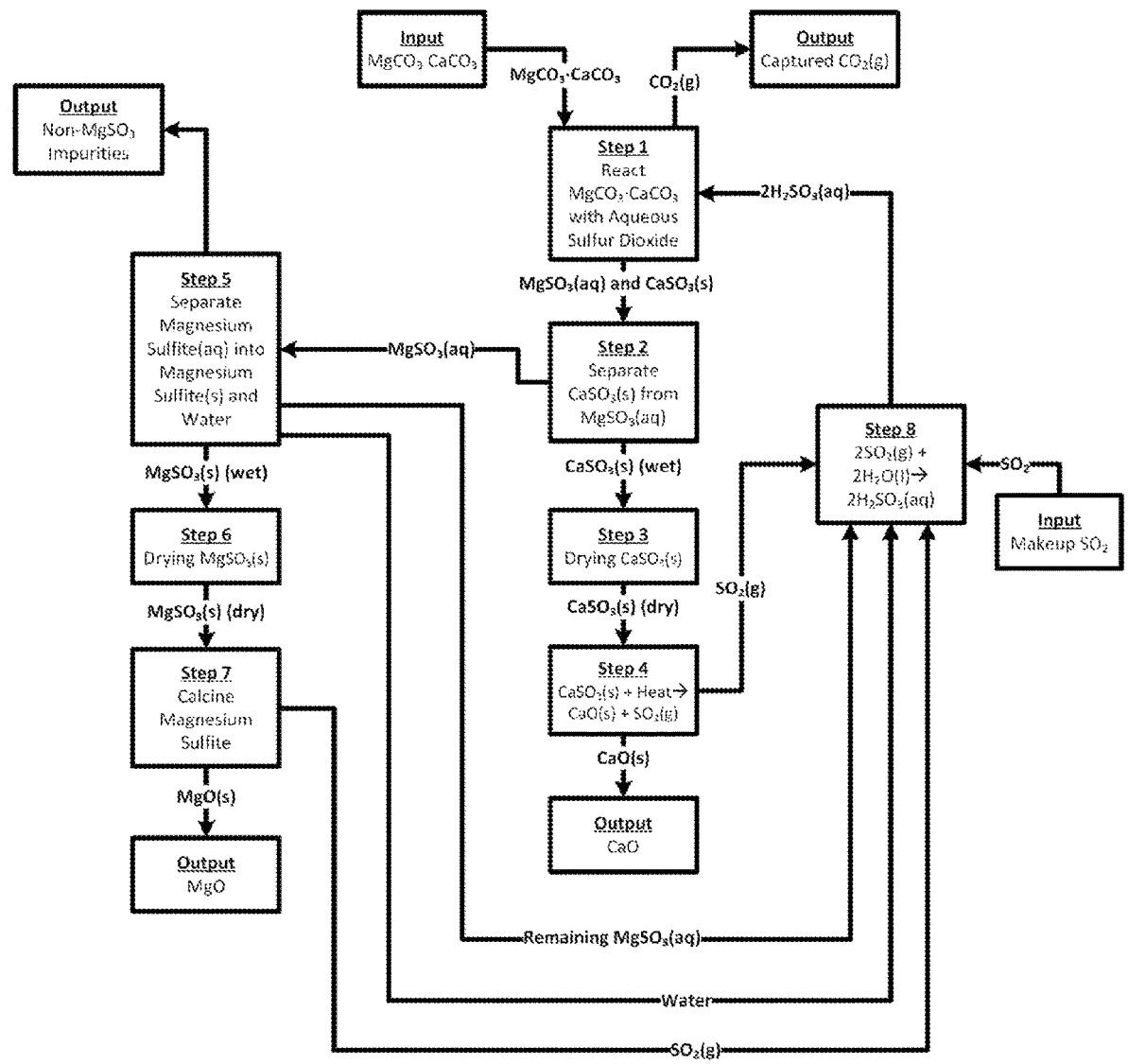
FIG. 10: A process for producing calcium oxide and magnesium oxide from a material comprising calcium and magnesium including makeup sulfur dioxide.

FIG. 3C: Same embodiment as FIG. 3A. The present figure shows each reactor undergoing a different stage than in FIG. 3A. In the present embodiment, the sequence of stages may comprise multiple stages. For example, the present embodiment may involve the sequence of stages described in the figure description of FIG. 3A.

Example Figure Keys

Example FIG. 1 Key

| # | Process Element Descriptions |
|---|---|
| 1 | Air Input - Air or other gas comprising at least a portion oxygen. |
| 2 | Gas Blower or Air Blower or Other Air Pump - Pump or Fan or Blower to pressurize or transfer or a combination thereof air or other gas comprising at least a portion oxygen into the system. |
| 3 | Air Post '2' - Air or other gas comprising at least a portion oxygen after the gas blower. The temperature of '3' may be similar to the temperature of the air source or the surrounding outside air temperature. The temperature of '3' may be less than the temperature in '5'. |
| 4 | Heat Exchanger or Contact Heat Exchanger or Lime Cooler- '3', which may comprise air, may be heat exchanged with hot CaO ('26'), which may result in pre-heated air and cooled CaO. '3' may be directly contacted with the CaO, cooling the CaO, while heating the air. If the air or other oxygen containing gas is in direct contact with CaO, it may be desirable to prevent the air or other oxygen containing gas from entering '10' or other environment potentially containing sulfur oxides or recoverable sulfur oxides to prevent, for example, oxidation of $SO_2$ and/or sulfite into $SO_3$ and/or sulfate. Alternatively, or additionally, '3' may be indirectly contacted or heat exchanged with the CaO, cooling the CaO, while heating the air. |
| 5 | Pre-Heated Air - Air which may have been preheated by in '4'. '5' may comprise the air fed into the combustion or fuel burning process. |
| 6 | Carbonaceous Fuel Input - A fuel comprising carbon ('6') may be fed or injected into a fuel firing or combustion step ('8'). Carbonaceous fuel may include, but is not limited to, natural gas, coal, pulverized coal, biomass, charcoal, oil, diesel, gasoline, kerosene, LPG, ethane, propane, butane, or a combination thereof. In some embodiments, it may be desirable to burn the carbonaceous fuel ('6') and/or sulfurous fuel ('7') at a ratio with oxygen such that minimal non-reacted oxygen or diatomic oxygen is present in post combustion gases (post-combustion gases may include, but are not limited to, '9'). |
| 7 | Sulfurous Fuel Input - A fuel comprising sulfur ('7') may be fed or injected into a fuel firing or combustion step ('8'). Sulfurous fuel may include, but is not limited to, sulfur, elemental sulfur, sour gas, hydrogen sulfide, sulfur dioxide, sulfur monoxide, ammonium sulfate, ammonium sulfite, or a combination thereof. In some embodiments, it may be desirable to burn the sulfurous fuel ('7') and/or carbonaceous ('6') at a ratio with oxygen such that minimal non-reacted oxygen or diatomic oxygen is present in post combustion gases (for example - '9'). Sulfurous fuel may be employed to reduce the concentration of oxygen in the combustion gases. Sulfurous fuel may be employed to reduce the concentration of oxygen in the combustion gases instead of rich carbonaceous fuel - air ratios, preventing or minimizing incomplete combustion and/or the formation of carbon monoxide. Sulfurous fuel may be employed to as a make-up for any sulfur dioxide losses. Alternatively, or additionally, a nitrogenous fuel, such as ammonia or an ammonia salt or an ammonia derivative, may be employed introduced or combusted in '7'. |
| 8 | Combustion chamber or Firing Fan - A chamber or step for combusting fuel to generate high temperature gases for the calcination or thermal decomposition process. '8' may be designed or optimized to minimize the concentration of oxygen in the combustion gases exiting '8' and/or maximize combustion efficiency. |
| 9 | Input Hot Combustion Gases, $SO_2$-Lean - '9' may comprise the hot combustion gases exiting '8' and entering the calcination step or kiln or rotating kiln '10'. Although '9' may contain sulfurous gases, such as sulfur dioxide, the concentration of the sulfurous gases in '9' may desirably be lower than the concentration of sulfurous gases in the gases exiting the kiln, '11'. '9' may possess minimal or ultra-low concentrations of diatomic oxygen to prevent or minimize the formation of sulfates and other practically permanent sulfur compounds or salts or further oxidized sulfur compounds. |
| 10 | Calcination Step or Kiln or Rotating Kiln - '10 may comprise a kiln for the thermal decomposition of acid gas salts into 'acid-gas' and oxide salt. For example, '10' may comprise a kiln for the thermal decomposition of calcium sulfite into sulfur dioxide and calcium oxide. '10' may comprise a rotating kiln or other kiln. Applicable kilns may include, but are not limited to, kilns employed in the art for the calcination of limestone, or calcination of calcium carbonate, or the production of cement, or a combination thereof. Calcium sulfite may be fed into the kiln and thermally decomposed into at least a portion of sulfur dioxide and calcium oxide using heat from, for example, hot combustion gases, '9', which may be directly passed through or over or in direct contact with said calcium sulfite. Warm calcium oxide, '26', and $SO_2$-Rich flue gases or combustion gases, '11', may comprise outputs of '10'. |
| 11 | Hot Flue Gases, $SO_2$-Rich - '11' may comprise the hot flue gases exiting the kiln, '10'. '11' may comprise a high concentration of $SO_2$ due to, for example, the thermal decomposition or calcination of calcium sulfite in the kiln, '10', and the $SO_2$ present in the Input Hot Combustion Gases, '9'. At least a portion or all of said '$SO_2$', may be recovered, recycled internally, and/or removed from the gases in '11' in subsequent steps before at least a portion of the gases in '11' exit the process. '11' may also comprise particulates which may require separation or removal from the gas stream in subsequent steps. |
| 12 | Heat Exchanger or Contact Heat Exchanger or Calcium Sulfite Pre-Heater - '11', which may comprise $SO_2$-Rich hot flue gases, may be heat exchanged with cold |

Example FIG. 1 Key

| # | Process Element Descriptions |
|---|---|
| | calcium sulfite ('24'), which may result in pre-cooled $SO_2$-Rich flue gases, '13', and pre-heated $CaSO_3$, '25'. $SO_2$-Rich hot flue gases may be directly contacted with the $CaSO_3$. The $SO_2$-Rich hot flue gases may be directly contacted with the $CaSO_3$, for example, because the $SO_2$-Rich hot flue gases may possess an ultra-low concentration of diatomic oxygen, which may prevent the $CaSO_3$ from oxidizing into a sulfate and may facilitate the heating and/or decomposition of $CaSO_3$. |
| 13 | Pre-Cooled $SO_2$-Rich Flue Gas - '13' may comprise pre-cooled $SO_2$-Rich flue gas, which may possess particulates which may need to be, at least in part, removed before the $SO_2$ absorption column, '16'. '13' may undergo additional cooling before or during '14'. An additional gas blower may be required to transfer '13', which may not be shown in a figure. |
| 14 | Particulate Remover or Baghouse or Electrostatic Precipitator, or Filter, or a combination thereof- '14' may comprise one or more or a combination of steps to remove particulate matter from '13'. |
| 15 | Pre-Cooled $SO_2$-Rich Flue Gas after Particulate Removal - '15' may comprise pre-cooled $SO_2$-Rich flue gas with at least a portion or most of the particulates removed relative to '13'. '15' may undergo additional cooling or treatment before entering the $SO_2$ absorption column or absorption step, '16'. |
| 16 | $SO_2$ Absorption Column - '16' may comprise an absorption column or contactor which facilitates the absorption of $SO_2$ from $SO_2$-Rich Flue Gas ('15') into an $SO_2$-Lean aqueous solution ('28'), forming an $SO_2$ - rich aqueous solution ('29') and an $SO_2$-Lean Flue Gas Stream ('17'). It may be desirable for '16' to selectively absorb $SO_2$, while minimally absorbing $CO_2$. Water or water scrubbing may be employed to selectively absorb $SO_2$, while minimally absorbing $CO_2$ due to the significantly greater solubility of $SO_2$ in water than $CO_2$. |
| 17 | $SO_2$-Lean Flue Gas after $SO_2$ Absorption - '17' may comprise $SO_2$-Lean flue gas following the absorption of $SO_2$ in '16'. '17' may undergo additional treatment before exiting the process, '18'. |
| 18 | $SO_2$ Scrubbing and/or Other Further Treatment - '18' may comprise an $SO_2$ scrubbing step to remove most of or practically all the remaining or residual $SO_2$ in '17', which may result in an $SO_2$ ultra-lean flue gas stream, '19'. '18' may involve a scrubbing process which selectively absorbs dilute concentrations of $SO_2$, while minimally absorbing $CO_2$. For example, the absorption solution may comprise a bicarbonate, or carbonate, or carbamate, or combination thereof salt or a mixture of salts. For example, the absorbent and/or adsorbent may comprise one or more absorbents and/or adsorbents known in the art for removing $SO_2$ and/or other acid gases from flue gas streams or gas streams. '18' may comprise a regenerable scrubbing process, which may involve recovering or capturing $SO_2$ and/or other acid gases for recycle within the process or for other use. '18' may comprise a non-regenerable scrubbing process, which may involve production and disposal of, for example, salts comprising $SO_2$. |
| 19 | $SO_2$ ultra-lean flue gas stream. '19' may be vented. '19' may undergo additional treatment. '19' may undergo, for example, flue gas $CO_2$ capture. Although flue gas $CO_2$ capture is feasible, in the present invention, the total $CO_2$ in flue gas emissions may be substantially lower than the total $CO_2$ captured in other process steps (for example, the captured $CO_2$ in '34') |
| 20 | '20' may comprise an input of a $CO_2$ containing salt or a salt comprising $CO_2$. For example, '20' may comprise calcium carbonate input. |
| 21 | '21' may comprise a reactor or mixing apparatus. '21' may be employed to react a salt comprising $CO_2$ (such as calcium carbonate) with a recoverable acid gas or a solution comprising a recoverable acid gas (such as aqueous sulfur dioxide). '21' may involve the generation of high partial pressure 'captured' carbon dioxide, which may be generated during a reaction of a salt comprising $CO_2$ (such as calcium carbonate) with a recoverable acid gas or a solution comprising a recoverable acid gas (such as aqueous sulfur dioxide). The headspace of '21' may comprise $CO_2$. It may be desirable for the headspace of '21' to contain a high concentration of $CO_2$ or comprise almost entirely $CO_2$ and/or water vapor and/or acid gas vapor pressure to, for example, minimize downstream processing of captured $CO_2$. '21' may operate in a continuous, semi-batch, or batch or combination thereof configuration. |
| 22 | '22' may comprise a mixture of acid-gas rich salt and a fluid. For example, '22' may comprise a mixture of solid calcium sulfite and water, which may comprise a solid-liquid mixture. '22' may comprise some reactions which have not reached full yield or may be designed to be in excess or stoichiometric excess. For example, '22' may comprise calcium carbonate and/or sulfur dioxide and/or aqueous sulfur dioxide. |
| 23 | '23' may comprise a fluid - solid separation device. For example, '23' may comprise a liquid-solid separation device or a gas-solid separation device or a liquid-gas separation device or a combination thereof. For example, '23' may comprise, including, but not limited to, one or more or a combination of the following: a filter, a rotary filter, a centrifuge, a decanter, or a sedimentation separator. '23' may involve separating solid salts, such as calcium sulfite and calcium carbonate, from water or remaining aqueous acid gas solution or acid gas or a combination thereof. |
| 24 | '24' may comprise separated solid. '24' may comprise separated calcium sulfite or calcium carbonate or a combination thereof. '24' may be transferred to one or more steps involving pre-treatment, pre-heating, or calcination or thermal decomposition. For example, '24' may undergo drying or further drying before or during or after |

Example FIG. 1 Key

| # | Process Element Descriptions |
|---|---|
| | entering '12'. It may be desirable for said drying, if any, to involve minimal or no contact with diatomic oxygen to, for example, prevent the oxidation of sulfite to sulfate. For example, said drying may comprise, including, but not limited to, one or more or a combination of the following: desiccants, or dry carrier gas, or warm carrier gas, or heated carrier gas, or centrifugation, or heating. |
| 25 | '25' may comprise pre-heated solid salt, which may comprise at least a portion a salt comprising acid gas. For example, '25' may comprise a pre-heated solid comprising calcium sulfite. '25' may comprise pre-heated solid undergoing transferring to a calcination or thermal decomposition or cement production reaction or oxide salt formation reaction or gas formation reaction or a combination thereof step. |
| 26 | '26' may comprise a calcined product. For example, '26' may comprise calcium oxide, or Portland cement, or cement, or magnesium oxide or a combination thereof. '26' may be warm due to exiting a thermal decomposition or calcination process. '26' may be lean or contain a substantially lower concentration of sulfur dioxide or acid gas or recoverable acid or carbon dioxide or a combination thereof than '25'. '26' may contain residual sulfite or sulfate or other sulfur or acid gas or may contain residual carbon dioxide salts or a combination thereof. |
| 27 | '27' may comprise cooled calcined product. '27' may exit the process and may be sold or otherwise utilized. '27' may undergo further treatment if desired. |
| 28 | '28' may comprise acid gas lean or sulfur dioxide lean water or solution. '28' may be transferred to '16' for absorption or bulk absorption of acid gas or sulfur dioxide. '28' may be cooled before being contacted with acid gases or before entering '16'. Said cooling may involve recovering heat from '28', which may include, but is not limited to, process heating, space heating, or other applications for heat. Said cooling may involve a chiller or chilled water or air cooling or wet surface contact cooling or other cooling methods or a combination thereof or one or more or a combination of processes for cooling. |
| 29 | '29' may comprise an acid gas rich or sulfur dioxide rich water or solution. '29' may comprise a sulfur dioxide rich solution resulting from the absorption of sulfur dioxide into water in an absorption column or gas-liquid contactor. '29' may comprise an acid gas rich solution. |
| 30 | '30' may comprise sulfur dioxide lean or other acid gas lean solution. '30' may be lean in sulfur dioxide due to the reaction of aqueous sulfur dioxide with calcium carbonate. If present embodiment is operating in a continuous or semi-continuous fashion, '30' may be lean in sulfur dioxide due to originating from or being transferred from a section or portion of '21' which may possess solution with the greatest or a greater average contact time with calcium carbonate or other salt comprising carbon dioxide. |
| 31 | '31' may comprise a solution or liquid phase separated following a solid-liquid separation step (for example: '23'). '31' may comprise a lean concentration of acid gas or dissolved $SO_2$. '31' may comprise a middle concentration of acid gas or dissolved $SO_2$. '31' may be recirculated ('32') into a reactor or mixer and/or may be employed as a solution ('33') transferred or mixed with a solution to be employed as an absorption solution. The proportion of '31' recirculated relative to employed as an absorption solution may be dependent on the relative concentration of dissolved acid gas in '31', which may be monitored or measured with, for example, one or more or a combination of monitoring or measuring devices. |
| 32 | '32' may comprise '31' undergoing recirculation to a reactor or mixing vessel. |
| 33 | '33' may comprise '31' being transferred as a portion of an absorption solution. It may be desirable to mix '33' with '30'. Alternatively, or additionally, '33' may be transferred directly an absorption column ('16'), wherein '33' may enter or may be fed into the absorption column at a different point than '30' or '28'. For example, if '33' possesses a greater concentration of acid gas or $SO_2$ than '28' or '30', it may be desirable to add '33' to an absorption column at a lower height or lower point in the absorption column. For example, it may be desirable to add '33' at a point in the absorption column where the concentration of dissolved acid gas in the absorption solution may be similar to the concentration of dissolved acid gas in '33'. |
| 34 | '34' may comprise a gas stream exiting a reactor or mixer, '21'. '34' may comprise relatively high-pressure $CO_2$ or a gas stream comprising $CO_2$. If desirable, '34' may exit '21' at a relatively standard temperature and with a relatively low partial pressure of water vapor and/or other non-$CO_2$. |
| 35 | '35' may comprise a compression and/or treatment step and/or liquification step. '35' may comprise a compression and/or water or other solvent vapor removal step and/or residual acid gas or $SO_2$ removal step and/or gas cooling step and/or gas heating step and/or gas liquification step and/or gas processing step. '37' may involve producing a supercritical fluid. |
| 36 | '36' may comprise a fluid stream being transferred to undergo further treatment, compression or use. '36' may comprise $CO_2$. |

-continued

| Example FIG. 1 Key | |
|---|---|
| # | Process Element Descriptions |
| 37 | '37' may comprise a compression and/or treatment and/or liquification step. '37' may comprise a compression and/or water or other solvent vapor removal step and/or residual acid gas or $SO_2$ removal step and/or gas cooling step and/or gas heating step and/or gas liquification step and/or gas processing step. '37' may involve producing a supercritical fluid. |
| 38 | '38' may comprise captured $CO_2$ under suitable conditions or at a suitable phase for, for example. transport, use, utilization, conversion, or storage. |

| Example FIG. 2 and FIG. 3 Key | |
|---|---|
| # | Process Element Descriptions |
| 1 | Pre-Cooled $SO_2$-Rich Flue Gas after Particulate Removal - '1' may comprise pre-cooled $SO_2$-Rich flue gas with at least a portion or most of the particulates removed. '1' may undergo additional cooling or treatment before entering the $SO_2$ absorption column or absorption step, '2'. '1' may undergo compression or pressurization before or while entering the absorption column or absorption step, '2'. |
| 2 | $SO_2$ Absorption Column - '2' may comprise an absorption column or contactor which facilitates the absorption of $SO_2$ from $SO_2$-Rich Flue Gas ('1') into an $SO_2$-Lean solution ('30'), forming an $SO_2$ - rich solution ('6') and a $SO_2$-Lean Flue Gas Stream ('3'). It may be desirable for '2' to selectively absorb $SO_2$, while minimally absorbing $CO_2$. Water or solvent scrubbing may be employed to selectively absorb $SO_2$, while, for example, minimally absorbing $CO_2$ due to the significantly greater solubility of $SO_2$ in water or other solvent than $CO_2$. |
| 3 | $SO_2$-Lean Flue Gas after $SO_2$ Absorption - '3' may comprise $SO_2$-Lean flue gas following the absorption of $SO_2$ in '2'. '3' may undergo additional treatment before exiting the process, '4'. |
| 4 | $SO_2$ Scrubbing and/or Other Further Treatment - '4' may comprise a $SO_2$ scrubbing step to remove most of or practically all the remaining or residual $SO_2$ in '3', which may result in an $SO_2$ ultra-lean flue gas stream, '5'. '4' may involve a scrubbing process which selectively absorbs dilute concentrations of $SO_2$, while minimally absorbing $CO_2$. For example, the absorption solution may comprise a bicarbonate, or carbonate, or carbamate, or combination thereof salt or a mixture of salts. For example, the absorbent and/or adsorbent may comprise one or more absorbents and/or adsorbents known in the art for removing $SO_2$ and/or other acid gases from flue gas streams or gas streams. '4' may comprise a regenerable scrubbing process, which may involve recovering or capturing $SO_2$ and/or other acid gases for recycle within the process or for other use. '4' may comprise a non-regenerable scrubbing process, which may involve production and disposal of, for example, salts or chemicals comprising or deriving from $SO_2$. |
| 5 | $SO_2$ ultra-lean flue gas stream. '5' may be vented. '5' may undergo additional treatment. '5' may undergo, for example, flue gas $CO_2$ capture. Although flue gas $CO_2$ capture is feasible, in the present invention, the total $CO_2$ in flue gas emissions may be substantially lower than the total $CO_2$ captured in other process steps (for example, the captured $CO_2$ in '23'). |
| 6 | '6' may comprise an acid gas rich or sulfur dioxide rich water or solution. '6' may comprise a sulfur dioxide rich solution resulting from the absorption of sulfur dioxide into water in an absorption column or gas-liquid contactor. '6' may comprise an acid gas rich solution. |
| 7 | '7' may comprise a multidirectional valve. '7' may direct the flow of the sulfur dioxide rich solution, '6', to the appropriate reactor. The sulfur dioxide rich solution may be directed to an appropriate reactor which may be at a stage in the batch or semi-batch sequence which involves the addition of sulfur dioxide rich solution. The appropriate reactor may change depending on the batch or semi-batch reaction stages and reaction sequence and each reactor's stage in the sequence. |
| 8 | '8' may comprise sulfur dioxide rich solution directed to the first reactor. |
| 9 | '9' may comprise a valve or redundant valve or a flow control valve or a pressure control valve or a pump or a combination thereof. |
| 10 | '10' may comprise sulfur dioxide rich solution directed to the first reactor. |
| 11 | '11' may comprise an input of a $CO_2$ containing salt or a salt comprising $CO_2$. For example, '11' may comprise calcium carbonate input. |
| 12 | '12' may comprise a multidirectional solid transfer valve or solid flow control or solid flow director. '12' may direct the flow of the carbon dioxide salt, such as calcium carbonate, to the appropriate reactor. The carbon dioxide salt, such as calcium carbonate, may be directed to an appropriate reactor which is at a stage in the batch or semi-batch sequence which involves the addition of carbon dioxide salt. The appropriate reactor may change depending on the batch or semi-batch reaction stages and reaction sequence and each reactor's stage in the sequence. |
| 13 | '13' may comprise carbon dioxide salt directed to the first reactor. |
| 14 | '14' may comprise a valve or redundant valve or a flow control valve or a pressure control valve or a pump or a conveyer belt or a combination thereof. |
| 15 | '15' may comprise carbon dioxide salt directed to the first reactor. |

-continued

Example FIG. 2 and FIG. 3 Key

| # | Process Element Descriptions |
|---|---|
| 16 | '16' may comprise a reactor or mixing apparatus. '16' may be employed to react a salt comprising $CO_2$, such as calcium carbonate, with a recoverable acid gas or a solution comprising a recoverable acid gas, such as aqueous sulfur dioxide. '16' may involve the generation of high partial pressure 'captured' carbon dioxide, which may be generated during a reaction of a salt comprising $CO_2$, such as calcium carbonate, with a recoverable acid gas or a solution comprising a recoverable acid gas, such as aqueous sulfur dioxide. The headspace of '16' may comprise $CO_2$. It may be desirable for the headspace of '16' to contain a high concentration of $CO_2$ or comprise almost entirely $CO_2$ and/or water vapor and/or physical solvent vapor and/or acid gas vapor pressure to, for example, minimize downstream processing of captured $CO_2$. '16' may operate in a semi-batch, or batch or combination thereof configuration. |
| 17 | '17' may comprise a gas stream exiting a reactor or mixer, '16'. '17' may comprise relatively high-pressure $CO_2$ or a gas stream comprising $CO_2$. If desirable, '17' may exit '16' at a relatively standard temperature and with a relatively low partial pressure of water vapor and/or other non-$CO_2$. |
| 18 | '18' may comprise a multidirectional valve. '18' may direct a gas stream comprising $CO_2$ from one or more reactors to $CO_2$ processing, treatment, compression, transportation, utilization, and/or conversion steps. '18' may control the flow of gas streams or gas streams comprising $CO_2$, including, for example, ensuring gas streams achieve the appropriate specifications or the reactor is at the appropriate stage or a combination thereof before or while directing one or more gas streams comprising $CO_2$. |
| 19 | '19' may comprise a gas stream comprising $CO_2$ directed by '18' to one or more or a combination of $CO_2$ processing, treatment, compression, transportation, utilization, and/or conversion steps. |
| 20 | '20' may comprise a compression and/or treatment step and/or liquification step. '20' may comprise a compression and/or water or solvent removal step and/or residual acid gas or $SO_2$ removal step and/or gas cooling step and/or gas heating step and/or gas liquification step and/or gas processing step. '20' may involve producing a supercritical fluid. |
| 21 | '21' may comprise a fluid stream being transferred to undergo further treatment, compression or use. '21' may comprise $CO_2$. |
| 22 | '22' may comprise a compression and/or treatment and/or liquification step. '22' may comprise a compression and/or water or solvent removal step and/or residual acid gas or $SO_2$ removal step and/or cooling step and/or heating step and/or liquification step and/or processing step. '22' may involve producing a supercritical fluid. |
| 23 | '23' may comprise captured $CO_2$ under suitable conditions or at a suitable phase for, for example. transport, use, utilization, conversion, or storage. |
| 24 | '24' may comprise a mixture of acid-gas rich salt and a fluid. For example, '22' may comprise a mixture of solid calcium sulfite and water and/or physical solvent, which may comprise a solid-liquid mixture. '24' may comprise some reagents which have not reached full yield or may be designed to be in excess or stoichiometric excess. For example, '24' may comprise a portion calcium carbonate and/or sulfur dioxide and/or sulfur dioxide solution. |
| 25 | '25' may comprise a fluid - solid separation device. For example, '25' may comprise a liquid-solid separation device or a gas-solid separation device or a liquid-gas separation device or a combination thereof. For example, '25' may comprise, including, but not limited to, one or more or a combination of the following: a filter, a rotary filter, a centrifuge, a decanter, or a sedimentation separator. '25' may involve separating solid salts, such as calcium sulfite and calcium carbonate, from water or remaining acid gas solution or acid gas or a combination thereof. |
| 26 | '26' may comprise a solution or liquid phase separated following a solid-liquid separation step (for example: '25'). '26' may comprise a lean concentration of acid gas or $SO_2$ solution. '26' may be lean in sulfur dioxide due to the reaction of sulfur dioxide with calcium carbonate. |
| 27 | '27' may comprise a valve or redundant valve or a flow control valve or a pressure control valve or a pump or a combination thereof. |
| 28 | '28' may comprise sulfur dioxide lean or other acid gas lean solution. |
| 29 | '29' may comprise a multidirectional valve. '29' may direct the flow of the sulfur dioxide lean solution to the sulfur dioxide absorption column or contactor, '2'. |
| 30 | '30' may comprise acid gas lean or sulfur dioxide lean water or solution. '30' may be transferred to '2' for absorption or bulk absorption of acid gas or sulfur dioxide. '30' may be cooled before being contacted with acid gases or before entering '2'. Said cooling may involve recovering heat from '30', which may include, but is not limited to, process heating, space heating, or other applications for heat. Said cooling may involve a chiller or chilled water or air cooling or wet surface contact cooling or other cooling methods or a combination thereof or one or more or a combination of processes for cooling. |
| 31 | '31' may comprise separated solid. '31' may comprise separated calcium sulfite or calcium carbonate or a combination thereof. |

-continued

Example FIG. 2 and FIG. 3 Key

| # | Process Element Descriptions |
|---|---|
| 32 | '32' may comprise a valve or redundant valve or a flow control valve or a pressure control valve or a pump or a conveyer belt or a combination thereof. |
| 33 | '33' may comprise separated solid. '33' may comprise separated calcium sulfite or calcium carbonate or a combination thereof. |
| 34 | '34' may comprise a multidirectional solid transfer valve or solid flow control or solid flow director. '34' may direct the flow of the separated acid gas salt or regenerable acid gas salt, such as calcium sulfite, subsequent treatment steps and/or thermal decomposition or calcination step. |
| 35 | '35' may comprise separated solid. '35' may comprise separated calcium sulfite or calcium carbonate or a combination thereof. '35' may be transferred to one or more steps involving pre-treatment, pre-heating, or calcination or thermal decomposition. For example, '35' may undergo drying or further drying before or during or after entering '79'. It may be desirable for said drying, if any, to involve minimal or no contact with diatomic oxygen to, for example, prevent the oxidation of sulfite to sulfate. For example, said drying may comprise, including, but not limited to, one or more or a combination of the following: desiccants, or dry carrier gas, or warm carrier gas, or heated carrier gas, or centrifugation, or heating. |
| 36 | '36' may comprise sulfur dioxide rich solution directed to the second reactor. |
| 37 | '37' may comprise a valve or redundant valve or a flow control valve or a pressure control valve or a pump or a combination thereof. |
| 38 | '38' may comprise sulfur dioxide rich solution directed to the second reactor. |
| 39 | '39' may comprise a reactor or mixing apparatus. '39' may be employed to react a salt comprising $CO_2$, such as calcium carbonate, with a recoverable acid gas or a solution comprising a recoverable acid gas, such as aqueous sulfur dioxide or sulfur dioxide dissolved in a physical solvent. '39' may involve the generation of high partial pressure 'captured' carbon dioxide, which may be generated during a reaction of a salt comprising $CO_2$, such as calcium carbonate, with a recoverable acid gas or a solution comprising a recoverable acid gas. The headspace of '39' may comprise $CO_2$. It may be desirable for the headspace of '39' to contain a high concentration of $CO_2$ or comprise almost entirely $CO_2$ and/or water vapor or solvent vapor and/or acid gas vapor pressure to, for example, minimize downstream processing of captured $CO_2$. '39' may operate in a semi-batch, or batch or combination thereof configuration. |
| 40 | '40' may comprise carbon dioxide salt directed to the second reactor. |
| 41 | '41' may comprise a valve or redundant valve or a flow control valve or a pressure control valve or a pump or a conveyer belt or a combination thereof. |
| 42 | '42' may comprise carbon dioxide salt directed to the third reactor. |
| 43 | '43' may comprise a gas stream exiting a reactor or mixer, '39'. '43' may comprise relatively high-pressure $CO_2$ or a gas stream comprising $CO_2$. If desirable, '43' may exit '39' at a relatively standard temperature and with a relatively low partial pressure of water vapor and/or other non-$CO_2$ contaminants. |
| 44 | '44' may comprise a mixture of acid-gas rich salt and a fluid. For example, '44' may comprise a mixture of solid calcium sulfite and water, which may comprise a solid-liquid mixture. '44' may comprise some reagents which have not reached full yield or may be designed to be in excess or stoichiometric excess. For example, '44' may comprise a portion calcium carbonate and/or sulfur dioxide and/or sulfur dioxide solution. |
| 45 | '45' may comprise a fluid - solid separation device. For example, '45' may comprise a liquid-solid separation device or a gas-solid separation device or a liquid-gas separation device or a combination thereof. For example, '45' may comprise, including, but not limited to, one or more or a combination of the following: a filter, a rotary filter, a centrifuge, a decanter, or a sedimentation separator. '45' may involve separating solid salts, such as calcium sulfite and calcium carbonate, from water or solvent or remaining acid gas solution or acid gas or a combination thereof. |
| 46 | '46' may comprise a solution or liquid phase separated following a solid-liquid separation step (for example: '45'). '46' may comprise a lean concentration of acid gas or aqueous $SO_2$ or SO2 solution. '46' may be lean in sulfur dioxide due to the reaction of sulfur dioxide with calcium carbonate. |
| 47 | '47' may comprise a valve or redundant valve or a flow control valve or a pressure control valve or a pump or a combination thereof. |
| 48 | '48' may comprise sulfur dioxide lean or other acid gas lean solution. |
| 49 | '49' may comprise separated solid. '49' may comprise separated calcium sulfite or calcium carbonate or a combination thereof. |
| 50 | '50' may comprise a valve or redundant valve or a flow control valve or a pressure control valve or a pump or a conveyer belt or a combination thereof. |
| 51 | '51' may comprise separated solid. '51' may comprise separated calcium sulfite or calcium carbonate or a combination thereof. |
| 52 | '52' may comprise sulfur dioxide rich solution directed to the third reactor. |
| 53 | '53' may comprise a valve or redundant valve or a flow control valve or a pressure control valve or a pump or a combination thereof. |
| 54 | '54' may comprise sulfur dioxide rich solution directed to the third reactor. |
| 55 | '55' may comprise a reactor or mixing apparatus. '55' may be employed to react a salt comprising $CO_2$, such as calcium carbonate, with a recoverable acid gas or a solution comprising a recoverable acid gas. '55' may involve the generation of high partial pressure 'captured' carbon dioxide, which may be generated during a reaction |

Example FIG. 2 and FIG. 3 Key

| # | Process Element Descriptions |
|---|---|
| | of a salt comprising $CO_2$, such as calcium carbonate, with a recoverable acid gas or a solution comprising a recoverable acid gas. The headspace of '55' may comprise $CO_2$. It may be desirable for the headspace of '55' to contain a high concentration of $CO_2$ or comprise almost entirely $CO_2$ and/or water vapor or solvent vapor and/or acid gas vapor pressure to, for example, minimize downstream processing of captured $CO_2$. '55' may operate in a semi-batch, or batch or combination thereof configuration. |
| 56 | '40' may comprise carbon dioxide salt directed to the third reactor. |
| 57 | '41' may comprise a valve or redundant valve or a flow control valve or a pressure control valve or a pump or a conveyer belt or a combination thereof. |
| 58 | '42' may comprise carbon dioxide salt directed to the third reactor. |
| 59 | '59' may comprise a gas stream exiting a reactor or mixer, '55'. '59' may comprise relatively high-pressure $CO_2$ or a gas stream comprising $CO_2$. If desirable, '59' may exit '55' at a relatively standard temperature and with a relatively low partial pressure of water vapor and/or solvent vapor and/or other non-$CO_2$. |
| 60 | '60' may comprise a mixture of acid-gas rich salt and a fluid. For example, '60' may comprise a mixture of solid calcium sulfite and water or solvent, which may comprise a solid-liquid mixture. '60' may comprise some reagents which have not reached full yield or may be designed to be in excess or stoichiometric excess. For example, '60' may comprise a portion calcium carbonate and/or sulfur dioxide and/or sulfur dioxide solution. |
| 61 | '61' may comprise a fluid - solid separation device. For example, '61' may comprise a liquid-solid separation device or a gas-solid separation device or a liquid-gas separation device or a combination thereof. For example, '61' may comprise, including, but not limited to, one or more or a combination of the following: a filter, a rotary filter, a centrifuge, a decanter, or a sedimentation separator. '61' may involve separating solid salts, such as calcium sulfite and calcium carbonate, from water or solvent or remaining acid gas solution or acid gas or a combination thereof. |
| 62 | '62' may comprise a solution or liquid phase separated following a solid-liquid separation step (for example: '61'). '62' may comprise a lean concentration of acid gas or dissolved $SO_2$. '62' may be lean in sulfur dioxide due to the reaction of aqueous sulfur dioxide with calcium carbonate. |
| 63 | '63' may comprise a valve or redundant valve or a flow control valve or a pressure control valve or a pump or a combination thereof. |
| 64 | '64' may comprise sulfur dioxide lean or other acid gas lean solution. |
| 65 | '65' may comprise separated solid. '65' may comprise separated calcium sulfite or calcium carbonate or a combination thereof. |
| 66 | '66' may comprise a valve or redundant valve or a flow control valve or a pressure control valve or a pump or a conveyer belt or a combination thereof. |
| 67 | '67' may comprise separated solid. '67' may comprise separated calcium sulfite or calcium carbonate or a combination thereof. |
| 68 | Air Input - Air or other gas comprising at least a portion oxygen. |
| 69 | Gas Blower or Air Blower or Other Air Pump - Pump or Fan or Blower to pressurize or transfer or a combination thereof air or other gas comprising at least a portion oxygen into the system. |
| 70 | Air Post '69' - Air or other gas comprising at least a portion oxygen after the gas blower. The temperature of '70' may be similar to the temperature of the air source or the surrounding outside air temperature. The temperature of '70' may be less than the temperature of '72'. |
| 71 | Heat Exchanger or Contact Heat Exchanger or Lime Cooler- '70', which may comprise air, may be heat exchanged with hot CaO or cement ('83'), which may result in pre-heated air and cooled CaO or cement. '70' may be directly contacted with the CaO or cement, cooling the CaO or cement, while heating the air. If the air or other oxygen containing gas is in direct contact with CaO or cement, it may be desirable to prevent the air or other oxygen containing gas from entering '77' or other environment potentially containing sulfur oxides or recoverable sulfur oxides to prevent, for example, oxidation of $SO_2$ and/or sulfite into $SO_3$ and/or sulfate during, for example, thermal decomposition steps. Alternatively, or additionally, '70' may be indirectly contacted or heat exchanged with the CaO or cement, cooling the CaO or cement, while heating the air. |
| 72 | Pre-Heated Air - Air which may have been preheated by in '71'. '72' may comprise air fed into the combustion or fuel burning process. |
| 73 | Carbonaceous Fuel Input - A fuel comprising carbon ('73') may be fed or injected into a fuel firing or combustion step ('75'). Carbonaceous fuel may include, but is not limited to, natural gas, coal, pulverized coal, biomass, charcoal, oil, diesel, gasoline, kerosene, LPG, ethane, propane, butane, or a combination thereof. In some embodiments, it may be desirable to burn the carbonaceous fuel ('73') and/or sulfurous fuel ('74') at a ratio with oxygen such that minimal non-reacted oxygen or diatomic oxygen is present in post combustion gases (post-combustion gases may include, but are not limited to, '76'). |
| 74 | Sulfurous Fuel Input - A fuel comprising sulfur ('74') may be fed or injected into a fuel firing or combustion step ('75'). Sulfurous fuel may include, but is not limited to, sulfur, elemental sulfur, sour gas, hydrogen sulfide, sulfur dioxide, sulfur monoxide, ammonium sulfate, ammonium sulfite, or a combination thereof. In some embodiments, it may be desirable to burn the sulfurous fuel ('74') and/or |

Example FIG. 2 and FIG. 3 Key

| # | Process Element Descriptions |
|---|---|
| | carbonaceous ('73') at a ratio with oxygen such that minimal non-reacted oxygen or diatomic oxygen is present in post combustion gases (for example - '76'). Sulfurous fuel may be employed to reduce the concentration of oxygen in the combustion gases. Sulfurous fuel may be employed to reduce the concentration of oxygen in the combustion gases instead of rich carbonaceous fuel - air ratios, preventing or minimizing incomplete combustion and/or the formation of carbon monoxide. Sulfurous fuel may be employed to as a make-up for sulfur dioxide losses. Alternatively, or additionally, a nitrogenous fuel, such as ammonia or an ammonia salt or an ammonia derivative, may be employed introduced or combusted in '74'. |
| 75 | Combustion chamber or Firing Fan - A chamber or step for combusting fuel to generate high temperature gases for the calcination or thermal decomposition process. '75' may be designed or optimized to minimize the concentration of oxygen in the combustion gases exiting '75' and/or optimize combustion efficiency. |
| 76 | Input Hot Combustion Gases, $SO_2$-Lean - '76' may comprise the hot combustion gases exiting '75' and entering the calcination step or kiln or rotating kiln '77' . Although '76' may contain sulfurous gases, such as sulfur dioxide, the concentration of the sulfurous gases in '76' may desirably be lower than the concentration of sulfurous gases in the gases exiting the kiln, '78'. '76' may possess minimal or ultra-low concentrations of diatomic oxygen to prevent or minimize the formation of sulfates and other practically permanent sulfur compounds or salts or further oxidized sulfur compounds. |
| 77 | Calcination Step or Kiln or Rotating Kiln - '77' may comprise a kiln for the thermal decomposition of acid gas salts into 'acid-gas' and oxide salt or cement. For example, '77' may comprise a kiln which may be employed in the present invention for the thermal decomposition of calcium sulfite into sulfur dioxide and calcium oxide or cement. '77' may comprise a rotating kiln or other kiln. Applicable kilns may include, but are not limited to, kilns employed in the art for the calcination of limestone, or calcination of calcium carbonate, or the production of cement, or a combination thereof. Calcium sulfite may be fed into the kiln and thermally decomposed into at least a portion of sulfur dioxide and calcium oxide or cement using heat from, for example, hot combustion gases, '76', which may be directly passed through or over or in direct contact with said calcium sulfite. Warm calcium oxide or cement, '83', and $SO_2$-Rich flue gases or combustion gases, '78', may comprise outputs of '77'. |
| 78 | Hot Flue Gases, $SO_2$-Rich - '78' may comprise the hot flue gases exiting the kiln, '77'. '78' may comprise a relatively high concentration of $SO_2$ due to, for example, the thermal decomposition or calcination of calcium sulfite in the kiln, '77', and/or $SO_2$ present in the Input Hot Combustion Gases, '76'. At least a portion or all of said 'SO2', may be recovered, recycled internally, and/or removed from the gases in '78' in subsequent steps, which may be before at least a portion of the gases in '78' exit the process or are vented. '78' may also comprise particulates which may require separation or removal from the gas stream in subsequent steps. |
| 79 | Heat Exchanger or Contact Heat Exchanger or Calcium Sulfite Pre-Heater - '78', which may comprise $SO_2$-Rich hot flue gases, may be heat exchanged with cold calcium sulfite ('35'), which may result in pre-cooled $SO_2$-Rich flue gases, '80', and pre-heated $CaSO_3$, '82'. $SO_2$-Rich hot flue gases may be directly contacted with the $CaSO_3$. The $SO_2$-Rich hot flue gases may be directly contacted with the CaS03, for example, because the S02-Rich hot flue gases may possess an ultra-low concentration of diatomic oxygen, which may prevent the $CaSO_3$ from oxidizing into a sulfate and/or may facilitate the heating and/or decomposition of $CaSO_3$. |
| 80 | Pre-Cooled $SO_2$-Rich Flue Gas - '80' may comprise pre-cooled $SO_2$-Rich flue gas, which may possess particulates which may need to be, at least in part, removed before the $SO_2$ absorption column, '2'. '80' may undergo additional cooling before or during '81'. An additional gas blower or compressor may be required to transfer '80', which may not be shown in a figure. |
| 81 | Particulate Remover or Baghouse or Electrostatic Precipitator, or Filter, or a combination thereof- '81' may comprise one or more or a combination of steps to remove particulate matter from '80'. |
| 82 | '82' may comprise pre-heated solid salt, which may comprise at least a portion a salt comprising acid gas. For example, '82' may comprise a pre-heated solid comprising calcium sulfite. '82' may comprise pre-heated solid undergoing transferring to a calcination or thermal decomposition or cement production reaction or oxide salt formation reaction or gas formation reaction or a combination thereof step. |
| 83 | '83' may comprise a calcined product. For example, '83' may comprise calcium oxide, or Portland cement, or cement or magnesium oxide or a combination thereof. '83' may be warm due to exiting a thermal decomposition or calcination process. '83' may be lean or contain a substantially lower concentration of sulfur dioxide or acid gas or recoverable acid or carbon dioxide or a combination thereof than '83'. '83' may contain residual sulfite or sulfate or other sulfur or acid gas or may contain residual carbon dioxide salts or a combination thereof. |

| # | Process Element Descriptions |
|---|---|
| 84 | '84' may comprise cooled calcined product. '84' may exit the process and may be sold or otherwise utilized. '84' may undergo further treatment if desired. Alternatively, or additionally, '84' may be employed to absorb $CO_2$ from the air or water or other gas or liquid stream comprising at least a portion $CO_2$ or acid gas. For example, '84' may be employed to capture $CO_2$ if, for example, the present invention comprises at least a portion of a $CO_2$ air capture system. |

Example FIG. 2 and FIG. 3 Key

Additional General Description

One or more or a combination of steps in the present invention may be conducted in same location or region if desired.

One or more or a combination of steps in the present invention may be conducted in separate locations if desired. For example, a captured carbon dioxide production step, which may comprise a reaction of calcium carbonate with sulfur dioxide to produce calcium sulfite and carbon dioxide, may be conducted in a separate location from the calcining step, which may comprise calcining calcium sulfite into calcium oxide and/or cement and sulfur dioxide. For example, a captured carbon dioxide production step may be conducted in or near a location or application requiring or consuming carbon dioxide, which may include, but is not limited to, one or more or a combination of the following: carbon dioxide enhanced oil recovery, carbon dioxide sequestration, carbon dioxide conversion into materials or chemicals, agriculture, carbon dioxide enhanced greenhouse, or carbon dioxide utilization. For example, the captured carbon dioxide production step may be conducted in or near a location with calcium carbonate or limestone feedstock. For example, the captured carbon dioxide production step may be conducted in or near a system which absorbs carbon dioxide from one or more sources of carbon dioxide, which may include, but is not limited to, air, and may absorb and/or convert said carbon dioxide into calcium carbonate. For example, the calcining step may be conducted in a location with access to a relatively inexpensive fuel, such as flare gas, sour gas, natural gas, or sulfurous fuels, or coal, or biomass, or biofuel, or hydrogen, or nuclear, or geothermal, or waste heat, or heat, or a combination thereof. For example, the calcining step may be conducted in a location with or near demand for the calcined products, which may include, but are not limited to, calcium oxide, calcium hydroxide, magnesium oxide, magnesium hydroxide, cement, sulfur dioxide, nitrogen oxide, or a combination thereof. For example, the acid gas recovery step may be co-located with locations with waste cold. For example, the acid gas recovery step may be co-located with a LNG gasification facility, where, for example, the cooling provided by the phase change of LNG to natural gas may facilitate the separation or recovery of sulfur dioxide or other acid gas.

Example embodiments wherein one or more or a combination of steps are conducted in separate locations may comprise, including, but not limited to:

For example, the carbon dioxide generation step may comprise multiple mixers or reactors, which may each be co-located with one or more or a group of applications consuming or using carbon dioxide. The calcining step and/or acid gas recovery step may be conducted in a centralized location.

For example, the carbon dioxide generation step may comprise multiple mixers or reactors, which may each be co-located with one or more or a group of oil wells requiring carbon dioxide enhanced oil recovery. The calcining step and/or acid gas recovery step may be conducted in a centralized location. Calcium carbonate may be supplied to the carbon dioxide generation step from one or more or a combination of sources, which may include, but is not limited to, mined calcium carbonate, limestone, carbon dioxide air capture, or other calcium carbonate source. Materials may be transferred between process steps. For example, calcium sulfite may be transferred from the carbon dioxide generation step to the calcining step, which may comprise air-tight transport, railcars, trucks, conveyor belt, or ship. For example, recovered sulfur dioxide may be transferred from the acid gas recovery step to the carbon dioxide generation step, which may comprise pipelines, air-tight transport, railcars, tank trucks, trucks, or ship. For example, SO2-rich solution and SO2-lean solution may be transferred between the acid gas recovery step and the carbon dioxide generation step.

If one or more steps are conducted in separate locations, one or more materials may be transferred between said separate locations.

One or more or a combination of steps of the present invention may be modular or transportable or a combination thereof. For example, the carbon dioxide generation step may comprise mobile reactors and/or other mobile or containerized structures. For example, the carbon dioxide generation step may be transported to a location requiring carbon dioxide. For example, if the location requiring carbon dioxide no longer needs carbon dioxide from the carbon dioxide generation step, said carbon dioxide generation step may be transported to a different location. For example, the calcination step and/or acid gas recovery step may comprise mobile calciners, or mobile absorption columns, or mobile separators, or other mobile or containerized structures, or a combination thereof. For example, the calcining step may be transported to locations with significant available low cost energy or an anticipated or temporary release of low cost energy, which may include, but is not limited to, natural gas releases, flare gas, sour gas, forest fire, geothermal events, lava, waste heat, or a combination thereof.

One or more or a combination of materials, reagents, products, inputs, outputs, or intermediates may be sourced, or used, or otherwise employed differently than described herein.

For example, calcium sulfite may comprise a byproduct or salable product, and may comprise an output of the present invention.

For example, sulfur dioxide may comprise a virgin material input, rather than or in addition to a regenerated intermediate.

For example, sulfur dioxide may be converted into elemental sulfur using, for example, the Claus process.

For example, sulfur dioxide may be converted into sulfuric acid.

For example, sulfur dioxide or sulfur or a combination thereof may be transported to the carbon dioxide generation step.

For example, virgin sulfur dioxide or virgin sulfur or virgin hydrogen sulfide or a combination thereof may be transported to the carbon dioxide generation step and/or directly added to the carbon dioxide generation step. Virgin sulfur dioxide may be added to the carbon dioxide generation step or may be dissolved into a solution before said solution is added to the carbon dioxide generation step or a combination thereof. Virgin sulfur or virgin hydrogen sulfide may be combusted to produce virgin sulfur dioxide. Virgin sulfur dioxide may be employed to makeup for sulfur dioxide losses (which may also be referred to as sulfur losses) in the process. Sulfur dioxide losses may include, but are not limited to, sulfur dioxide consumed or absorbed during the calcining step, or residual sulfur dioxide in flue gases following one or more treatment steps, or residual sulfur dioxide in flue gases which may be uneconomical to fully regenerate, or sulfur dioxide converted to one or more other compounds which may not be economically regenerable, sulfur dioxide converted to one or more products, or a combination thereof.

Some embodiments of the present invention may be constructed or implemented by retrofitting a pre-existing calciner for cement production and/or calcium oxide production to operate with input comprising calcium sulfite, rather than, or in addition to, calcium carbonate or limestone.

Some pre-existing calciners comprise materials compatible with CaSO3 and/or SO2 and/or other regenerable acid gas or regenerable acid gas salt. Some pre-existing calciners may require one or more or a combination of components to be replaced or coated to ensure material compatibility with CaSO3 and/or SO2.

Some pre-existing calciners may be retrofitted with systems or materials to ensure lower diatomic oxygen concentration in the calciner or in the input feeder or in the pulverizer or a combination thereof A richer fuel to air ratio may be employed minimize diatomic oxygen concentration or amounts in the calciner. Due to a richer fuel mixture, some embodiments may require systems for removing or eliminating or converting incomplete combustion products (for example: carbon monoxide (CO) and VOCs). Said systems for removing or eliminating incomplete combustion products may include, but are not limited to, systems for further oxidizing the incomplete combustion products, catalytic converters, or systems for creating valuable products or chemicals or fuels from incomplete combustion products.

Some pre-existing calciners may be retrofitted with systems or materials to minimize the amount of air or other gases comprising diatomic oxygen enter the calciner. For example, improved seals and/or improved flow control may be implemented.

The fuel combustion step or system may be modified or replaced to enable combustion of carbonaceous fuel, and/or sulfurous fuel, and/or nitrogenous fuel and/or hydrogen fuel. For example, the fuel combustion system may modified or replaced to enable one or more combustion steps. For example, the fuel combustion step or system may modified or replaced to enable one or more combustion steps, wherein each combustion step may decrease the concentration or amount of diatomic oxygen.

The carbon dioxide generation step, the acid gas recovery step, other process elements, or a combination thereof may be added or installed in a retrofit system.

The present invention may comprise a gas separation technology. For example, the present invention may be employed to regenerate an oxide with affinity for carbon dioxide from carbon dioxide salt. For example, the present invention may be employed to regenerate an oxide with affinity for carbon dioxide from carbon dioxide salt as part of a system for capturing CO2 from air or water or other potentially dilute CO2 stream. For example, the present invention may be employed to regenerate an oxide with affinity for carbon dioxide from a carbon dioxide salt as part of a system for removing carbon dioxide from sodium carbonate or potassium carbonate or other alkali-carbonate. For example, the present invention may be employed to regenerate an alkaline-earth oxide with affinity for carbon dioxide from an alkaline-earth carbonate as part of a system for regenerating an alkali-metal oxide or carbonate from an alkali-metal carbonate, sesquicarbonate, or bicarbonate.

For example, in an example CO2 air capture embodiment:
1. CO2 may be absorbed from air or water into a CO2-Lean alkali solution (for example: a solution comprising lithium or sodium or potassium or ammonia or amine), forming a CO2-Rich alkali solution. Said CO2-Lean alkali solution may comprise an alkali oxide solution. Said CO2-Lean alkali solution may comprise a carbonate solution. Said CO2-Rich alkali solution may comprise a carbonate or sesquicarbonate or bicarbonate solution. Said CO2-Rich alkali solution may comprise a greater concentration of CO2 or greater molar ratio of CO2 to alkali than said CO2-Lean alkali solution.
2. Said CO2-Rich alkali solution may be contacted with a CO2-Lean alkaline-earth solid, which may result in the formation of a CO2-Lean alkali solution and a CO2-Rich alkaline-earth solid. Said CO2-Rich alkaline-earth solid may comprise alkaline-earth carbonate. Said CO2-Lean alkaline-earth solid may comprise alkaline-earth oxide. Said CO2-Rich alkaline-earth solid may comprise a greater concentration of CO2 or greater molar ratio of CO2 to alkali than said CO2-Lean alkaline-earth solid. Said CO2-Lean alkali solution may be transferred to step 1. Said CO2-Rich alkaline-earth solid may be transferred to step 3.
3. Said CO2-Rich alkaline-earth solid may be converted into a CO2-Lean alkaline-earth solid using one or more or a combination of systems or methods described herein. Said CO2-Lean alkaline-earth solid may be transferred to step 2.

The present invention may enable the capture of carbon dioxide from air or water with, including, but not limited to, one or more or a combination of the following:

Reagents comprising an alkali, or an alkaline-earth, or a combination thereof

The generation of captured carbon dioxide comprising a high purity of gaseous carbon dioxide The generation of captured carbon dioxide comprising a low concentration of water vapor or solvent vapor The generation of captured carbon dioxide at a high pressure of carbon dioxide The generation of captured carbon dioxide at mild temperatures The generation of captured carbon dioxide, wherein the regeneration process is separate from the CO2 generation step and may involve the regeneration of an acid gas other than CO2.

Fuel in the process may be combusted in air and/or heat transferred into the thermal regeneration or thermal decomposition step comprises hot combustion gases A CO2 air capture technology involving calcination without the need for an air separation unit or an oxy-combustion unit or a CO2 atmosphere calcination environment The generation of captured carbon dioxide without the need for an air separation unit or an oxy-combustion unit

EXAMPLE EXEMPLARY EMBODIMENTS AND SUB-EMBODIMENTS

Example Exemplary Embodiments

A process for producing captured carbon dioxide comprising:
  Reacting a carbonate salt with a regenerable acid gas to produce a cation-regenerable acid gas salt and gaseous carbon dioxide;
  Thermally decomposing said cation-regenerable acid gas salt to produce cement, an oxide, or a combination thereof.

A process for producing captured carbon dioxide comprising:
  Reacting a carbonate salt with a regenerable acid gas to produce a cation-regenerable acid gas salt and gaseous carbon dioxide;
  Thermally decomposing said cation-regenerable acid gas salt to produce cement, an oxide, regenerable acid gas, or a combination thereof.

A process for producing captured carbon dioxide comprising:
  Reacting a carbonate salt with sulfur dioxide to produce a sulfite salt and gaseous carbon dioxide;
  Thermally decomposing said sulfite salt to produce cement, an oxide, or a combination thereof.

A process for producing captured carbon dioxide comprising:
  Reacting a carbonate salt with sulfur dioxide-rich aqueous solution to produce a sulfite salt, gaseous carbon dioxide, and sulfur dioxide-lean aqueous solution;
  Separating said sulfite salt from said sulfur dioxide-lean aqueous solution;
  Thermally decomposing said separated sulfite salt to produce cement, an oxide, or a combination thereof.

A process for producing cement or calcium oxide or CO2-lean alkaline earth carbonate and captured carbon dioxide comprising:
  Reacting solid calcium carbonate with sulfur dioxide-rich aqueous solution to produce calcium sulfite, gaseous carbon dioxide, and sulfur dioxide-lean aqueous solution;
  Separating said solid calcium sulfite from said sulfur dioxide-lean aqueous solution;
  Thermally decomposing said separated calcium sulfite to produce calcium oxide, cement, or a combination thereof.

A process for producing captured carbon dioxide comprising:
  Reacting solid magnesium carbonate with sulfur dioxide-rich aqueous solution to produce magnesium sulfite, gaseous carbon dioxide, and sulfur dioxide-lean aqueous solution;
  Separating said solid magnesium sulfite from said sulfur dioxide-lean aqueous solution;
  Thermally decomposing said separated magnesium sulfite to produce gaseous sulfur dioxide.

Example Exemplary Embodiments

1. A process for producing captured carbon dioxide comprising:
   Reacting solid calcium carbonate with sulfur dioxide-rich solution to produce calcium sulfite, gaseous carbon dioxide, and sulfur dioxide-lean solution;
   Separating said solid calcium sulfite from said sulfur dioxide-lean solution;
   Thermally decomposing said separated calcium sulfite to produce gaseous sulfur dioxide.
2. The process of exemplary embodiment 1 wherein said calcium sulfite is thermally decomposed to produce cement
3. The process of exemplary embodiment 1 wherein said calcium sulfite is thermally decomposed to produce calcium oxide
4. The process of exemplary embodiment 1 wherein said calcium sulfite is thermally decomposed in a mixture with calcium carbonate
5. The process of exemplary embodiment 1 wherein said calcium sulfite is thermally decomposed in a mixture comprising clay, or silicon dioxide, or aluminum oxide, or iron oxide, or iron carbonate, or magnesium carbonate, or magnesium oxide, or silicates, or aluminates, or shale, or sand, or fly ash, or ash, or slag, or sulfur oxides, or a combination thereof
6. The process of exemplary embodiment 1 wherein said calcium sulfite is thermally decomposed in a low oxygen environment
7. The process of exemplary embodiment 6 wherein said low oxygen environment comprises a concentration of gaseous diatomic oxygen of less than 20,000 PPM
8. The process of exemplary embodiment 6 wherein said low oxygen environment comprises a concentration of gaseous diatomic oxygen of less than 10,000 PPM
9. The process of exemplary embodiment 1 wherein said thermal decomposition is conducted in the presence of hot gases
10. The process of exemplary embodiment 9 wherein said hot gases comprise combustion gases
11. The process of exemplary embodiment 10 wherein said combustion gases originated from the combustion of a fuel-rich mixture
12. The process of exemplary embodiment 10 wherein said combustion gases originated from the combustion of fuel comprising carbonaceous fuel, sulfurous fuel, nitrogenous fuel, hydrogen fuel, or a combination thereof
13. The process of exemplary embodiment 10 wherein said combustion gases originated from a combustion process comprising a first combustion step and a second combustion step;
    Wherein the first combustion step comprises combusting carbonaceous fuel; and
    Wherein the second combustion step comprises combusting sulfurous fuel 14. The process of exemplary embodiment 13 wherein the second combustion step reduces the diatomic oxygen concentration
15. The process of exemplary embodiment 13 wherein the second combustion step provides makeup sulfur dioxide to makeup for sulfur dioxide losses in the process
16. The process of exemplary embodiment 10 wherein said combustion gases originated from a combustion process comprising a first combustion step and a second combustion step;
    Wherein the first combustion step comprises combusting carbonaceous fuel; and
    Wherein the second combustion step comprises combusting hydrogen fuel
17. The process of exemplary embodiment 10 wherein said combustion gases originated from a combustion process comprising a first combustion step and a second combustion step;
    Wherein the first combustion step comprises combusting hydrogen fuel; and
    Wherein the second combustion step comprises combusting sulfurous fuel
18. The process of exemplary embodiment 10 wherein said combustion gases originated from a combustion process comprising a first combustion step and a second combustion step;
    Wherein the first combustion step comprises combusting carbonaceous fuel; and
    Wherein the second combustion step comprises combusting nitrogenous fuel
19. The process of exemplary embodiment 10 wherein said combustion gases originated from a combustion process comprising a first combustion step and a second combustion step;
    Wherein the first combustion step comprises combusting carbonaceous fuel; and
    Wherein the second combustion step comprises combusting a sulfurous fuel and a nitrogenous fuel
20. The process of exemplary embodiment 10 wherein said combustion gases originated from a combustion process comprising a first combustion step and a second combustion step;
    Wherein the first combustion step comprises combusting carbonaceous fuel; and
    Wherein the second combustion step comprises combusting a hydrogen fuel and a sulfurous fuel
21. The process of exemplary embodiment 13 wherein said first combustion step comprises combustion in a diatomic oxygen-rich gas and forming diatomic oxygen-lean gas; and
    Said second combustion step comprises combustion in said diatomic oxygen-lean gas and forming a diatomic oxygen-ultra-lean gas
22. The process of exemplary embodiment 1 wherein the gaseous sulfur dioxide resulting from said thermal decomposition comprises a mixture of post-combustion gases and sulfur dioxide
23. The process of exemplary embodiment 1 further comprising recovering or separating at least a portion of the gaseous sulfur dioxide resulting from said thermal decomposition
24. The process of exemplary embodiment 23 where said recovering or separating comprises absorbing sulfur dioxide in a water wash or physical absorbent wash
25. The process of exemplary embodiment 23 where said recovering or separating comprises condensing sulfur dioxide
26. The process of exemplary embodiment 1 further comprising recovering or separating at least a portion of the gaseous sulfur dioxide resulting from said thermal decomposition by absorption into a sulfur dioxide-lean solution, producing a sulfur dioxide-rich solution
27. The process of exemplary embodiment 23 wherein said sulfur dioxide-rich solution comprises the sulfur dioxide-rich solution reacted with calcium carbonate in example exemplary embodiment 1
28. The process of exemplary embodiment 1 wherein said calcium carbonate comprises limestone.

A process for producing captured or high purity $CO_2$ and/or calcium oxide and/or cement and/or $CO_2$-Lean Alkaline-Earth Carbonate comprising:
1) $SO_2(aq) + CO_2\text{-Salt} \square SO_2\text{-Salt} + CO_2(g)$ or acid gas + $CO_2\text{-salt} \square$ acid gas–Salt + $CO_2(g)$
2) Regenerating at least portion of the $SO_2$ in said $SO_2$-salt
   Wherein at least a portion of the $SO_2$ regenerated in '2)' is employed as the input $SO_2$ in '1)'
   Wherein the salt resulting from the regeneration of $SO_2$ ('2') comprises an oxide or oxide salt
   Wherein the resulting from the regeneration of $SO_2$ ('2') comprises an oxide or oxide salt and the oxide salt is employed in the production of cement
   Wherein the salt resulting from the regeneration of $SO_2$ ('2') comprises cement
   Wherein a solid byproduct of '2)' comprises cement
   Wherein '2' is conducted in the presence of one or more or a combination of feedstocks employed in the production of Portland Cement
   Wherein '2' is conducted in the presence of one or more or a combination of clay, silicates, aluminum oxides, iron oxides, silicon oxides, magnesium oxides, or gypsum, or sulfites, or sulfates
   Wherein the salt resulting from the regeneration of $SO_2$ ('2') is employed to absorb carbon dioxide from one or more or a combination of gas streams comprising at least a portion $CO_2$
   Wherein said one or more gas streams comprising at least a portion $CO_2$ comprises air
   Wherein said one or more gas streams comprising at least a portion $CO_2$ comprises flue gas, biogas, natural gas, . . . .
   Wherein the salt resulting from the regeneration of $SO_2$ ('2') comprises lime
   Wherein the salt resulting from the regeneration of $SO_2$ ('2') comprises quicklime
   Wherein the salt resulting from the regeneration of $SO_2$ ('2') is hydrated or mixed with water to produce slacked lime
   Wherein the salt resulting from the regeneration of $SO_2$ ('2') comprises a valuable byproduct comprising an oxide salt
   Wherein the salt resulting from the regeneration of $SO_2$ ('2') comprises a feedstock for cement
   Wherein the $CO_2$-Salt comprises limestone
   Wherein the $CO_2$-Salt comprises A process for producing captured or high purity $CO_2$ and calcium oxide comprising:
1) 1) $SO_2(aq) + CO_2\text{-Salt} \rightarrow SO_2\text{-Salt} + CO_2(g)$ or acid gas + $CO_2\text{-salt} \rightarrow$ acid gas–Salt + $CO_2(g)$
2) Regenerating at least portion of the $SO_2$ in said $SO_2$-salt is regenerated
   Wherein at least a portion of the $SO_2$ regenerated in '2)' is employed as the input $SO_2$ in '1)'

Wherein the salt resulting from the regeneration of SO2 ('2') comprises an oxide or oxide salt.

A process for producing calcium oxide comprising:
Thermally decomposing calcium sulfite to produce calcium oxide and sulfur dioxide
Wherein said thermally decomposing is conducted in a low diatomic oxygen environment
Wherein said low diatomic oxygen environment is facilitated by the combustion of at least a portion of sulfur or hydrogen sulfide or a combination thereof.

A process for producing calcium oxide comprising:
Thermally decomposing calcium sulfite to produce calcium oxide and sulfur dioxide
Wherein said thermally decomposing is conducted in a low oxygen environment
Wherein said low oxygen environment is facilitated by the combustion of at least a portion of sulfur or hydrogen sulfide or a combination thereof
Wherein said low oxygen environment is facilitated by a high concentration of fuel relative to air during combustion, such as a ratio of fuel to air near or equal to or greater than that required by stoichiometry
Wherein said low oxygen environment is facilitated by the use of a recirculating carrier gas Notes
Sulfur dioxide may be provided as an example regenerable acid gas
Increasing Partial Pressure and/or Concentration and/or Volume % Concentration:
Some embodiments may pressurize or compress a gas comprising sulfur dioxide (for example: compressing or pressurizing gas stream represented by '13' or '14' or '15' in FIG. 1) before or during absorption of sulfur dioxide (For example: absorption represented by '16' in FIG. 1). Increasing the pressure of a gas stream comprising sulfur dioxide may increase the partial pressure of sulfur dioxide. Sulfur dioxide may be provides as an example regenerable acid gas.
Some embodiments may increase the concentration and/or partial pressure and/or volume % concentration of sulfur dioxide in a gas mixture (for example: increase the concentration and/or partial pressure and/or volume % concentration of a gas stream represented by '13' or '14' or '15' in FIG. 1) using a gas membrane. Membranes and membrane-based systems for concentrating gases are known in the art and may be employed to increase the concentration of sulfur dioxide in a gas mixture.
Increasing the partial pressure of sulfur dioxide may increase the solubility of sulfur dioxide in an absorption solution. By increasing the solubility of sulfur dioxide, the sulfur dioxide absorption solution may achieve a greater dissolved sulfur dioxide concentration, or the sulfur dioxide absorption column may be smaller, or the sulfur dioxide absorption solution may possess a greater absorption capacity, or the sulfur dioxide absorption system may operate at a lower absorption solution flow rate, or the sulfur dioxide absorption system may operate at a greater absorption efficiency or absorption recovery rate, or a combination thereof. It may be desirable for said pressurization or compression to be conducted after cooling a gas stream comprising sulfur dioxide.
Some embodiments may involve increasing the concentration of dissolved acid gas in the aqueous phase or liquid phase or in a solution. For example, some embodiments may involve increasing the concentration of dissolved acid gas using a membrane-based process. For example, some embodiments may involve increasing the concentration of dissolved acid gas using electrodialysis. For example, some embodiments may involve increasing the concentration of dissolved acid gas using a size-based separation method. For example, some embodiments may involve increasing the concentration of dissolved acid gas using reverse osmosis, forward osmosis, nanofiltration, ultrafiltration, or a combination thereof.

A gas stream comprising sulfur dioxide may be cooled or further cooled or chilled before one or more or a combination of absorption or separation or removal steps.

In FIG. 3, arrows in each figure may indicate the current batch stage in the batch or semi-batch sequence of each reactor. FIG. 3A-3C may show each batch stage in an example batch sequence.

If desired, heat may be recovered from an exothermic enthalpy of reaction during the reaction between calcium carbonate and sulfur dioxide. If desired, energy, such as mechanical energy, may be recovered from the pressure of CO2 generated during, for example, the reaction between calcium carbonate and sulfur dioxide. Alternatively, or additionally, the heat generated may facilitate the reaction or facilitate generation of CO2.

Some embodiments may involve the generation of relatively high partial pressure or purity CO2 during the production of calcium oxide via the displacement of CO2 using an acid gas and the regeneration of said acid gas.

Some embodiments may employ a chemically reactive absorbent in the absorption step, for, for example, capturing carbon dioxide. A chemically reactive absorbent may be beneficial due to, including, but not limited to, one or more or a combination of the following: greater absorption kinetics, greater absorption capacity, or the ability to achieve greater rejection rate with a liquid-phase membrane-based separation process.

Some embodiments may employ physical absorbents as absorbents for absorbing or separating acid gas, such as sulfur dioxide. Said physical absorbents may comprise aqueous or non-aqueous solutions. Said physical absorbents may possess beneficial properties. For example, said beneficial properties may include, but is not limited to, one or more or a combination of the following: greater solubility of sulfur dioxide relative to water, faster absorption kinetics of sulfur dioxide relative to water, faster kinetics relative to water, lower freezing point temperature relative to water, lower vapor pressure relative to water, higher boiling point relative to water, lower viscosity relative to water. Said physical absorbents may comprise aqueous solutions or non-aqueous solutions. Said physical absorbents may comprise physical absorbents employed for acid gas removal known in the art, which may include, but are not limited to, propylene carbonate, ethers of polyethylene glycol, glycol ethers, glycols, or methanol, or a combination thereof.

Some embodiments may employ physical absorbents with beneficial properties as absorbents for absorbing or separating acid gas, such as sulfur dioxide. Some embodiments may employ acid-gas rich solutions of physical absorbents in, for example, the carbon dioxide generating step.

Additional Notes:
Embodiments may be modular or transportable:
Conduct the CO2 production step in a modular fashion—CaSO3 production from CaCO3 may be conducted in a solid-gas or solid-liquid mixing module. The CO2 generated may be employed directly in a nearby oil field or other nearby CO2 demand application. The resulting CaSO3 may be transported in an air-tight/oxygen-free container to a calciner, which may or may not be located nearby. This enables the CO2 generation step to be conducted directly next to the oil field or other CO2 demand application and/or may significantly reduce the need for CO2 pipelines.
Inputs—
CaCO3—transported or mined on site, may be pulverized if desired
SO2—regenerated in the calcining step (calcining step may or may not be located nearby). Makeup SO2 may generated or supplied onsite to make-up for losses of SO2. SO2 may be transported in liquid form by truck or by pipeline or by other means.
Treatment/Transfer Steps—
CO2 separation from residual SO2
Creating an oxygen-free or low oxygen environment for CaSO3 output, especially during transport
Outputs—
CaSO3—transported in a practically oxygen-free environment to the calciner, which may or may not be located on site or near the site. Calciner employed to calcine CaSO3 may be similar a calciner typically employed in CaCO3 calcining, or may be a retrofitted calciner which was formerly employed in calcining CaCO3 or calcining cement or may be designed for calcining CaSO3.
CO2—CO2 is produced, which can be employed directly onsite for, for example, enhanced oil recovery or CO2 conversion or CO2 sequestration.
Retrofit Pre-Existing Calciners for CaO Production using CaSO3 Feedstock:
Pre-existing calciners may be compatible with CaSO3 and SO2. If needed, some calciners may require some parts to be retrofitted with coatings or new materials to ensure compatibility with SO2
Richer fuel to air ratio may be employed minimize O2 in gas stream.
This also means a method for removing or eliminating incomplete combustion products (for example: carbon monoxide (CO) and VOCs) may be required. This may include, but are not limited to, methods for further oxidizing the CO, catalytic converters, or methods for creating value from CO.
Alternatively, or additionally, sulfur and/or nitrogen based fuels may be included or added to, for example, minimize oxygen concentration in combustion gases and/or to provide makeup SO2 for SO2 losses.
Water wash or other method to recover SO2 from flue gas stream. Waste heat may also be recovered before, during, or after this step Air Capture
Calcium Carbonate—Calcium oxide is a core component of many air capture technologies.
The present invention may be employed to regenerate calcium carbonate into calcium oxide and produce high purity and/or high-pressure CO2. Advantageously, in the present invention, pure CO2 may be generated at a high pressure at room temperature or relatively low pressures.
The present invention may comprise the CaO regeneration step of a CO2 air capture or CO2 capture system, which may include the production of high purity or high pressure CO2.
Generated CO2 may contain residual SO2. SO2 may be recovered or separated by, for example, cooling and/or compression, which may result in the liquification or condensation of the SO2.
Trace concentrations of SO2 may be recovered using a caustic solution which may possess less affinity to react with CO2, for example, which may include, but are not limited to, sodium bicarbonate, sodium sulfite solution (which may convert into bisulfite upon reaction with SO2), calcium carbonate, potassium bicarbonate, bicarbonate salts, carbonate salts, sulfite salts, metabisulfite salts, or a combination thereof.
Using a conventional calciner with a fuel rich environment to prevent or minimize the presence of O2
Using the technique for thermal decomposition in an air-free environment to create pure gaseous SO2
Waste heat

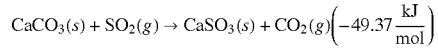
$$CaCO_3(s) + SO_2(g) \rightarrow CaSO_3(s) + CO_2(g) \left(-49.37 \frac{kJ}{mol}\right)$$

More general description of CaO production process/CO2 desorption process:
Acid gas is added to CaCO3 to form concentrated/pure/high pressure CO2 and a Calcium-Acid Gas salt. Said Calcium-Acid Gas salt is then decomposed or regenerated. Said decomposition may involve forming Calcium Oxide and Acid Gas. It may be desirable for the acid gas to comprise an acid gas which can more easily be separated or recovered from a gas mixture than CO2 and/or may be thermodynamically favorable to react with CaCO3 to form CO2(g) and Calcium-Acid Gas salt. For example, concentrated SO2 can more easily be separated from a gas stream than concentrated CO2 because it is highly soluble in water.
Use pulverized or highly crushed or high surface area or fine particulate Calcium Carbonate as the input feedstock or conversion into this small particulate calcium carbonate before or during the reaction with SO2
CaCO3, CaSO3, or a combination thereof may also be pulverized or mixed
Because the reaction of CaCO3 and SO2 is exothermic, the reaction may require cooling or heat may be recovered from the reaction.
SO2 may be reacted with CaCO3 as liquid SO2 or as SO2 dissolved in water, or SO2 dissolved in another liquid or as gaseous SO2 or a combination thereof
If SO2 is dissolved in water or another liquid, it may be desirable for said liquid to have a relatively low concentration of oxygen to prevent the oxidation of SO2 or oxidation of resulting sulfite compounds.

It may be advantageous for $SO_2$ to be dissolved in another liquid, such as water, due to, for example, including, but not limited to, one or more or a combination of the following:
   To enhance reaction rate due to $SO_2$ forming acids in solvents (for example: sulfurous acid in water)
   Enable a lower $SO_2$ vapor pressure compared to gaseous or liquid $SO_2$, which may enable, for example, including, but not limited to, one or more or a combination of the following:
      Reducing concentration and/or amount of $SO_2$ in the desorbed $CO_2$ (from the reaction of $SO_2$ with $CaCO_3$). This may reduce the energy requirements, OPEX, and CAPEX of systems required to separate residual $SO_2$ from the $CO_2$.
      Enable higher temperature operation, which may enable, for example, including, but not limited to, one or more or a combination of the following:
         Faster reaction kinetics, which generally occurs at higher temperatures
         Lower cooling requirements, which may reduce, for example, CAPEX and/or OPEX
         Facilitate recovery of heat generated (e.g. waste heat). Water or other liquid solvent may be an effective heat transfer fluid and enable recovery of heat for use in other applications or within the process or may enable more effective cooling
         Depending on the temperature of the reaction, water or other solvent which $SO_2$ is dissolved in may evaporate or boil. Solvent phase transition may facilitate internal cooling. Additionally, the solvent vapor may facilitate the recovery of $SO_2$ after $CO_2$ desorption. For example, the solvent vapor may be condensed in a condenser, and $SO_2$ may dissolve in said condensed solvent, reducing the $SO_2$ content in the $CO_2$ before further treatment or compression of $CO_2$
         Less energy required in recovering the $SO_2$. $SO_2$ may be recovered as an aqueous solution of $SO_2$. The $SO_2$ rich solution after $SO_2$ absorption may be further concentrated. Alternatively, the $SO_2$ rich solution may be reacted with the $CaCO_3$ without further concentrating of the $SO_2$.
      Enable near ambient temperature or standard temperature operation, which may be considered higher or elevated temperature relative to the temperature of operation using liquid $SO_2$ at standard pressures
         $SO_2$ may have a lower vapor pressure in an aqueous solution or other solvent solution than as liquid $SO_2$ at the same temperature.
         A process operating at near ambient temperature or standard environment temperature ranges may be cooled using low energy cooling sources, which may include, but are not limited to, one or more or a combination of the following: air cooled (e.g. heat exchanged with ambient air), water cooled, liquid cooled, evaporative water cooling, cooling tower cooling, radiative cooling, or cooling with a refrigeration cycle with a high coefficient of performance
         Cooling may be facilitated as liquid solution carrying $SO_2$ may be heat exchanged with heat sink and $CaCO_3$ (or calcium containing reaction intermediates or products). This may enable, for example, greater heat transfer, heat transfer to a greater amount calcium salt mass, or smaller vessel or a combination thereof, if compared to cooling using Solid-Solid heat transfer. It is important to note that Solid-Solid heat transfer may be employed if desired.
It may be advantageous for $SO_2$ to be reacted in a relatively pure form, such as liquid $SO_2$, due to, for example, including, but not limited to, one or more or a combination of the following:
   Faster reaction kinetics
   Potentially higher enthalpy of reaction relative to aqueous $SO_2$
   No or minimal water vapor in desorbed $CO_2$
   Sub-zero degrees Celsius temperature operation is possible
   Lower total liquid volume or mass transfer
   Higher pressure desorption
   All or almost all $SO_2$ entering reactor may react to form $CO_2$, which may enable, for example, including, but not limited to, one or more or a combination of the following:
      Residual $SO_2$ in reactor may be minimal, especially if the $CO_2$ desorption step operates in a batch or semi-batch configuration
      High pressure $CO_2$ desorbed at a low temperature
      Desorbed $CO_2$ will not dissolve in water, because there is no liquid water to dissolve in. For comparison, in a process employing water (or other solvent) other than $SO_2$, water or solvent exiting the process may contain dissolved $CO_2$ (especially if $CO_2$ desorbs at a higher pressure or lower temperature), which may result in $CO_2$ losses.
   If cooling the reactor is required, cooling may involve heat exchange directly with liquid $SO_2$ or cooling the vessel or reactor using, for example, a liquid cooled or liquid-gas phase transition cooled jacket or direct $SO_2$ refrigerant gas-liquid phase transition.
Sulfur dioxide may be separated from flue gas using condensing or cooling separation or cryogenic separation. For example, flue gas comprising sulfur dioxide may be cooled to at or below a dew point or condensation temperature wherein at least a portion of the sulfur dioxide condenses into a liquid phase.
Reactor may undergo mixing to facilitate, for example, the $SO_2+CaCO_3$ reaction.
Process may be configured as batch, semi-batch, or continuous, or a combination thereof.
$SO_2$ losses may occur during operation. $SO_2$ make-up may be accomplished using, including, but not limited to, one or more or a combination of methods.
   For example, $SO_2$ may be directly added to the liquid $SO_2$ input source employed in the reaction of $SO_2$ with $CaCO_3$.
   For example, elemental sulfur or hydrogen sulfide (for example: hydrogen sulfide in sour natural gas) may be combusted along with carbonaceous fuels. For example, sulfur may be mixed with the coal or other fuel source employed to power the calciner, which may result in the formation of $SO_2(g)$. For example, sulfur may be burned as a separate fuel input from carbonaceous fuels, which may involve burning sulfur in a subsequent step. Elemental sulfur may be less expensive and/or easier to transport than $SO_2$. At least a portion of the $SO_2$ generated may be recovered and integrated into the $SO_2$ employed in the process by, for example, the same methods or systems employed to recover the non-virgin SO2. The SO2 generated by this method may mix with the SO2 generated in the calciner, which may enable seamless integration of make-up SO2.

For example, elemental sulfur or hydrogen sulfide may be burned after the burning of the conventional fuel (such as coal or natural gas). This may have multiple benefits:
- Reduce the concentration of residual 02 in the flue gas stream produced after the burning of conventional fuels (such as coal or natural gas).
  - Incomplete combustion of the sulfur fuels may not be as significant or may be less likely as incomplete combustion of carbon-based fuels. Sulfur monoxide (SO) has a positive enthalpy of formation, while carbon monoxide (CO) has a strongly negative enthalpy of formation, so incomplete combustion in a low oxygen environment is much more favorable for a carbon-based fuel than a sulfur-based fuel or elemental sulfur.
  - Enables the combustion of carbon-based fuels in a sufficiently oxygenated environment, allowing for optimal/efficient combustion, potentially minimizing OPEX and/or CAPEX
  - Low oxygen or ultra-low oxygen concentration in the calciner, preventing oxidation of sulfite salts to sulfate salts
- Produces SO2, which may comprise a portion or all of the makeup SO2, which may make-up for any SO2 losses during the process
  - Note: SO2 produced during the combustion of sulfurous fuels to remove residual oxygen may exceed the SO2 losses/required makeup SO2. Excess SO2 may be employed in other value creating applications. For example, said other value creating applications may involve, including, but not limited to, one or more or a combination of the following: excess SO2 may be sold or converted into sulfuric acid and sold, or converted into sulfite salts and sold, or reacted with H2S to produce elemental sulfur, or employed in a Claus process.
  - The conversion of excess SO2 into sulfuric acid, if conducted, is an exothermic process. The heat generated from this reaction may be employed to power or supplement the energy load of other steps in the present invention or other applications demanding heat.

Residual SO2 may be further recovered using a regenerable amine or other regenerable scrubbing process. It may be desirable for said regenerable scrubbing process to minimally react with CO2 or less favorably react with CO2 or not react with CO2, relative to SO2, as CO2 is may be in the gas stream with the SO2. Alternatively or additionally, if the fuels employed to power calcination are not carbon based (for example, may include, but is not limited to, one or more or a combination of the following: Hydrogen sulfide, sulfur, hydrogen, or ammonia), the method employed for scrubbing SO2 may also favorably react with CO2, however, due to the lack of or minimal presence of CO2, the solvent may absorb SO2 with minimal CO2.

Scrubbing systems for recovering residual SO2 may be similar to or the same as methods currently employed at calciners and power plants. For example, for removal of PPT or PPM levels of SO2, a sodium bicarbonate or sodium carbon solution may be employed or calcium carbonate may be employed. If the present invention is retrofitted to a pre-existing calciner, the pre-existing calciner may already have a SO2 scrubber or related emissions control technology.

$CaCO3 \rightarrow CaSO3$ conversion may not be 100%. Residual CaCO3 may be in the calciner. As a result, it may be desirable to operate the calciner at a temperature equal to or greater than the temperature of typical CaCO3 calcining to ensure complete or nearly complete conversion into CaO Water wash may employ methods to separate ash and/or other potential particulate matter from the wash solution before, during, or after, for example, regenerating SO2.

Sodium sulfite or sodium bisulfite or calcium sulfite or other sulfites or calcium sulfate or sulfates may be byproducts of the process for scrubbing residual SO2

Residual SO2 mixed with desorbed CO2 from, for example, the SO2+CaCO3 reaction, may be recovered using CaCO3 (for example: a fluidized bed of CaCO3), which may react to form CaSO3. Resulting CaSO3 may be used, for example, internally within the present invention.

At least a SO2 in flue gas, which may be residual SO2, may be recovered by reaction with CaCO3, which may result in CaSO3. Said CaSO3 may be calcined to produce CaO.

At least a SO2 in flue gas, which may be residual SO2, may be recovered by reaction with sodium or potassium bicarbonates or carbonates, which may result in sodium or potassium sulfites or bisulfites, or metabisulfites. Said sodium or potassium sulfites or bisulfites, or metabisulfites may be regenerated into sodium or potassium bicarbonates or carbonates by reacting with CaCO3 to produce CaSO3. Said CaSO3 may be calcined to produce CaO.

SO2 recovery method may involve, for example, concentrating SO2 or producing nearly pure SO2 after SO2 absorption Bulk SO2 recovery may involve a water wash. The SO2-rich liquid resulting from the water wash may undergo treatment to remove solids and/or may be employed as the SO2 carrier entering a SO2+CaCO3 reactor. Depending on the reaction kinetics of the SO2-rich solution with the CaCO3, the concentration of SO2 in the SO2-rich solution may be sufficient for the SO2 reaction with CaCO3. Advantageously, employing the SO2-rich solution as the SO2 carrier in the reaction of CaCO3 with SO2 may enable lower CAPEX and OPEX, as it may eliminate the need for the energy consumption (OPEX) and construction (CAPEX) of a SO2 concentrating step. Alternatively, or additionally, a SO2 concentrating step may be employed.

Adsorption CO2 capture process employing aqueous SO2 to desorb CO2

Notes:

Some embodiments thermally decompose CaSO3 using combustion gases with complete combustion acting as, for example, heat source and stripping gas.
- Complete combustion, or stoichiometric combustion, or combustion with excess fuel, or combustion with all or almost all oxygen present converted into combustion byproducts, or a combination thereof may enable the combustion gases to be employed directly as heat carriers because the gases may lack oxygen. The lack of oxygen or very low concentrations of oxygen may enable CaSO3 to be decomposed without oxidizing the sulfur species, preventing the formation of SO3(g) or CaSO4.

Combustion gases may be pumped or otherwise forced into contact with the CaSO3 in the one or more CaSO3 decomposition or desorption reactors Combustion gases may be produced by the combustion of carbon-based fuels or fuels without carbon or a combination thereof For carbon based fuels, it may be desirable for the reactor temperature during at least one portion of the thermal decomposition to exceed the decomposition temperature of calcium carbonate. This may prevent a reaction of CO2 with calcium oxide or hydroxide, which may prevent the formation of calcium carbonate. This may also enable any residual calcium carbonate in the reactor to be thermally decomposed, which may enable higher conversion efficiency to calcium oxide.

It may be desirable to employ non-carbon based fuels, which may include, but are not limited to, H2, NH3, H2S, or a combination thereof.

Non-carbon based fuels may be desirable as they may not produce CO2, which may enable the use of lower temperatures during decomposition as there may be no need to inhibit calcium carbonate formation if there is no CO2 present.

For example, H2 may produce steam, which may not react with CaO at the decomposition temperature of CaSO3.

NH3 may produce NO2, which may not react with CaO at the decomposition temperature of CaSO3. Although, NO2 may react with CaO, CaSO3, or CaCO3 at lower temperatures, which may or may not be desirable.

H2S may produce SO2, which is the same gas as the decomposition product of CaSO3. This may be beneficial, as a higher concentration of SO2 may be generated and it may enable a simple composition of the gas stream leaving the decomposition reactor.

Additional Description

The present invention converts CaCO3 into CO2 and CaO. In the process, both CO2 and CaO may be valuable byproducts. The present invention may produce high purity and/or high pressure CO2, which may be suitable for use in enhanced oil recovery and other CO2 utilization or conversion applications. CaO produced by the present invention may be suitable for, for example, including, but not limited to, the production of cement or may comprise quicklime or may be employed to capture CO2 from the air or a combination thereof.

CaO is currently produced by heating CaCO3 or limestone to decompose it into CaO and CO2 in a process called calcining. Calcining is energy intensive and CO2 emission intensive. The process of calcining produces CO2 in the form of flue gas. For CO2 to be useful from calcining, the CO2 must be separated from the flue gas by a post-combustion CO2 capture system, which requires very high capital and operating costs, which generally exceed the value of said CO2. Alternatively, a calciner may be powered by fuel combusted in pure oxygen (oxy-combustion) from an air separation unit. Similar to post-combustion CO2 capture, Oxy-combustion has high capital and operating costs due to the operating costs and capital costs involved with the air separation unit and the significantly higher operating temperature required for decomposing CaCO3 in pure CO2.

The present invention may react SO2 (gas or liquid or aqueous solution or non-aqueous solution or supercritical or solid or a combination thereof) with CaCO3, which may result in the formation of CaSO3 and CO2. The resulting CO2 may undergo further purification to remove at least a portion of SO2 or any other gases present from the CO2. CO2 may be sold or used for one or more applications of high pressure and/or purity CO2. CaSO3 may be thermally decomposed into CaO and SO3. The thermal decomposition of CaSO3 may involve an oxygen free or ultra-low oxygen environment. If a carrier gas is employed, SO3 may be separated from said carrier or stripping gas and may be recovered or regenerated for re-use internally. CaO may be sold or used for one or more applications of CaO. The process may be batch, semi-batch, semi-continuous, continuous, or a combination thereof.

Example Embodiment 1

1. CaCO3 may be placed in a vessel or container. After a desired amount of CaCO3 is added to said vessel or container, the container may be closed. The container may be evacuated of most or all of the remaining oxygen gas or air by, for example, including, but not limited to, one or more or a combination of methods:
    a. Employing a vacuum pump to evacuate air or O2 from from the container and reduce pressure to near vacuum
    b. Purging with nitrogen or other purge gas
    c. Introducing an amount of CH3, H2, Sulfur, H2S, or NH3 or other combustible or oxygen absorbing reagent and combusting these reagents to remove at least a portion of the O2
    d. Gas separation membrane to separate at least a portion of 02 from the remaining gases
    e. Employing an oxygen scavenger, such as, for example, iron oxides or copper or copper oxides
    f. Condensing a portion of the oxygen or condensing another gas to facilitate the separation of oxygen
2. CaCO3+SO2⇒CaSO3+CO2
3. CaSO3+Heat⇒CaO+SO2

Further Description of Step '2)': SO2 may be injected into the container with CaCO3 as one or more or a combination of phases, although for the purposes of description of the present example embodiment, the SO2 may be injected into container with CaCO3 as SO2 liquid, SO2 aqueous, or SO2 non-aqueous solution or a combination thereof. It may be desirable for said liquid or solution to be de-aerated or contain an ultra-low concentration of oxygen. The SO2 may react with said CaCO3 to form CaSO3 and CO2. If desirable, the container/reactor may be heated or cooled or the temperature may be uncontrolled or the temperature may be controlled or a combination thereof. CO2(g) which may result from the reaction may contain a portion of residual SO2 vapor.

Advantageously, SO2 may be easily separated from CO2 due to its, for example, very different boiling point, or significantly higher solubility in water, or different molar mass, or ability to be removed by a SO2 scavenger, or a combination thereof. Residual SO2 in the CO2 may be separated by, for example, including, but not limited to, one or more or a combination of the following: condensation, cooling condensation, compression condensation, water wash, gas separation membrane, reactive absorption and stripping, or SO2 scrubbing molecule (for example: sodium carbonate, sodium bicarbonate, calcium carbonate, calcium bicarbonate, amine-carbon dioxide, water or ammonium carbonate). The resulting high purity CO2 may be employed in one or more applications for pure CO2, which may include, but are not limited to, enhanced oil recovery, CO2 sequestration, conversion into chemicals, or non-hydraulic cement production. Residual SO2 may be recovered or regenerated and/or reused within the process.

Further Description of Step '3)': CaSO3 may be thermally decomposed. Desirable decomposition byproducts may comprise, for example, CaO and SO2. CaSO3 may be decomposed through heating at or above one or more decomposition temperatures. To maximize the formation of CaO and SO2 and/or minimize the formation of CaS or CaSO4, reaction temperature may be maintained between 600-680° C. or above 780° C. Per paper titled 'The Thermal Decomposition Process of Calcium Sulfite' by Royoko et al, CaSO3 may decompose into CaSO4 and CaS at a temperature between 680° C. and 780° C., and thus, it may be desirable to decompose Calcium Sulfite outside the 680° C.-780° C. temperature range if the objective is to form CaO and SO2.

Thermal input may be supplied by, for example, directly heating the container containing CaSO3 or heating a carrier gas which is passed over or through said CaSO3 or heating SO2 (which may also be employed as a carrier gas) or a combination thereof. The container may comprise one or more solid handling or solids storage containers which may be heated known in the art, which may include, but are not limited to, one or more or a combination of the following: rotary kiln, kiln, column, oven, mixing oven, or a combination thereof.

Carrier gas may comprise a non-reactive gas or a gas which is non-reactive with the reagents present under the conditions present (although may comprise a reactive gas if desired), which may include, but are not limited to, one or more or a combination of the following: nitrogen, argon, helium, fluorinated gases, CFCs, HFCs, or sulfur hexafluoride. If a non-SO2 carrier gas is employed, the SO2-lean carrier gas may be heated before or while entering the container containing CaSO3. SO2 may desorb into said carrier gas (which may also be called a stripping gas), which may form SO2-rich carrier gas and CaSO3 may be converted into CaO. Said SO2-rich carrier gas may exit the container containing CaSO3 or CaO or both. To reduce energy consumption, the SO2-rich carrier gas exiting said container containing CaSO3 or CaO or both may be heat exchanged in, for example, a cross heat exchanger, with incoming SO2-lean carrier gas. Following the cross exchanger, at least a portion of the SO2 in said SO2-rich carrier gas may be separated. SO2 separation may be conducted using one or more methods described herein or one or more methods known in the art, which may include, for example, a water wash or non-aqueous liquid wash or a combination thereof. If a water wash or non-aqueous liquid wash is employed, it may be desirable for the rich solution of SO2 resulting from said water wash or non-aqueous liquid wash or both to comprise the medium for SO2 input for step 2, as, for example, this may eliminate or reduce the energy requirement for recovering SO2 by, for example, preventing the need to steam strip or desorb SO2 from said wash solutions. It may be desirable for the water or non-aqueous medium or both to be oxygen-free or contain low concentrations of oxygen. The remaining SO2-lean carrier gas may be recirculated.

Alternatively, the CaSO3 may be decomposed in a pure or concentrated SO2 environment. A pure SO2 environment may be advantageous because, for example, including, but not limited, one or more or a combination of the following: a) SO2 desorbed may be directly reused, minimizing or eliminating the need for additional processing steps, such water washing; or b) reduce heat exchange losses, as hot SO2 exiting may be directly heat exchanged with any SO2 entering the process or supplement heat input if, for example, no addition SO2 is entering; or c) reduce the total amount of mass requiring heating. A pure SO2 environment may have the disadvantage of potentially higher temperature requirements and/or enthalpy of desorption because the CaSO3 may be decomposed in a pure SO3 environment, which, according to the Le Chatelier Principle, may increase the temperature requirements and/or enthalpy of desorption relative to a lower SO2 concentration environment enabled by a carrier gas.

Advantageously, a non-SO2 carrier gas may be employed, while being able to recover the SO2. SO2, unlike CO2, may be condensable and highly water soluble, enabling separation of SO2 from carrier gas streams, which may be inert gas streams, at a relatively low cost.

Note: The present invention may employ other carbonate or bicarbonate salts as feedstocks, which may include, but are not limited to, sodium and potassium carbonates or bicarbonates.

Note: May employ materials compatible with one or more or a combination of the following: SO2, CO2, or H2O or one or more of the fuels (if any) employed in heating and/or their combustion products. It may be desirable for said materials to be compatible at temperature ranges which the materials will be operating.

Note: Advantageous, the present invention does not require an air separation unit or post-combustion CO2 capture to produce pure CO2. Also advantageously, pure CO2 may be produced at a high pressure and/or relatively low temperature and/or with relatively low water vapor concentration.

Note: It may be desirable for the CaCO3 or SO2 or CaSO3 or CaO or a combination thereof in an oxygen-free or very low oxygen environment. An oxygen-free or very low oxygen environment may, for example, prevent the oxidation of SO2 or CaSO3 or other SO3 salt into a SO4 salt.

Note: The present invention may be employed to regenerate CaO from CaCO3 or similar carbonate or bicarbonate molecules in a CO2 capture process. For example, the present invention may be employed in a device to capture CO2 from the air.

Note: The SO2 may be substituted with nitric acid (HNO3). Ca(NO3)2 (which may be a resulting byproduct) can be thermally decomposed in a similar manner to CaSO3 to form CaO and NOx or O2 or NO2 or NO or a combination thereof. NOx, NO2, or NO may be converted back into nitric acid through reaction with water in, for example, the NOx+O2 and NOx+H2O reaction steps of the Ostwald process, regenerating the nitric acid in the present embodiment. Advantageously, Ca(NO3)2 does not oxidize in the presence of O2, which may enable the process to operate in an environment with the presence of O2, if desired.

Note: The carrier gas may comprise a reactive gas if desired. For example, steam may be employed as a carrier gas. Advantageously, steam may condense following calcination and the heat generated may be recoverable and the heat generated may exceed initial heat input to generate steam due to, for example, the exothermic dissolution of SO2 in the condensed steam (water) and/or the exothermic reaction of $H_2O$ with CaO to produce calcium hydroxide. It is important to note that calcium hydroxide may be a byproduct of this version of the present invention.

Note: Any excess water may be removed from system. Similarly, water may be added to the system if desired. Water removal may be conducted by for example, including, but not limited to, one or more or a combination of the following: forward osmosis, decanter, separatory funnel, coalescer, centrifuge, filter, switchable solvent, cyclone, semi-permeable membrane, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems.

Note: Sodium salts may be employed. Sodium Bicarbonate may be decomposed to form Sodium Carbonate, Sodium hydroxide, Sodium Sesquicarbonate, or a combination thereof, or other sodium-carbon dioxide or sodium bicarbonate derivative chemicals.

Note: Separation Devices may include, but are not limited to, one or more or a combination of the following: decanter, separatory funnel, coalescer, centrifuge, filter, switchable solvent, cyclone, semi-permeable membrane, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems.

Note: Heat sources may include, but are not limited to, one or more or a combination of the following: flare gas heat, natural gas combustion, nuclear heat, Waste Heat, Ambient Temperature Changes, Diurnal Temperature Variation, Thermocline liquid body, thermocline solid body, thermocline gaseous body, Thermocline of a water body, halocline, heat pump, solar thermal, solar thermal pond, light, electricity, steam, combustion, compression, pressure increase, geothermal, radiative heat, condensation, exothermic dissolution, exothermic precipitation, exothermic formation of more liquid phases, exothermic formation of less liquid phases, exothermic phase change, or other heat sources described herein.

Note: Systems and methods described herein may be batch, semi-batch, or continuous, or a combination thereof.

Because CaCO3 and CaSO3 may be minimally soluble in water, the aqueous sulfur dioxide may only penetrate surface layers of the CaCO3, meaning some CaCO3 may not undergo the reaction due to a protective layer of the CaSO3. Increasing the reaction yield may be facilitated by, including, but not limited to, reducing CaCO3 particle size and/or maximizing CaCO3 surface area to mass/volume. Increasing the reaction yield may be conducted by adjusting mixing rate and contact time.

Additional Specific Embodiments

1. A process for producing captured carbon dioxide comprising:
   reacting calcium carbonate with sulfur dioxide to produce calcium sulfite and gaseous carbon dioxide; and
   thermally decomposing said calcium sulfite to produce gaseous sulfur dioxide.
2. The process of embodiment 1 wherein said thermal decomposing is conducted under conditions to further produce cement.
3. The process of embodiment 1 wherein said thermal decomposed is conducted under conditions to further produce calcium oxide.
4. The process of embodiment 1 wherein said thermal decomposing is conducted in a mixture with calcium carbonate.
5. The process of embodiment 1 wherein said thermal decomposing is conducted in a mixture comprising a clay, or silicon dioxide, or aluminum oxide, or iron oxide, or iron carbonate, or magnesium carbonate, or magnesium oxide, or a silicate, or an aluminate, or shale, or sand, or fly ash, or ash, or slag, or a sulfur oxide, or a combination thereof.
6. The process of embodiment 1 wherein said thermal decomposing is conducted in a low oxygen environment.
7. The process of embodiment 6 wherein said low oxygen environment comprises a concentration of gaseous diatomic oxygen of less than 20,000 PPM.
8. The process of embodiment 6 wherein said low oxygen environment comprises a concentration of gaseous diatomic oxygen of less than 10,000 PPM.
9. The process of embodiment 1 wherein said thermal decomposing is conducted in the presence of at least one hot gas.
10. The process of embodiment 9 wherein said at least one hot gas comprises a combustion gas.
11. The process of embodiment 10 wherein said combustion gas originated from combustion of a fuel-rich mixture.
12. The process of embodiment 10 wherein said combustion gas originated from combustion of a fuel comprising a carbonaceous fuel, or a sulfurous fuel, or a nitrogenous fuel, or a hydrogen fuel, or a combination thereof.
13. The process of embodiment 10 wherein said combustion gas originated from a combustion process comprising a first combustion step and a second combustion step;
    wherein the first combustion step comprises combusting carbonaceous fuel; and wherein the second combustion step comprises combusting sulfurous fuel.
14. The process of embodiment 13 wherein the second combustion step reduces diatomic oxygen concentration.
15. The process of embodiment 13 wherein sulfur dioxide is provided in the second combustion step to makeup for sulfur dioxide loss in the process.
16. The process of embodiment 10 wherein said combustion gas originated from a combustion process comprising a first combustion step and a second combustion step;
    wherein the first combustion step comprises combusting carbonaceous fuel; and wherein the second combustion step comprises combusting hydrogen fuel.
17. The process of embodiment 10 wherein said combustion gas originated from a combustion process comprising a first combustion step and a second combustion step;
    wherein the first combustion step comprises combusting hydrogen fuel; and
    wherein the second combustion step comprises combusting sulfurous fuel
18. The process of embodiment 10 wherein said combustion gas originated from a combustion process comprising a first combustion step and a second combustion step;
    wherein the first combustion step comprises combusting carbonaceous fuel; and wherein the second combustion step comprises combusting nitrogenous fuel.
19. The process of embodiment 10 wherein said combustion gas originated from a combustion process comprising a first combustion step and a second combustion step;
    wherein the first combustion step comprises combusting carbonaceous fuel; and wherein the second combustion step comprises combusting a mixture comprising a sulfurous fuel and a nitrogenous fuel.

20. The process of embodiment 10 wherein said combustion gas originated from a combustion process comprising a first combustion step and a second combustion step; wherein the first combustion step comprises combusting carbonaceous fuel; and wherein the second combustion step comprises combusting a mixture comprising a hydrogen fuel and a sulfurous fuel.

21. The process of embodiment 13 wherein said first combustion step comprises combusting the carbonaceous fuel with a diatomic oxygen-rich gas to form a diatomic oxygen-lean gas; and wherein said second combustion step comprises combusting the sulfurous fuel with the diatomic oxygen-lean gas and to form a diatomic oxygen-ultra-lean gas.

22. The process of embodiment 1 wherein the gaseous sulfur dioxide comprises a mixture of other gases 23. The process of embodiment 1 further comprising recovering at least a portion of the gaseous sulfur dioxide resulting from said thermal decomposing.

24. The process of embodiment 23 where said recovering comprises absorbing sulfur dioxide in a wash.

25. The process of embodiment 23 where said recovering comprises condensing sulfur dioxide.

26. The process of embodiment 1 further comprising recovering at least a portion of the gaseous sulfur dioxide resulting from said thermal decomposing by absorption of said gaseous sulfur dioxide into a sulfur dioxide-lean solution to produce a sulfur dioxide-rich solution.

27. The process of embodiment 1 wherein the sulfur dioxide reacted with the calcium carbonate is in the form of a sulfur dioxide-rich solution and wherein the reaction with the calcium carbonate further produces a sulfur dioxide-lean solution.

28. The process of embodiment 27 which further comprises recovering at least a portion of the gaseous sulfur dioxide resulting from said thermal decomposing by absorption of said gaseous sulfur dioxide into the sulfur dioxide-lean solution to produce a sulfur dioxide-rich solution.

29. The process of embodiment 1 wherein said calcium carbonate comprises limestone.

A process for producing captured carbon dioxide comprising:
reacting a carbonate salt with a regenerable acid gas to produce a cation-regenerable acid gas salt and gaseous carbon dioxide; and
thermally decomposing said cation-regenerable acid gas salt to produce cement, an oxide, or a combination thereof.

A process for producing captured carbon dioxide comprising:
reacting a carbonate salt with sulfur dioxide to produce a sulfite salt and gaseous carbon dioxide; and
thermally decomposing said sulfite salt to produce cement, an oxide, or a combination thereof.

A process for producing captured carbon dioxide comprising:
reacting a carbonate salt with sulfur dioxide-rich solution to produce a sulfite salt, gaseous carbon dioxide, and sulfur dioxide-lean solution;
separating said sulfite salt from said sulfur dioxide-lean solution; and
thermally decomposing said separated sulfite salt to produce cement, an oxide, or a combination thereof.

A process for producing cement or calcium oxide and captured carbon dioxide comprising:
reacting solid calcium carbonate with sulfur dioxide-rich solution to produce calcium sulfite, gaseous carbon dioxide, and sulfur dioxide-lean solution;
separating said solid calcium sulfite from said sulfur dioxide-lean solution; and
thermally decomposing said separated calcium sulfite to produce calcium oxide, cement, or a combination thereof.

A process for producing captured carbon dioxide comprising:
reacting solid magnesium carbonate with sulfur dioxide-rich solution to produce magnesium sulfite, gaseous carbon dioxide, and sulfur dioxide-lean solution;
separating said solid magnesium sulfite from said sulfur dioxide-lean solution; and
thermally decomposing said separated magnesium sulfite to produce gaseous sulfur dioxide.

Example Chemistry (1) $MgCa(CO_3)_2(s) + 2\ SO_2(aq) \rightarrow CaSO_3(s) + MgSO_3(aq) + 2\ CO_2(g)$
(2) Solid-Liquid Separation
(3) $MgSO_3(aq)$ (dilute feed) + Concentrating $\rightarrow MgSO_3(aq)$ (concentrate) + Water (permeate)
(4) $MgSO_3(aq)$(concentrate) + cooling $\rightarrow MgSO_3(s) + MgSO_3(aq)$(remaining solution)
Note: $MgSO_3(aq)$(remaining solution) may undergo further treatment to remove non-$MgSO_3$ reagents, or may be mixed with the reactants of '(3)', or may be mixed with the reactants of '9', or any combination thereof
(5) $MgSO_3(s)$ + Drying $\rightarrow MgSO_3(s)$ (less wet, or less hydrated, or anhydrous, or any combination thereof)
(6) $MgSO_3(s)$ + Heat $\rightarrow MgO(s) + SO2(g)$
(7) $CaSO_3(s)$ + Drying $\rightarrow CaSO_3(s)$ (less wet, or less hydrated, or anhydrous, or any combination thereof)
(8) $CaSO_3(s)$ + Heat $CaO(s) + SO2(g)$
(9) Water (permeate) + 2 $SO_2(g) \rightarrow$ 2 $SO_2(aq)$ Example Step-By-Step Description (1) $MgCa(CO_3)_2(s)$ is contacted with or reacted with a solution comprising aqueous sulfur dioxide, which may result in the formation of captured $CO_2(g)$, or magnesium sulfite, or calcium sulfite, or any combination thereof. Captured $CO_2$ may comprise an output of the process and may undergo further treatment or compression. Due to the dilute concentration of aqueous sulfur dioxide, or the limited residence time of the 'contacting' or 'reacting', or the stoichiometric molar ratio of sulfur dioxide to calcium and/or magnesium, minimal 'bisulfate' may form, and/or magnesium sulfite may be soluble, and/or calcium sulfite may be insoluble. It is important to note magnesium sulfite is soluble in water, while calcium sulfite is practically insoluble in water. The aqueous solution may comprise aqueous magnesium sulfite. The solid phase may comprise calcium sulfite, or residual silicates, or other sulfites, or iron sulfite, or zinc sulfite, or manganese sulfite, or any combination thereof. The present step may be conducted at an elevated temperature, such as a temperature greater than 20° C., or 30° C., or 40° C., or 50° C., or 60° C., or 70° C., or 80° C., or 90° C., to, for example, facilitate reaction kinetics, or increase reaction rate, or increase dissolution rate of $MgSO_3$. The solid-liquid mixture may be transferred to step 2.

(2) The solid liquid mixture may undergo a solid-liquid separate process, forming a solid phase comprising calcium sulfite, or residual silicates, or other sulfites, or iron sulfite, or zinc sulfite, or manganese sulfite, or any combination thereof and a liquid phase comprising aqueous magnesium sulfite, which may comprise 'dilute aqueous magnesium sulfite'.

(3) Dilute aqueous magnesium sulfite may be concentrated using reverse osmosis. It may be desirable to further heat or increase the temperature of $MgSO_3(aq)$ before or during concentrating of $MgSO_3(aq)$ using reverse osmosis to, for example, maximize the solubility and/or maximize the concentration of $MgSO_3(aq)$ in the retentate or concentrate. At least a portion of the permeate produced from the reverse osmosis process may be transferred to and/or employed as a SO2-lean absorption solution in an $SO_2$ absorption process or process for producing aqueous sulfur dioxide. Said permeate may be heat exchanged with the aqueous sulfurous acid entering step 'Or to recover heat and pre-cool the permeate before an $SO_2$ absorption step. The retentate or concentrate may be transferred to step'(4)'.

(4) A concentrate solution comprising aqueous magnesium sulfite may be cooled to precipitate at least a portion of the $MgSO_3$ from the concentrate. $MgSO_3(s)$ may be separated using a solid-liquid separation and transferred to step '5'. The remaining solution separated after $MgSO_3(s)$ separation may comprise remaining $MgSO_3(aq)$. In some embodiments, at least a portion of the remaining $MgSO_3(aq)$ may be transferred to step '(3)' and/or mixed with the dilute aqueous magnesium sulfite before or during reverse osmosis concentrating. In some embodiments, at least a portion of the remaining $MgSO_3(aq)$ may be heated and further concentrated using a reverse osmosis process, or a forward osmosis process, or a distillation process, or cryodesalination process, or a freezing desalination process, or crystalizing process, or a combination thereof and/or $MgSO_3(s)$ may be precipitated, or any combination thereof. In some embodiments, at least a portion of the remaining $MgSO_3(aq)$ may be treated to remove at least a portion of non-$MgSO_3(aq)$ impurities. In some embodiments, at least a portion of the remaining $MgSO_3(aq)$ may be transferred to an $SO_2$ absorption step, such as step '9', and/or mixed with water or water permeate.

(5) $MgSO_3(s)$ may be dried using one or more or a combination of drying processes. For example, $MgSO_3(s)$ may be heated in the presence of a carrier gas and water may be removed from said carrier gas. For example, $MgSO_3(s)$ may be dried using the hydration of calcium oxide to calcium hydroxide, the hydration of magnesium oxide to magnesium hydroxide, or a combination thereof. For example, $MgSO_3(s)$ may be dried in the presence of a dry carrier gas. For example, $MgSO_3(s)$ may be dried in the presence of a carrier gas, wherein said carrier gas comprises an inert gas or a gas without or with minimal concentration of diatomic oxygen. For example, $MgSO_3(s)$ may be dried in multiple stages. For example, a $MgSO_3(s)$ hydrate may be melted into a liquid solution and $MgSO_3(s)$ upon heating and water may be further separated using, for example, a zero liquid discharge process. For example, $MgSO_3(s)$ may be dehydrated in a calcination process to produce magnesium oxide and sulfur dioxide. It may be desirable to dry or dehydrate magnesium sulfite before calcining to, for example, minimize energy consumption, or minimize the energy consumption during calcining, or minimize the cost of energy used in the process, or a combination thereof.

(6) $MgSO_3(s)$ may be transferred to a kiln or calcining process, wherein $MgSO_3(s)$ may be thermally decomposed into $MgO(s)$ and $SO_2(g)$. Said $MgO(s)$ may comprise a valuable byproduct and/or may undergo further treatment. For example, said $MgO(s)$ may be hydrated to form $Mg(OH)_2$.

(7) Calcium sulfite ($CaSO_3(s)$) may be dried using one or more or a combination of drying processes. For example, $CaSO_3(s)$ may be heated in the presence of a carrier gas and water may be removed from said carrier gas. For example, $CaSO_3(s)$ may be dried using the hydration of calcium oxide to calcium hydroxide, the hydration of magnesium oxide to magnesium hydroxide, or a combination thereof. For example, $CaSO_3(s)$ may be dried in the presence of a dry carrier gas. For example, $CaSO_3(s)$ may be dried in the presence of a carrier gas, wherein said carrier gas comprises an inert gas or a gas without or with minimal concentration of diatomic oxygen. For example, $CaSO_3(s)$ may be dried in multiple stages. For example, a $CaSO_3(s)$ hydrate may be melted into a liquid solution and $CaSO_3(s)$ upon heating and water may be further separated using, for example, a zero liquid discharge process. For example, $CaSO_3(s)$ may be dehydrated in a calcination process to produce calcium oxide and sulfur dioxide. It may be desirable to dry or dehydrate calcium sulfite before calcining to, for example, minimize energy consumption, or minimize the energy consumption during calcining, or minimize the cost of energy used in the process, or a combination thereof.

(8) $CaSO_3(s)$ may be transferred to a kiln or calcining process, wherein $CaSO_3(s)$ may be thermally decomposed into $CaO(s)$ and $SO_2(g)$. Said $CaO(s)$ may comprise a valuable byproduct and/or may undergo further treatment. For example, said $CaO(s)$ may be hydrated to form $Ca(OH)_2$. For example, said $CaO(s)$ may be converted to precipitated calcium carbonate.

(9) $SO_2(g)$, which may be produced from one or more calcining steps, may be absorbed in a solution comprising water to form aqueous sulfur dioxide. Said aqueous sulfur dioxide may be transferred to step '(1)'. In some embodiments, make-up $SO_2$ may be added to make-up for any $SO_2$ losses.

Description of Additional Metal Oxide Production Embodiments

Some embodiments of the present invention may involve reacting a material comprising calcium and magnesium with aqueous sulfur dioxide to form calcium sulfite and/or magnesium sulfite. Some embodiments of the present invention may involve reacting a material comprising calcium carbonate and magnesium carbonate with aqueous sulfur dioxide to form calcium sulfite and/or magnesium sulfite and/or captured carbon dioxide. Some embodiments may involve reacting the material comprising calcium and magnesium under conditions to form sulfites and avoid or minimize the formation of bisulfites. Some embodiments may involve exploiting the solubility difference between calcium sulfite and magnesium sulfite too enable the separation of at least a portion of magnesium sulfite from calcium sulfite. For example, magnesium sulfite may be soluble in water, while calcium sulfite may be practically insoluble in water.

Magnesium sulfite may be separated from at least a portion of calcium sulfite, or calcium carbonate, or magnesium carbonate, or other practically insoluble materials. Calcium sulfite is practically insoluble in water, with a solubility of 0.043 grams per liter at 18° C. Magnesium sulfite is soluble in water, with a solubility of 5.2 grams per liter at 25° C. The reaction of a material comprising calcium and magnesium with aqueous sulfur dioxide may result in the formation of at least a portion of a solid phase comprising calcium and at least a portion of an aqueous phase comprising magnesium sulfite.

Recovering magnesium sulfite from an aqueous solution comprising magnesium sulfite may be conducted using one or more or a combination of methods from separating a dissolved salt from an aqueous solution. Some properties of aqueous magnesium sulfite may enable simple, or low energy, or high throughput, or a combination thereof separation of solid magnesium sulfite from a solution comprising aqueous magnesium sulfite. For example, the solubility of magnesium sulfite increases with temperature—according to Solubilities of magnesium sulfite hydrates by Sohnel, et al, the solubility of magnesium sulfite or magnesium sulfite hexahydrate is 11.04 grams per liter at 43.0° C., or 14.19 grams per liter at 51.4° C., or 19.30 grams per liter at 61.4° C., or 28.87 grams per liter at 71.5° C., or 40.17 grams per liter at 79.0° C., or 53.73 grams per liter at 84.1° C., or 71.21 grams per liter at 88.0° C., or 95.19 grams per liter at 94.0° C. In some embodiments, the reaction of aqueous sulfur dioxide with a material comprising calcium and/or magnesium may be conducted at an elevated temperature, such as, for example, greater than room temperature, or greater than ambient air temperature, or greater than 25° C., or greater than 35° C., or greater than 45° C., or greater than 55° C., or greater than 65° C., or greater than 75° C., or greater than 85° C., or greater than 95° C., or greater than 100° C., or less than the boiling point of the solution at the pressure of the reactor, or greater than 105° C. By conducting at an elevated temperature, the concentration of magnesium sulfite in the aqueous magnesium sulfite may be greater, or the rate of reaction may be greater, or a combination thereof.

Regardless of the temperature of the reaction of aqueous sulfur dioxide with a material comprising calcium and/or magnesium, it may be desirable to concentrate the aqueous magnesium sulfite before or during the precipitation of aqueous magnesium sulfite. It may be desirable for at least a portion of said solution to be concentrated. It may be desirable for at least a portion of said solution to be concentrated using distillation. It may be desirable for at least a portion of said solution to be concentrated using a membrane based process at an elevated temperature. It may be desirable for at least a portion of said solution to be concentrated using a forward osmosis at an elevated temperature. It may be desirable for at least a portion of said solution to be heated before or during concentrating. It may be desirable for at least a portion of said solution to be heated before or during concentrating, to, for example, enable greater solubility of aqueous magnesium sulfite. It may be desirable for said aqueous magnesium sulfite to be treated to prevent scaling during concentrating, or to remove at least a portion of non-magnesium sulfite impurities, or a combination thereof. It may be desirable for at least a portion of said solution to be concentrated using a membrane-based process. For example, said aqueous magnesium sulfite solution may comprise a feed solution to a reverse osmosis process, wherein the reverse osmosis process separates said aqueous magnesium sulfite solution into a permeate comprising water and a concentrate comprising a greater concentration of aqueous magnesium sulfite. Said permeate comprising water may be transferred to a countercurrent heat exchanger for heat recovery and/or to a sulfur dioxide absorption process. It may be desirable for the reverse osmosis process to concentrate magnesium sulfite and/or other salts to a concentration less than their solubility limits to minimize membrane scaling. It may be desirable for the solution to be at an elevation temperature during the reverse osmosis process due to the greater solubility limit of magnesium sulfite with higher temperature and/or to prevent scaling or precipitation during reverse osmosis concentrating. Said concentrate comprising aqueous magnesium sulfite may be cooled to precipitate at least a portion of magnesium sulfite solid, due to, for example, the lesser solubility of magnesium sulfite in water with decreasing temperature, and/or said magnesium sulfite solid may be separated using a solid-liquid separation process. The remaining solution after separating magnesium sulfite solid using a solid-liquid separate process may comprise residual dissolved magnesium sulfite and/or dissolved non-magnesium sulfite salts or chemicals, and/or may undergo further treatment. For example, said remaining solution after separating magnesium sulfite solid using a solid-liquid separate process may be heated and/or transferred or mixed with said feed solution to the reverse osmosis process. For example, said remaining solution after separating magnesium sulfite solid using a solid-liquid separate process may undergo further reverse osmosis steps. For example, said remaining solution after separating magnesium sulfite solid using a solid-liquid separate process may be heated and/or transferred to another membrane-based process. For example, said remaining solution after separating magnesium sulfite solid using a solid-liquid separate process may be distilled and/or crystalized, which may further separate water from dissolved chemicals and/or separate magnesium sulfite from other salts or chemicals. For example, said remaining solution after separating magnesium sulfite solid using a solid-liquid separate process may be mixed with solution transferred to a sulfur dioxide absorption process. For example, said remaining solution after separating magnesium sulfite solid using a solid-liquid separate process may be further treated with, including, but not limited to, one or more or a combination of the following: ion exchange, or resins, or filters, or chemical treatments, or chemical reactions, or membrane based process, or distillation, or multi-effect distillation, or mechanical vapor recompression distillation, or mechanical vapor compression distillation, or multistage flash distillation, or membrane distillation, or cooling, or heating, or freezing, or crydesalination, or solventing-out, or solvent induced precipitation, or salting-out, or other treatment. One or more solutions comprising water may be transferred to a sulfur dioxide absorption step, or mixed with a solution transferred to a sulfur dioxide absorption step, or a combination thereof.

In some embodiments, the material comprising magnesium and calcium may further comprise impurities. In some embodiments, the material comprising magnesium carbonate and calcium carbonate may further comprise impurities. For example, the material comprising magnesium carbonate and calcium carbonate may further comprise magnesium sulfate, or calcium sulfate, or sodium salts, or potassium salts, or iron salts, or manganese salts, or silicon chemicals, or silicon salts, or aluminum salts, or zinc salts, or other salts. Additionally, the aqueous solution comprising magnesium sulfite may be exposed to diatomic oxygen or inadvertently exposed to diatomic oxygen, which may result in a portion of the magnesium sulfite converting to magnesium sulfate. In some embodiments, impurities in the solution comprising aqueous magnesium sulfite may comprise dissolved salts or other chemicals other than magnesium sulfite. In some embodiments, although certain chemicals may be classified as 'impurities', some 'impurities' may comprise valuable products. For example, impurities comprising calcium sulfate and/or magnesium sulfate may be separated and may comprise valuable products. In some embodiments, at least a portion of impurities may be separated from an aqueous solution comprising magnesium sulfite before, or during, or after magnesium sulfite concentrating and/or precipitation of magnesium sulfite. In some embodiments, potential impurities may be practically insoluble in the aqueous magnesium sulfite solution. For example, iron sulfite, or manganese sulfite may be practically insoluble in water if the formation of bisulfite salts is avoided or minimized by employing stoichiometric concentrations of aqueous sulfur dioxide, and/or minimizing residence time. Calcium sulfite solid may comprise other chemicals than calcium sulfite, which may include, but are not limited to, non-calcium sulfite salts described herein.

Calcium sulfite produced from a reaction with aqueous sulfur dioxide may comprise wet calcium sulfite. Wet calcium sulfite may be physically wetted, as in wet calcium sulfite may contain water on the surface of the solid or embedded within the solid. Wet calcium sulfite may comprise hydrated calcium sulfite, which contains a chemically reacted hydrate or wherein water is reacted or part of the calcium sulfite solid. Dry calcium sulfite may comprise calcium sulfite solid which has minimal or no water on its surface or is not physically wetted. Dry calcium sulfite may comprise calcium sulfite solid which is anhydrous. In some embodiments, dry calcium sulfite may comprise calcium sulfite solid may comprise calcium sulfite solid which is partially hydrated, which means it may comprise hydrates of calcium sulfite, although is less hydrated than the potential full hydrate capacity of the calcium sulfite. Transforming wet calcium sulfite to dry calcium sulfite may require energy. Transforming wet calcium sulfite to dry calcium sulfite may comprise 'drying'. Some embodiments may involve employing wet calcium sulfite as an input to a calcining process to produce calcium oxide. Employing wet calcium sulfite as an input to a calcining process to produce calcium oxide may require more energy than employing dry calcium sulfite. Additionally, the amount and/or quality of energy required to calcine wet calcium sulfite may greater than if the wet calcium sulfite is dried into dry calcium sulfite before calcining. One or more or a combination of systems and methods may be employed to dry or dehydrate calcium sulfite. For example, calcium sulfite may be dried by heating the wet calcium sulfite to liberate water as a liquid or a vapor or both and separating said liberated water. If heating is employed, it may be desirable for the temperature of the heat employed to be less than the temperature of calcining calcium sulfite, or for the energy consumed to provide said heat to be less expensive or less carbon emission intensive than the energy consumed to calcine calcium sulfite, or a combination thereof. For example, said heat may be provided by, including, but not limited to, solar thermal, or heat pump, or waste heat, or steam, or low pressure steam, or stored heat, or process heat, or geothermal heat, or nuclear heat, or co-gen heat, or any combination thereof. For example, calcium sulfite may be dried by a carrier gas or stripping gas. For example, calcium sulfite may be dried by a recirculating carrier gas. For example, said recirculating carrier gas may comprise a gas or gas mixture with a diatomic oxygen concentration less than 2 percent by volume. For example, calcium sulfite may be dried by a recirculating carrier gas, wherein at least a portion of water vapor in the recirculating carrier gas is removed by a regenerable liquid desiccant. For example, calcium sulfite may be dried by a recirculating carrier gas, wherein at least a portion of water vapor in the recirculating carrier gas is removed by a regenerable liquid desiccant, which may include, but is not limited to, a glycol liquid desiccant, or glycol dehydration system, or a salt brine, or lithium bromide, or calcium chloride, or a liquid-liquid phase transition liquid desiccant, or a liquid desiccant regenerated by heat, or a liquid desiccant regenerated by vaporization of water, or a liquid desiccant regenerated by freezing desalination, or a liquid desiccant regenerated by a liquid-liquid phase transition into a water-rich phase and a water-lean phase, or a combination thereof. For example, calcium sulfite may be dried by a recirculating carrier gas, wherein at least a portion of water vapor in the recirculating carrier gas is removed by a regenerable solid desiccant, which may include, but is not limited to, an adsorbent, or gypsum, or silicate, or silica gel, or calcium oxide-calcium hydroxide, or a combination thereof. For example, calcium sulfite may be dried by a liquid desiccant, or a solid desiccant, or a combination thereof. For example, calcium sulfite may be dried by a recirculating carrier gas, wherein at least a portion of water vapor in the recirculating carrier gas is removed by a non-regenerated desiccant, which may comprise a solid or a liquid. For example, a non-regenerated desiccant may comprise a material which reacts with water to form a product, which may be removed from the process as a valuable product, or is disposed. For example, an example non-regenerated solid desiccant may comprise calcium oxide reacted with water or water vapor to form calcium hydroxide. For example, in some embodiments, calcium oxide produced by the process may be reacted with water vapor in said carrier gas, removing at least a portion of said water vapor while forming calcium hydroxide. Said calcium hydroxide may comprise a valuable product, or may be further reacted with water, or may be converted into other derivatives of calcium hydroxide. In some embodiments, at least a portion of heat generated from forming calcium hydroxide, from, for example, calcium oxide, may be employed to power at least a portion of the energy required to dry the wet calcium sulfite solid.

Magnesium sulfite solid produced in one or more steps of the process may comprise wet magnesium sulfite. Wet magnesium sulfite may be physically wetted, as in wet magnesium sulfite may contain water on the surface of the solid or embedded within the solid. Wet magnesium sulfite may comprise hydrated magnesium sulfite solid, which contains a chemically reacted hydrate or wherein water is reacted or part of the magnesium sulfite solid. Dry magnesium sulfite may comprise magnesium sulfite solid which has minimal or no water on its surface or is not physically wetted. Dry magnesium sulfite may comprise magnesium sulfite solid which is anhydrous. In some embodiments, dry magnesium sulfite may comprise magnesium sulfite solid and/or may comprise magnesium sulfite solid which is partially hydrated, which means it may comprise hydrates of magnesium sulfite, although is less hydrated than the potential full hydrate capacity of the magnesium sulfite. Transforming wet magnesium sulfite into dry magnesium sulfite may require energy. Transforming wet magnesium sulfite to dry magnesium sulfite may comprise 'drying'. Some embodiments may involve employing wet magnesium sulfite as an input to a calcining process to produce magnesium oxide. Employing wet magnesium sulfite as an input to a calcining process to produce magnesium oxide may require more energy than employing dry magnesium sulfite. Additionally, the amount and/or quality of energy required to calcine wet magnesium sulfite may greater than if the wet magnesium sulfite is dried into dry magnesium sulfite before calcining. One or more or a combination of systems and methods may be employed to dry or dehydrate magnesium sulfite. For example, magnesium sulfite may be dried by heating the wet magnesium sulfite to liberate water as a liquid or a vapor or both and separating said liberated water. If heating is employed, it may be desirable for the temperature of the heat employed to be less than the temperature of calcining magnesium sulfite, or for the energy consumed to provide said heat to be less expensive or less carbon emission intensive than the energy consumed to calcine magnesium sulfite, or a combination thereof. For example, said heat may be provided by, including, but not limited to, solar thermal, or heat pump, or waste heat, or steam, or low pressure steam, or stored heat, or process heat, or geothermal heat, or nuclear heat, or co-gen heat, or any combination thereof. For example, magnesium sulfite may be dried by a carrier gas or stripping gas. For example, magnesium sulfite may be dried by a recirculating carrier gas. For example, said recirculating carrier gas may comprise a gas or gas mixture with a diatomic oxygen concentration less than 2 percent by volume. For example, magnesium sulfite may be dried by a recirculating carrier gas, wherein at least a portion of water vapor in the recirculating carrier gas is removed by a regenerable liquid desiccant. For example, magnesium sulfite may be dried by a recirculating carrier gas, wherein at least a portion of water vapor in the recirculating carrier gas is removed by a regenerable liquid desiccant, which may include, but is not limited to, a glycol liquid desiccant, or glycol dehydration system, or a salt brine, or lithium bromide, or calcium chloride, or a liquid-liquid phase transition liquid desiccant, or a liquid desiccant regenerated by heat, or a liquid desiccant regenerated by vaporization of water, or a liquid desiccant regenerated by freezing desalination, or a liquid desiccant regenerated by a liquid-liquid phase transition into a water-rich phase and a water-lean phase, or a combination thereof. For example, magnesium sulfite may be dried by a recirculating carrier gas, wherein at least a portion of water vapor in the recirculating carrier gas is removed by a regenerable solid desiccant, which may include, but is not limited to, an adsorbent, or gypsum, or silicate, or silica gel, or calcium oxide-calcium hydroxide, or an acid, or a combination thereof. For example, magnesium sulfite may be dried by a liquid desiccant, or a solid desiccant, or a combination thereof. For example, magnesium sulfite may be dried by a recirculating carrier gas, wherein at least a portion of water vapor in the recirculating carrier gas is removed by a non-regenerated solid desiccant. For example, a non-regenerated solid desiccant may comprise a material which reacts with water to form a product, which may be removed from the process as a valuable product, or may be disposed, or both. For example, an example non-regenerated solid desiccant may comprise calcium oxide reacted with water or water vapor to form calcium hydroxide. For example, in some embodiments, calcium oxide produced by the process may be reacted with water vapor in said carrier gas, removing at least a portion of said water vapor while forming calcium hydroxide. Said calcium hydroxide may comprise a valuable product, or may be further reacted with water, or may be converted into other derivatives of calcium hydroxide. In some embodiments, at least a portion of heat generated from forming calcium hydroxide, from, for example, calcium oxide, may be employed to power at least a portion of the energy required to dry the wet magnesium sulfite solid.

In some embodiments, said carrier gas may comprise high temperature steam. Said high temperature steam may be at a temperature greater than the temperature required to form gas phase water in the vapor-solid equilibrium of a hydrate of calcium sulfite, or a hydrate of magnesium sulfite, or any combination thereof.

In some embodiments, drying may be facilitated by mixing or directly contacting solid magnesium sulfite or solid calcium sulfite with a desiccant.

In some embodiments, calcium sulfite and/or magnesium sulfite may be contacted with or reacted with diatomic oxygen. For example, in some embodiments, calcium sulfite and/or magnesium sulfite may be reacted with diatomic oxygen to produce calcium sulfate and/or magnesium sulfate. For example, in in some embodiments, calcium sulfite and/or magnesium sulfite may be reacted with diatomic oxygen to produce calcium sulfate and/or magnesium sulfate and heat. For example, in in some embodiments, at portion of calcium sulfite and/or magnesium sulfite may be reacted with diatomic oxygen to produce heat and/or facilitate the dehydration or drying of calcium sulfite and/or magnesium sulfite. For example, diatomic oxygen may be present in the carrier gas to enable a reaction of a portion of the calcium sulfite, or magnesium sulfite, or both with diatomic oxygen, which may result the production of at least a portion of heat and/or the dehydration or drying of at least a portion of calcium sulfite or magnesium sulfite. In some embodiments, a portion of calcium sulfite may be reacted with diatomic oxygen to produce heat, and/or calcium sulfate, and/or dry stripping or carrier gas, and/or low oxygen dry stripping or carrier gas, and said low oxygen and/or drying stripping or carrier gas may be contacted with wet magnesium sulfite to form dry magnesium sulfite.

In some embodiments it may be desirable to react calcium sulfite with oxygen to from calcium sulfate or gypsum, which may comprise a valuable product from the process. In some embodiments it may be desirable to react magnesium sulfite with oxygen to from magnesium sulfate, which may comprise a valuable product from the process.

In some embodiments, at least a portion of the concentrate solution comprising magnesium sulfite, or solution comprising magnesium sulfite, or the solution comprising magnesium sulfite after the precipitation of at least a portion of magnesium sulfite may be distilled. For example, distilling said one or more solutions may enable the separation of various impurities due to, for example, the difference in solubility of various impurities and the tendency of some salts to precipitate at different points or different times or different concentrations due to differences in solubility or solubility properties. A solid-liquid separation process may be employed to separate at least a portion of a solid precipitate from a remaining liquid solution.

Example Figure Key

Figure 11:
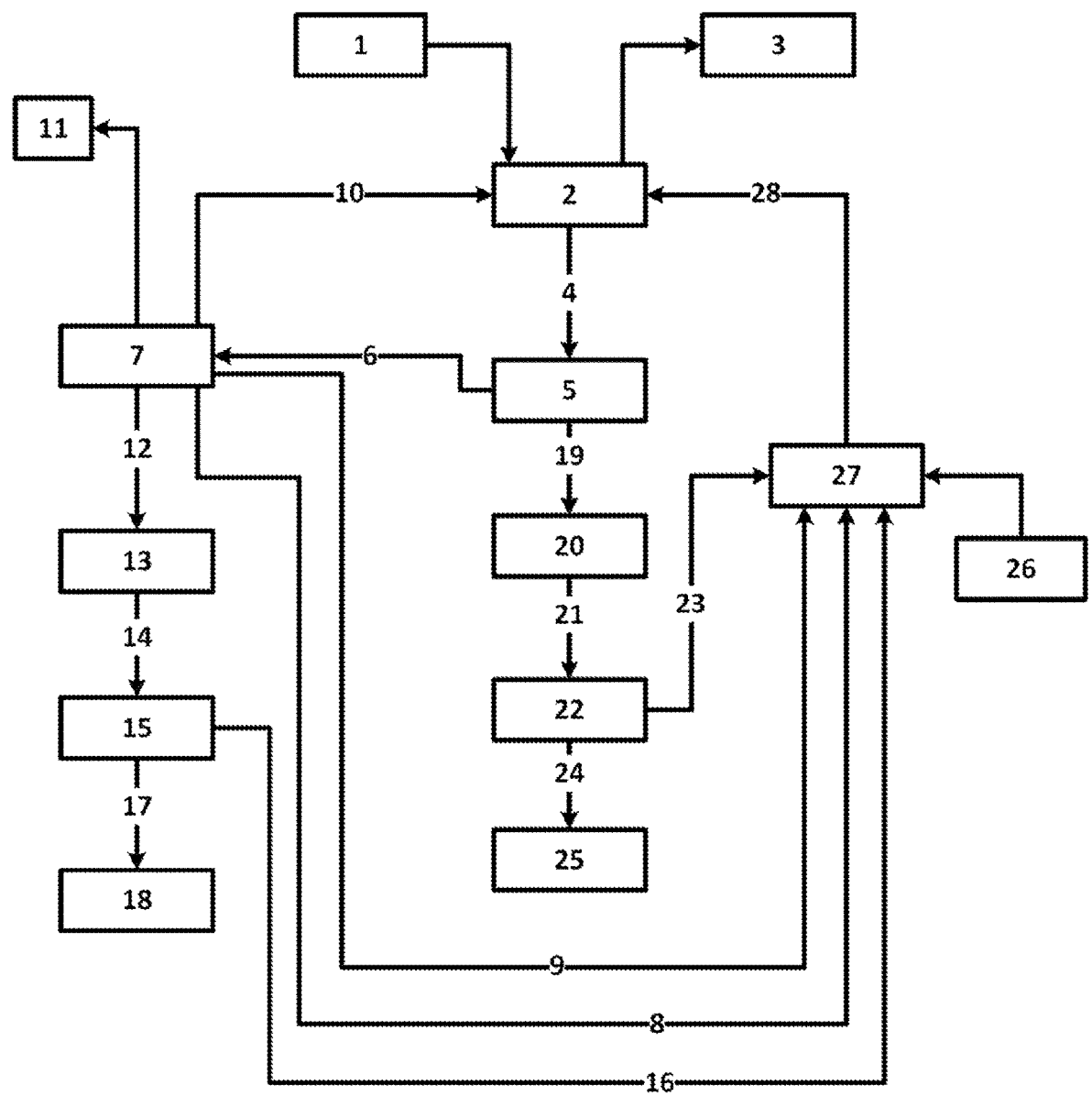
FIG. 11: A figure with numerical labels showing a process for producing calcium oxide and magnesium oxide from a material comprising calcium and magnesium.

| | Example Figure Key for FIG. 11 |
|---|---|
| Label | Description |
| 1 | '1' may comprise a material comprising calcium and/or magnesium. '1' may comprise a solid material comprising calcium - weak acid, or magnesium - weak acid, or any combination thereof. '1' may comprise calcium carbonate, or magnesium carbonate, or any combination thereof. '1' may comprise a calcium silicate, or magnesium silicate, or any combination thereof. '1' may comprise a carbonate, or a silicate, or a ferrite, or an aluminate, or manganese, or iron, or aluminum, or zinc, or any combination thereof. |
| 2 | '2' may comprise a mixing vessel or reactor or a combination thereof. '2' may comprise a process for reacting a material comprising magnesium and/or calcium with aqueous sulfur dioxide. '2' may comprise a process for reacting a material comprising magnesium and/or calcium with aqueous sulfur dioxide to produce magnesium sulfite, and/or calcium sulfite. '2' may comprise a process for reacting a material comprising magnesium and/or calcium with aqueous sulfur dioxide to produce magnesium sulfite, and/or calcium sulfite and/or carbon dioxide. '2' may be designed to operate at least a portion of time at a pressure greater than atmospheric pressure, wherein carbon dioxide generated increases the total pressure to greater than 1 atm, or wherein carbon dioxide generated possesses a partial pressure greater than 1 atm, or a combination thereof. '2' may operate in a batch, or semi-batch, or continuous, or a combination thereof fashion. '2' may operate at an elevated temperature to facilitate reaction kinetics. For example, '2' may operate at a temperature greater than 25° C. For example, '2' may operate at a temperature greater than 25° C. and less than 100° C. For example, '2' may operate at a temperature greater than 25° C. and less than the boiling point of the liquids present in '2' at the total pressure of '2'. In some embodiments, '2' may be heated. In some embodiments, one or more reactions present in '2' may be exothermic and may result in an increase in temperature of one or more reagents or reactants or products in '2'. In some embodiments, '2' may operate at a cold temperature, such as a temperature less than 25° C. In some embodiments, '2' may be cooled. '2' may operate under conditions or residence times or both to enable the formation of dissolved magnesium sulfite, while minimizing the formation of bisulfites. In some embodiments, '2' may be cooled. '2' may operate under conditions or residence times or both to enable the formation of dissolved magnesium sulfite, while minimizing the formation of calcium bisulfite, or iron bisulfite, or manganese bisulfite, or any combination thereof. In some embodiments, '2' may be cooled. '2' may operate under conditions or residence times or both to enable the formation of dissolved magnesium sulfite, while minimizing the formation of magnesium bisulfite, or calcium bisulfite, or iron bisulfite, or manganese bisulfite, or any combination thereof. For example, '2' may involve a stoichiometric ratio of aqueous sulfur dioxide to magnesium and/or calcium to form magnesium sulfite and/or calcium sulfite, while minimizing the formation of calcium bisulfite, which may include, but is not limited to, a stoichiometric ratio less than 2 moles aqueous sulfur dioxide to 1 mole of magnesium and/or calcium, or a stoichiometric ratio less than 1.5 moles aqueous sulfur dioxide to 1 mole of magnesium and/or calcium, or a stoichiometric ratio less than 1.25 moles aqueous sulfur dioxide to 1 mole of magnesium and/or calcium, or a stoichiometric ratio less than 1.1 moles aqueous sulfur dioxide to 1 mole of magnesium and/or calcium, or any combination thereof. For example, '2' may involve a residence time sufficient to form aqueous magnesium sulfite, although insufficient to substantially form aqueous calcium bisulfite. For example, '2' may involve a residence time sufficient to form a concentration of at least 1 gram per liter of aqueous magnesium sulfite, although insufficient to form at least 1 gram per liter of aqueous calcium bisulfite. For example, '2' may involve a residence time sufficient to form a concentration of at least 2 gram per liter of aqueous magnesium sulfite, although insufficient to form at least 1 gram per liter of aqueous calcium bisulfite. |
| 3 | '3' may comprise a gas or gas mixture generated from the reaction of a material comprising magnesium and/or calcium with sulfurous acid. '3' may comprise carbon dioxide. '3' may comprise hydrogen sulfide. '3' may comprise captured carbon dioxide, wherein at least a portion of said captured carbon dioxide is a purity of carbon dioxide is greater than 85% by volume, or greater than 90% by volume, or greater than 95% by volume, or any combination thereof. '3' may comprise captured carbon dioxide, wherein at least a portion of said captured carbon dioxide is at a partial pressure greater than 0.5 atm pressure, or greater than 1 atm pressure, or greater than 1.5 atm pressure, or greater than 2 atm pressure, or greater than 2.5 atm pressure, or any combination thereof. |
| 4 | '4' may comprise a solid-liquid mixture comprising calcium sulfite, or magnesium sulfite, or water, or any combination thereof. '4' may comprise a solid-liquid mixture comprising a solid phase comprising calcium sulfite and a liquid phase comprising aqueous magnesium sulfite. |
| 5 | '5' may comprise a solid-liquid separation process. '5' may comprise a process for separating a solid-liquid mixture comprising a solid phase comprising calcium sulfite and a liquid phase comprising aqueous magnesium sulfite, into a substantially separate solid phase comprising calcium sulfite and a substantially separate liquid phase comprising aqueous magnesium sulfite. |

| Label | Description |
|---|---|
| | Example Figure Key for FIG. 11 |
| 6 | '6' may comprise a liquid comprising aqueous magnesium sulfite. |
| 7 | '7' may comprise a process for separating at least a portion of water from at least a portion of aqueous magnesium sulfite or magnesium sulfite. '7' may comprise a process for concentrating and/or precipitating magnesium sulfite. '7' may comprise a process for removing at least a portion of non-magnesium sulfite impurities, if any. '7' may comprise a process involving concentrating aqueous magnesium sulfite using elevated temperature reverse osmosis and precipitating at least a portion of magnesium sulfite solid from the formed concentrate by cooling said concentrate. The solubility of magnesium sulfite increases significantly with increasing temperature and decreases significantly with decreasing temperature. '7' may involve a chemical reaction, or additives, or ion exchange, or electrodialysis, or other process to treat or remove non-magnesium sulfite impurities. '7' may involve concentrating aqueous magnesium sulfite using electrodialysis. '7' may involve distillation, or cryodesalination, or freezing desalination, or hydrate desalination, or a combination thereof. '7' may involve a solid-liquid phase change, or a gas-liquid phase change, or a liquid-liquid phase transition, or any combination thereof. '7' may involve a membrane based process, which may include, but is not limited to, reverse osmosis, or nanofiltration, or forward osmosis, or membrane distillation, or osmotically assistance reverse osmosis, or low salt rejection reverse osmosis, or DTRO, or any combination thereof. '7' may involve multiple stages or steps. |
| 8 | '8' may comprise water. '8' may comprise water separated from an aqueous magnesium sulfite solution. At least a portion of '8' may comprise a permeate separated from an aqueous magnesium sulfite feed solution using a membrane based process. |
| 9 | In some embodiments, a portion of magnesium sulfite may remain at an aqueous phase. '9' may comprise remaining aqueous magnesium sulfite, which may comprise aqueous magnesium sulfite remaining after precipitating at least a portion of magnesium sulfite. '9' may comprise remaining aqueous magnesium sulfite, which may comprise aqueous magnesium sulfite remaining after precipitating at least a portion of magnesium sulfite from a solution comprising magnesium sulfite concentrate. '9' may comprise remaining aqueous magnesium sulfite which may be employed as a portion of liquid employed to absorb gaseous sulfur dioxide in, for example, later steps. |
| 10 | In some embodiments, a portion of magnesium sulfite may remain at an aqueous phase. '10' may comprise remaining aqueous magnesium sulfite, which may comprise aqueous magnesium sulfite remaining after precipitating at least a portion of magnesium sulfite. '10' may comprise remaining aqueous magnesium sulfite, which may comprise aqueous magnesium sulfite remaining after precipitating at least a portion of magnesium sulfite from a solution comprising magnesium sulfite concentrate. '10' may comprise remaining aqueous magnesium sulfite which may be employed as a portion of the solution present before, or during, or after, or a combination thereof reacting aqueous sulfur dioxide with a material comprising magnesium and/or calcium. |
| 11 | In some embodiments, some non-magnesium or non-magnesium sulfite impurities may be present in a solution comprising aqueous magnesium sulfite. In some embodiments, at least a portion of said impurities may be separated. '11' may comprise at least a portion of said impurities. In some embodiments, at least a portion of said separated impurities may comprise a valuable product. In some embodiments, at least a portion of said separated impurities may comprise a waste product. |
| 12 | '12' may comprise solid magnesium sulfite. '12' may comprise solid magnesium sulfite separated from an aqueous solution comprising aqueous magnesium sulfite. '12' may comprise wet magnesium sulfite, or a hydrate of magnesium sulfite, or a combination thereof. |
| 13 | '13' may comprise a process for drying, or dehydrating, or both solid magnesium sulfite. '13' may involve heating. '13' may involve drying or dehydrating with a liquid desiccant. '13' may involve drying or dehydrating with a solid desiccant. '13' may involve drying with a carrier gas. '13' may involve drying with a carrier gas, wherein at least a portion of water is removed from said carrier gas by a regenerable liquid desiccant. '13' may involve drying with a carrier gas, wherein at least a portion of water is removed from said carrier gas by a regenerable solid desiccant. '13' may involve drying with a carrier gas, wherein at least a portion of water is removed from said carrier gas by a non-regenerable liquid desiccant. '13' may involve drying with a carrier gas, wherein at least a portion of water is removed from said carrier gas by a non-regenerable solid desiccant. '13' may involve drying with a carrier gas, wherein at least a portion of water is removed from said carrier gas by the reaction of calcium oxide with water to form calcium hydroxide. '13' may involve drying with a carrier gas, wherein at least a portion of water is removed from said carrier gas by the reaction of at least partially dehydrated calcium sulfate with water to form hydrated calcium sulfate. '13' may involve heating to a temperature less than 100° C. '13' may involve heating to a temperature greater than 20° C. and less than 800° C. '13' may involve multiple stages or steps. |
| 14 | '14' may comprise dry, or partially dried, or dehydrated, or partially dehydrated, or a combination thereof magnesium sulfite solid. |
| 15 | '15' may comprise a process for decomposing magnesium sulfite into at least a portion of a solid comprising magnesium oxide and a gas comprising sulfur dioxide. '15' may comprise a calcining process. '15' may comprise a shaft kiln, or a rotating kiln, or a |

Example Figure Key for FIG. 11

| Label | Description |
|---|---|
| | batch kiln, or a continuous kiln, or a parallel flow regenerative shaft kiln, or a high performance shaft kiln, a annular shaft kiln, or a suspension calciner, or a preheater rotary kiln, or any combination thereof. '15' may be conducted in a low oxygen environment. '15' may be conducted in a low oxygen environment, wherein the concentration of gaseous diatomic oxygen is less than 1 volume percent, or 2 volume percent, or 3 volume percent, or a combination thereof. '15' may be powered by the combustion of fuel, which may include, but is not limited to, one or more or a combination of the following: carbon fuel, or hydrocarbon, or hydrogen, or ammonia, or sulfur, or nitrogenous fuel, or any combination thereof. '15' may be powered by solar thermal. '15' may be powered electric heating or heating derived from electricity. '15' may be powered by nuclear energy derived heat. |
| 16 | '16' may comprise a gas comprising sulfur dioxide. At least a portion of '16' may comprise a gas comprising sulfur dioxide produced from the decomposition of magnesium sulfite. '16' may comprise a gas mixture comprising sulfur dioxide and one or more other gases. '16' may comprise a gas mixture comprising sulfur dioxide, nitrogen, and a concentration of diatomic oxygen less than 5 volume percent. '16' may comprise a gas mixture comprising sulfur dioxide, nitrogen, and a concentration of diatomic oxygen less than 2 volume percent. '16' may comprise a gas mixture comprising sulfur dioxide, nitrogen, and water vapor. '16' may comprise a gas mixture comprising sulfur dioxide and water vapor, wherein at least a portion of water vapor is condensed and/or at least a portion of heat is recovered from the exothermic condensing said water vapor. '16' may comprise a gas mixture comprising at least a portion of sulfur dioxide and water vapor, wherein at least a portion of water vapor is condensed and/or at least a portion of heat is recovered from the exothermic condensing said water vapor and/or wherein at least a portion of sulfur dioxide dissolves in said condensed water to form aqueous sulfur dioxide. |
| 17 | '17' may comprise magnesium oxide. '17' may comprise magnesium oxide produce from the decomposition of magnesium oxide. '17' may comprise residual magnesium sulfite. '17' may comprise a portion of magnesium sulfate. '17' may comprise residual magnesium sulfite. '17' may comprise a portion of magnesium sulfate, which may comprise a residual contaminant. '17' may comprise residual magnesium sulfite. '17' may comprise a portion of magnesium sulfate, which may have formed due to a portion of magnesium sulfite reacting with a portion of diatomic oxygen. |
| 18 | '18' may comprise the same as '17'. |
| 19 | '19' may comprise solid calcium sulfite. '19' may comprise solid calcium sulfite separated in a solid-liquid separation process from an aqueous solution comprising aqueous magnesium sulfite. '19' may comprise wet calcium sulfite, or a hydrate of calcium sulfite, or a combination thereof. '19' may comprise one or more chemicals in addition to calcium sulfite. For example, '19' may comprise a portion of materials which did not dissolve in a reaction with aqueous sulfur dioxide. For example, '19' may comprise a portion of silicon, or iron, or manganese, or zinc, or aluminum, or any combination thereof. |
| 20 | '20' may comprise a process for drying, or dehydrating, or both solid calcium sulfite. '20' may involve heating. '20' may involve drying or dehydrating with a liquid desiccant. '20' may involve drying or dehydrating with a solid desiccant. '20' may involve drying with a carrier gas. '20' may involve drying with a carrier gas, wherein at least a portion of water is removed from said carrier gas by a regenerable liquid desiccant. '20' may involve drying with a carrier gas, wherein at least a portion of water is removed from said carrier gas by a regenerable solid desiccant. '20' may involve drying with a carrier gas, wherein at least a portion of water is removed from said carrier gas by a non-regenerable liquid desiccant. '20' may involve drying with a carrier gas, wherein at least a portion of water is removed from said carrier gas by a non-regenerable solid desiccant. '20' may involve drying with a carrier gas, wherein at least a portion of water is removed from said carrier gas by the reaction of calcium oxide with water to form calcium hydroxide. '20' may involve drying with a carrier gas, wherein at least a portion of water is removed from said carrier gas by the reaction of at least partially dehydrated calcium sulfate with water to form hydrated calcium sulfate. '20' may involve heating to a temperature less than 100° C. '20' may involve heating to a temperature greater than 20° C. and less than 800° C. '20' may involve multiple stages or steps. |
| 21 | '21' may comprise dry, or partially dried, or dehydrated, or partially dehydrated, or a combination thereof calcium sulfite solid. |
| 22 | '22' may comprise a process for decomposing calcium sulfite into at least a portion of a solid comprising calcium oxide and a gas comprising sulfur dioxide. '22'' may comprise a calcining process. '22' may comprise a shaft kiln, or a rotating kiln, or a batch kiln, or a continuous kiln, or a parallel flow regenerative shaft kiln, or a high performance shaft kiln, a annular shaft kiln, or a suspension calciner, or a preheater rotary kiln, or any combination thereof. '22' may be conducted in a low oxygen environment. '22' may be conducted in a low oxygen environment, wherein the concentration of gaseous diatomic oxygen is less than 1 volume percent, or 2 volume percent, 3 volume percent, or a combination thereof. '22' may be powered by the combustion of fuel, which may include, but is not limited to, one or more or a |

| Label | Description |
|---|---|
| | combination of the following: carbon fuel, or hydrocarbon, or hydrogen, or ammonia, or sulfur, or nitrogenous fuel, or any combination thereof. '22' may be powered by solar thermal. '22' may be powered by nuclear energy derived heat. '22' may be powered electric heating or heating derived from electricity. |
| 23 | '23' may comprise a gas comprising sulfur dioxide. At least a portion of '23' may comprise a gas comprising sulfur dioxide produced from the decomposition of calcium sulfite. '23' may comprise a gas mixture comprising sulfur dioxide and one or more other gases. '23' may comprise a gas mixture comprising sulfur dioxide, nitrogen, and a concentration of diatomic oxygen less than 5 volume percent. '23' may comprise a gas mixture comprising sulfur dioxide, nitrogen, and a concentration of diatomic oxygen less than 2 volume percent. '23' may comprise a gas mixture comprising sulfur dioxide, nitrogen, and water vapor. '23' may comprise a gas mixture comprising sulfur dioxide and water vapor, wherein at least a portion of water vapor is condensed and/or at least a portion of heat is recovered from the exothermic condensing said water vapor. '23' may comprise a gas mixture comprising at least a portion of sulfur dioxide and water vapor, wherein at least a portion of water vapor is condensed and/or at least a portion of heat is recovered from the exothermic condensing said water vapor and/or wherein at least a portion of sulfur dioxide dissolves in said condensed water to form aqueous sulfur dioxide. |
| 24 | '24' may comprise calcium oxide. '24' may comprise calcium oxide produce from the decomposition of calcium oxide. '24' may comprise residual calcium sulfite. '24' may comprise a portion of calcium sulfate. '24' may comprise residual calcium sulfite. '24' may comprise a portion of calcium sulfate, which may comprise a residual contaminant. '24' may comprise residual calcium sulfite. '24' may comprise a portion of calcium sulfate, which may have formed due to a portion of calcium sulfite reacting with a portion of diatomic oxygen. |
| 25 | '25' may comprise the same as '24'. |
| 26 | '26' may comprise 'makeup' sulfur dioxide. In some embodiments, at least a portion of makeup sulfur dioxide is provided from the combustion of sulfur as at least a portion of a fuel in calcining or drying or both. In some embodiments, at least a portion of makeup sulfur dioxide is provided as an input to a process for absorbing sulfur dioxide. Makeup sulfur dioxide may be required to makeup for any sulfur dioxide losses. For example, sulfur dioxide losses may be due to residual reacted sulfur dioxide in the magnesium oxide, or calcium oxide, or non-magnesium sulfite impurities, or other output, or any combination thereof. For example, sulfur dioxide losses may be due to unabsorbed or unreacted sulfur dioxide. |
| 27 | '27' may comprise a process for absorbing gaseous sulfur dioxide in a liquid solution. '27' may comprise a process for absorbing gaseous sulfur dioxide in an aqueous solution. '27' may comprise, including, but not limited to, an absorber, or a wash, or a contactor, or a column, or a membrane contactor, or a mixer, or any combination thereof. In some embodiments, '27' may involve multiple stages, or multiple absorption solutions, or absorption solution inputs, or multiple absorption outputs, or one absorption output, or one absorption stage, or a merger of absorption solution inputs, or any combination thereof. |
| 28 | '28' may comprise aqueous sulfur dioxide. '28' may comprise a solution rich in aqueous sulfur dioxide. In some embodiments, '28' may be pre-heated or heat exchanged before or while entering a process for reacting aqueous sulfur dioxide with a material comprising magnesium and/or calcium. |

Example Figure Key for FIG. 11

Example Exemplary Embodiments

1. A process for producing calcium oxide and magnesium oxide and captured carbon dioxide from a material comprising calcium and magnesium comprising:
   Reacting a material comprising calcium and magnesium carbonate with a solution comprising aqueous sulfur dioxide to form a gas comprising captured $CO_2$, a liquid solution comprising aqueous magnesium sulfite, and a solid comprising calcium sulfite
   Separating said solid comprising calcium sulfite from said liquid solution comprising aqueous magnesium sulfite
   Concentrating said aqueous magnesium sulfite using a membrane based process to form a concentrate solution comprising magnesium sulfite and a permeate comprising water Precipitating solid magnesium sulfite from said concentrate solution comprising aqueous magnesium sulfite calcining said solid calcium sulfite to produce calcium oxide or cement; and
   calcining said solid magnesium sulfite to produce magnesium oxide or cement.

2. The process of example exemplary embodiment 1 wherein said membrane based process comprises reverse osmosis, or forward osmosis, or both.

3. The process of example exemplary embodiment wherein said concentrating is conducted at a temperature greater than 35° C. and less than 100° C.

4. The process of example exemplary embodiment wherein said precipitating is conducted by cooling said concentrate solution to a temperature less than 35° C.

5. The process of example exemplary embodiment 1 wherein said solid calcium sulfite, or solid magnesium sulfite, or both are dried, or dehydrated, or both before calcining.

6. The process of example exemplary embodiment 5 wherein said drying or dehydrating is at least partially conducted at a temperature less than a temperature of calcining.

7. The process of example exemplary embodiment 5 wherein at least a portion of heat for said drying or dehydrating is supplied by reacting calcium oxide with water, or reacting magnesium oxide with water, or both.

8. The process of example exemplary embodiment 5 wherein a carrier gas comprising water vapor is employed during drying or dehydrating and wherein at least a portion of water vapor is removed from said carrier gas 9. The process of example exemplary embodiment 8 wherein at least a portion of water vapor is removed from said carrier gas by reacting the water vapor with calcium oxide to form calcium hydroxide.

10. The process of example exemplary embodiment 8 wherein at least a portion of water vapor is removed from said carrier gas by reacting the water vapor with a non-regenerated desiccant.

11. The process of example exemplary embodiment 8 wherein at least a portion of water vapor is removed from said carrier gas by a liquid desiccant, or a solid desiccant, or both.

12. The process of example exemplary embodiment 8 wherein at least a portion of water vapor is removed from said carrier gas by a membrane-based process.

13. The process of example exemplary embodiment 8 wherein at least a portion of water vapor is removed from said carrier gas by condensing.

14. The process of example exemplary embodiment 8 wherein said carrier gas comprises less than 2 percent by volume diatomic oxygen.

14. The process of example exemplary embodiment 1 wherein the concentration of $CO_2$ in the gas comprising captured $CO_2$ is greater than 95 volume percent.

15. The process of example exemplary embodiment 1 wherein the partial pressure of $CO_2$ in the gas comprising captured $CO_2$ is greater than 1.5 atm.

16. The process of example exemplary embodiment 1 wherein the calcining of calcium sulfite to calcium oxide, or the calcium of magnesium sulfite to magnesium oxide, or both further comprises forming a gas comprising sulfur dioxide.

17. The process of example exemplary embodiment 16 wherein at least a portion of said gas comprising sulfur dioxide in absorbed into a solution comprising water to form aqueous sulfur dioxide.

18. The process of example exemplary embodiment 17 wherein at least a portion of said solution comprising water comprises the permeate produced by said membrane based process.

19. The process of example exemplary embodiment 1 wherein said aqueous magnesium sulfite, or said concentrate, or both is/are treated with a chemical to minimize membrane scaling in the membrane based process.

20. The process of example exemplary embodiment 1 wherein the remaining solution after precipitating magnesium sulfite is heated and mixed with said aqueous magnesium sulfite before or during concentrating by the membrane based process.

21. The process of example exemplary embodiment 1 wherein at least a portion of the remaining solution after precipitating magnesium sulfite is treated to remove at least a portion of non-magnesium sulfite impurities.

22. The process of example exemplary embodiment 22 wherein said treated solution is heated and mixed with the aqueous magnesium sulfite before or during concentrating by the membrane based process.

23. The process of example exemplary embodiment 1 wherein the remaining solution after precipitating magnesium sulfite is employed to absorb sulfur dioxide produced by the calcining of calcium sulfite and magnesium sulfite.

24. The process of example exemplary embodiment 1 wherein at least a portion of sulfur dioxide is recovered by cryogenic separation.

25. The process of example exemplary embodiment 1 wherein at least a portion of the remaining solution after precipitating magnesium sulfite is distilled.

26. A process for producing calcium oxide and magnesium oxide from a material comprising calcium and magnesium comprising:

Reacting a material comprising calcium and magnesium with sulfur dioxide to form a solid comprising calcium sulfite and magnesium sulfite Contacting said solid comprising calcium sulfite and magnesium sulfite with water to form a liquid solution comprising aqueous magnesium sulfite Separating said solid comprising calcium sulfite from said liquid solution comprising aqueous magnesium sulfite 27. The process of example exemplary embodiment 26 further comprising concentrating said aqueous magnesium sulfite using a membrane based process to form a concentrate solution comprising magnesium sulfite and a permeate comprising water 28. The process of example exemplary embodiment 26 further comprising precipitating solid magnesium sulfite from said concentrate solution comprising aqueous magnesium sulfite 29. The process of example exemplary embodiment 26 further comprising drying said precipitated solid magnesium sulfite using a carrier gas with a diatomic oxygen concentration less than 3 volume percent.

30. A process for producing magnesium oxide from a material comprising calcium and magnesium comprising:

Reacting a material comprising calcium and magnesium with a solution comprising aqueous sulfur dioxide to form a liquid solution comprising aqueous magnesium sulfite, and a solid comprising calcium sulfite Separating said solid comprising calcium sulfite from said liquid solution comprising aqueous magnesium sulfite Concentrating said aqueous magnesium sulfite using a membrane-based process to form a concentrate solution comprising magnesium sulfite Precipitating solid magnesium sulfite from said concentrate solution comprising aqueous magnesium sulfite Calcining said solid magnesium sulfite to produce magnesium oxide.

Carboxylic Acid Embodiments

Overview

A process which produces calcium oxide with significantly less or no $CO_2$ emissions is desirable to significantly reduce or eliminate the emissions from calcium oxide production for various applications, including the production of citric acid. A process which recycles calcium oxide in a citric acid production process to, for example, eliminate or greatly reduce the need for virgin calcium oxide input and sulfuric acid input, is desirable, as such a process has the potential to significantly reduce incremental costs, eliminate or greatly reduce waste products, and significantly reduce or eliminate $CO_2$ emissions from citric acid production.

| Example Summary of Inputs and Outputs of an Example Embodiment | |
|---|---|
| Inputs | Outputs |
| Calcium Citrate or A Solution Comprising Citric Acid Requiring Recovery/ Separation of Citric Acid (Note: In some embodiments, the Calcium or magnesium may be recycled within a process and may comprise an intermediate rather than an input) | CaO and/or Cement |
| Fuel Option A: Combustible fuel, such as a Carbonaceous Fuel and/or Sulfurous Fuel and/or Hydrogen Fuel and/or Nitrogenous Fuel | Silicon dioxide or other solid silicon derivative or aggregate or a combination thereof |
| Option B: Electricity, light, or concentrated solar thermal, or a derivative thereof or similar energy or heat source | Unreacted materials |
| | Sulfurous Salt Waste-Product or Useful Byproduct |

Calcium Citrate to Calcium Oxide or Cement and Citric Acid (1) $Ca_3(C_6H_5O_7)_2 \cdot 4H_2O(s) + 6H_2SO_3(aq) \rightarrow 3Ca(HSO_3)_2(aq) + 2C_6H_8O_7(aq) + 4H_2O(l \text{ or } aq)$ (2) $3Ca(HSO_3)_2(aq) + 2C_6H_8O_7(aq) + Heat \rightarrow 3CaSO_3(s) + 3H_2O(l) + 3SO_2(g) + 2C_6H_8O_7(aq)$ (3) $2C_6H_8O_7(aq) + Heat \rightarrow 2C_6H_8O_7(s)$ (4) $3CaSO_3(s) + Heat \rightarrow 3CaO(s) + 3SO_2(g)$ (5) $6SO_2(g) + 6H_2O(l) \rightarrow 6H_2SO_3(aq)$ or (1) $2C_6H_8O_7(aq) + 3Ca(OH)_2(aq) \rightarrow Ca_3(C_6H_5O_7)_2 \cdot 4H_2O(s) + 2H_2O(l)$ (2) $Ca_3(C_6H_5O_7)_2 \cdot 4H_2O(s) + 6H_2SO_3(aq) \rightarrow 3Ca(HSO_3)_2(aq) + 2C_6H_8O_7(aq) + 4H_2O(l \text{ or } aq)$ (3) $3Ca(HSO_3)_2(aq) + 2C_6H_8O_7(aq) + Heat \rightarrow 3CaSO_3(s) + 3H_2O(l) + 3SO_2(g) + 2C_6H_8O_7(aq)$ (4) $2C_6H_8O_7(aq) + Heat \rightarrow 2C_6H_8O_7(s)$ (5) $3CaSO_3(s) + Heat \rightarrow 3CaO(s) + 3SO_2(g)$ (6) $6SO_2(g) + 6H_2O(l) \rightarrow 6H_2SO_3(aq)$ (7) $3CaO(s) + 3H_2O \rightarrow 3Ca(OH)_2 \text{ (aq or s)} + Heat$ Note: Calcium oxide may be recycled in a process for producing citric acid. Calcium may comprise an intermediate.

Note: 2 $C_6H_8O_7$(aq) input may comprise a solution comprising a dilute concentration of citric acid or a solution comprising a mixture of citric acid with other solutes, such as sugars. Citric acid may be isolated or removed from said solution by reacting said solution with calcium hydroxide, producing calcium citrate solid precipitate, which is separated from the solution using a solid-liquid separation method, such as filtration, or centrifuge, or a combination thereof, or other method described herein, or other method described in the art.

Example Step-by-Step Description of an Example Embodiment (1) React a material comprising calcium citrate with aqueous sulfur dioxide or sulfurous acid, which may produce a solution comprising at least a portion dissolved calcium bisulfite and dissolved citric acid.

(2) Desorb or separate at least a portion of sulfur dioxide from a solution comprising aqueous calcium bisulfite and aqueous citric acid, which may produce gaseous sulfur dioxide, solid calcium sulfite, and liquid solution comprising water, or lean aqueous sulfur dioxide, or lean calcium sulfite, or lean calcium bisulfite, and/or citric acid, or a combination thereof. Desorption may require heat input, or depressurization, or vacuum, or vapor compression, or stripping gas, or a combination thereof. Desorbed sulfur dioxide may be transferred to step '(6)'. Solid calcium sulfite and liquid solution may be transferred to step '(3)'. In some embodiments, '(2)' and '(3)' may be conducted in the same step.

(3) Separate solid calcium sulfite from a liquid solution comprising water, or lean aqueous sulfur dioxide, or lean calcium sulfite, or lean calcium bisulfite, and/or citric acid, or a combination thereof. The present step may involve one or more or a combination of solid-liquid separation processes. Separated solid calcium sulfite may be transferred to step '(5)' and separated liquid solution may be transferred to step '(4)'.

(4) Separate liquid solution into separated citric acid and separated water. The present step may involve further treatment or purification before or during separation of citric acid from water. The present step may involve water removal, such as mechanical vapor compression distillation, or mechanical vapor re-compression distillation, or evaporation, or distillation, or membrane based process, or crystallization, or other separation processes described herein, or processes for separating citric acid from water in the art, or processes for purifying citric acid or citric acid solutions in the art, or water removal or separation processes described herein, or other water removal or separation processes described in the art, or other separation processes described in the art, or a combination thereof. The present step may produce, for example, solid citric acid, or a citric acid concentrate solution, or a combination thereof. Citric acid may be a product or output from the present step. Separated or recovered water may be transferred to step '6'.

(5) Decompose solid calcium sulfite into calcium oxide and sulfur dioxide. Calcium oxide may comprise an output of the process, or may be reacted with water to produce calcium hydroxide, or may be transferred to a process to produce calcium citrate or recover or separate citric acid, or a combination thereof. Sulfur dioxide may be transferred to step '6'.

(6) Absorb sulfur dioxide into a liquid solution comprising water, or lean aqueous sulfur dioxide, or lean calcium sulfite, or lean calcium bisulfite, or a combination thereof to form an aqueous sulfur dioxide solution, or a sulfur dioxide rich solution, or a sulfurous acid solution, or a combination thereof. It may be desirable for the concentration of sulfurous acid or sulfur dioxide in said formed liquid solution to be stoichiometrically at a molar ratio greater than or equal to 1:1 relative to the calcium input, or reacting calcium input, or a combination thereof in step 1 to, for example, enable the formation of soluble calcium bisulfite. Said sulfur dioxide rich solution, or a sulfurous acid solution, or a combination thereof may be transferred to, for example, step 1.

Figure 12:
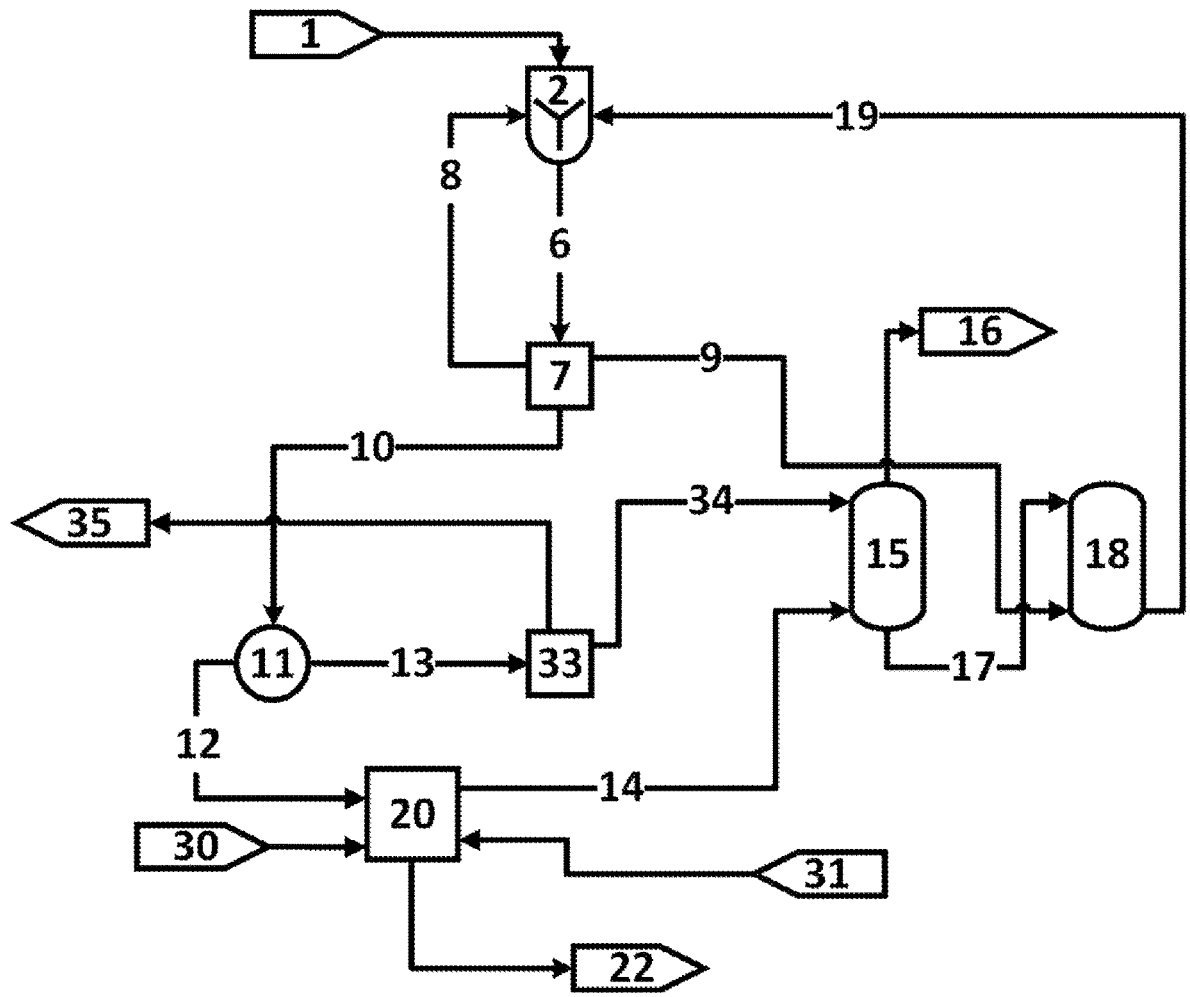
FIG. 12: A figure showing a process for producing citric acid with regeneration of calcium oxide.

Example Figure Key for FIG. 12

| ID | Description |
|---|---|
| 1 | '1' may comprise calcium citrate or an alkaline-earth - organic acid salt. '1' may comprise an input. '1' may be pulverized. |
| 2 | '2' may comprise a process for mixing or reacting or both an input material (such as, for example, '1') with sulfurous acid or a solution comprising dissolved sulfur dioxide. '2' may involve mixing sulfurous acid with a calcium or magnesium - weak acid salt. '2' may involve mixing sulfurous acid with a calcium or magnesium - weak acid salt to form calcium or magnesium sulfite or bisulfite. In the present embodiment, it may be desirable for the molar ratio of sulfur in the sulfurous acid reactant to the calcium and/or magnesium in the input material reactant to be about the same or greater than the molar ratio of sulfur to calcium or magnesium in dissolved calcium bisulfite or magnesium bisulfite. Sulfurous acid reactant in excess of the molar ratio than the molar ratio of sulfur to calcium or magnesium in dissolved calcium bisulfite or magnesium bisulfite may comprise 'excess' sulfurous acid. In some embodiments, 'excess' sulfurous acid may be desirable in '2' to, for example, improve reaction kinetics or otherwise facilitate the reaction to form calcium bisulfite and/or magnesium bisulfite. '2' may form dissolved calcium bisulfite and/or magnesium bisulfite and a weak acid product. Said weak acid product may comprise an aqueous or dissolved organic acid, which may be at least in part separated from the calcium bisulfite and/or magnesium bisulfite within '2' or in a separate step. For example, said weak acid may comprise aqueous citric acid. |
| 6 | '6' may comprise the products from '2'. '6' may involve transferring the products from '6' to a process for mixing or reacting or both to a process for desorbing sulfur dioxide and precipitating calcium sulfite, such as '7'. In some embodiments, '6' may be heat exchanged with '10' before '6' enters '7'. |
| 7 | '7' may comprise a process for desorbing sulfur dioxide from a solution comprising bisulfite. '7' may comprise a process for desorbing sulfur dioxide from a solution comprising calcium bisulfite and citric acid. '7' may comprise a process for converting a solution comprising calcium bisulfite and/or excess aqueous sulfur dioxide and/or aqueous citric acid into sulfur dioxide, calcium sulfite precipitate, and aqueous citric acid. The desorption of at least a portion of sulfur dioxide and/or vaporization of at least a portion of water may require heat input, depressurization, or a combination thereof. A portion of water vapor may form and/or may condense with a portion of sulfur dioxide to form aqueous sulfur dioxide or sulfurous acid, which may comprise, for example '8'. At least a portion of $SO_2(g)$ may be transferred to a sulfur dioxide absorption process, which may comprise, for example, '9'. At least a portion of inputs to '7' may be heat exchanged or counter-current heat exchanged with the outputs of '7', or other liquid or gas or solid streams, or a combination thereof to, for example, minimize the energy required in '7' if, for example, '7' requires heat input, or cooling, or both. '7' may produce a solid-liquid slurry comprising a solid-liquid mixture of calcium sulfite solid and aqueous citric acid liquid. |
| 8 | '8' may comprise aqueous sulfur dioxide. '8' may comprise aqueous sulfur dioxide produced from the condensation of water vapor in the presence of sulfur dioxide gas during or after a sulfur dioxide desorption process (for example, '7'). In some embodiments, '8' may not be produced or may be minimally produced due to the formation of sulfur dioxide gas with minimal water vapor formation, or minimal water vapor condensation, or both. In some embodiments, '8' may be produced due to, for example, the formation of sulfur dioxide gas formation, or water vapor formation, or water vapor condensation, or a combination thereof. In some embodiments, at least a portion of '8' may be heat exchanged with at least a portion of '6'. |
| 9 | '9' may comprise gaseous sulfur dioxide. '9' may comprise sulfur dioxide produced from the desorption of sulfur dioxide from a solution comprising calcium bisulfite, or a solution comprising excess sulfur dioxide, or a solution comprising aqueous sulfur dioxide, or a solution comprising citric acid, or a combination thereof. '9' may comprise a portion of water vapor. '9' may undergo pressurization or compression before or during absorption into a solution in, for example, '18'. |
| 10 | '10' may comprise a solid-liquid mixture. '10' may comprise a solid-liquid mixture comprising calcium sulfite solid and aqueous citric acid, or a $SO_2$(aq)-lean aqueous solution liquid, or a combination thereof |
| 11 | '11' may comprise a process for solid-liquid separation. '11' may comprise a process to separate at least a portion of solid calcium sulfite from at least a portion of water or a $SO_2$(aq)-lean aqueous solution liquid. '11' may be conducted under conditions to minimize exposure to air or diatomic oxygen, to, for example, minimize the potential oxidation of sulfite to sulfate, or other sulfur oxidation, or a combination thereof |
| 12 | '12' may comprise calcium sulfite solid. '12' may be transferred under conditions to minimize exposure to air or diatomic oxygen, to, for example, minimize the potential oxidation of sulfite to sulfate, or other sulfur oxidation, or a combination thereof In some embodiments, '12' may be heat exchanged with one or more inputs to '7' to, for example, facilitate heat recovery. In some embodiments, '12' may be sufficiently pulverized or crushed for calcining or other later steps. In some embodiments, '12' may undergo pulverization, or crushing, or grinding to facilitate calcining or to ensure proper dimensions, or material properties, or a combination thereof for, for example, later process steps. |

-continued

Example Figure Key for FIG. 12

| ID | Description |
|---|---|
| 13 | '13' may comprise aqueous citric acid and may be a $SO_2$(aq)-lean aqueous solution liquid. '13' may be transferred under conditions to minimize exposure to air or diatomic oxygen. In some embodiments, '13' may be heat exchanged with one or more inputs to '7' to facilitate heat recovery. In some embodiments, '13' may be heat exchanged with one or more inputs to '7' to, for example, facilitate heat recovery. The concentration of aqueous sulfur dioxide or dissolved sulfur dioxide in '13' may be lower than the concentration of aqueous sulfur dioxide or dissolved sulfur dioxide in '17'. |
| 14 | '14' may comprise $SO_2$(g). '14' may comprise a gas mixture comprising at least a portion of $SO_2$(g) from the calcination, or decomposition, or both of calcium sulfite. '14' may comprise kiln gases from the thermal decomposition or calcination of calcium sulfite, which may comprise sulfur dioxide, or nitrogen, carbon dioxide, or a combination thereof. It may be desirable for '14' to comprise a low concentration, or minimal concentration, or practically no concentration of diatomic oxygen. '14' may be blown, or pressurized, or compressed before at least a portion of sulfur dioxide in '14' is absorbed into an aqueous solution. '14' may comprise a higher partial pressure, or higher concentration, or a combination thereof of sulfur dioxide gas than, for example, '16'. In some embodiments, heat may be recovered from '14'. In some embodiments, '14' may be cooled. In some embodiments, '14' may be cooled actively, or passively, or a combination thereof |
| 15 | '15' may comprise a gas-liquid contactor, or an absorber, or a combination thereof '15' may comprise a process for absorbing $SO_2$(g) into an aqueous solution. '15' may comprise a process for absorbing $SO_2$(g) from a gas comprising at least a portion of $SO_2$ from gases produced from the decomposition or calcination of calcium sulfite to calcium oxide, or cement, or a combination thereof '15' may involve contacting a gas comprising at least a portion of $SO_2$ with liquid water or a $SO_2$(aq)-lean aqueous solution, which may form an aqueous solution with a greater concentration of aqueous sulfur dioxide and a gas comprising a significantly lower concentration of sulfur dioxide, or a gas comprising less sulfur dioxide, or a combination thereof. It may be desirable for '15' to be conducted in a manner which minimizes the exposure of reagents to air or diatomic oxygen. In some embodiments, '15' may be cooled. In some embodiments, '15' may be cooled actively, or passively, or a combination thereof. In some embodiments, '15' may be pressurized, or the internal pressure of '15' may be greater than atmospheric pressure, or a combination thereof. |
| 16 | '16' may comprise remaining gases after the absorption of at least a portion of sulfur dioxide from '14'. '16' may comprise residual sulfur dioxide, which may comprise sulfur dioxide unabsorbed in '15'. Residual sulfur dioxide may be further separated, or scrubbed. For example, at least a portion of residual sulfur dioxide may be removed by a solution comprising sodium bicarbonate, calcium carbonate, or other carbonate or bicarbonate salt. For example, at least a portion of residual sulfur dioxide may be removed by a sulfur dioxide recovery process, such as a reversibly chemical reaction based process, or a non-reversible chemical reaction process, or an oxidation process, or a catalytic process, or a combination thereof. If '16' comprises at least a portion of carbon dioxide, it may be desirable to capture or separate at least a portion of said carbon dioxide in some embodiments. In some embodiments employing the capturing or separating of carbon dioxide from '16', it may be desirable to separate residual sulfur dioxide before, or simultaneous to, or after the capturing or separation of carbon dioxide. |
| 17 | '17' may comprise a $SO_2$(aq) aqueous solution. '17' may be transferred under conditions to minimize exposure to air or diatomic oxygen. The concentration of aqueous sulfur dioxide or dissolved sulfur dioxide in '17' may be lower than the concentration of aqueous sulfur dioxide or dissolved sulfur dioxide in '19'. '17' may be cooled before or while being transferred to an absorption step. |
| 18 | '18' may comprise a gas-liquid contactor, or an absorber, or a combination thereof. '18' may comprise a process for absorbing $SO_2$(g) into an aqueous solution. '18' may comprise a process for absorbing $SO_2$(g) from a gas comprising at least a portion of $SO_2$(g) from gases produced from the desorption of sulfur dioxide gas from a solution comprising at least a portion of calcium bisulfite, or aqueous sulfur dioxide, or a combination thereof. '18' may involve contacting a gas comprising at least a portion of $SO_2$ with a $SO_2$(aq) aqueous solution, which may form an aqueous solution with a greater concentration of aqueous sulfur dioxide. It may be desirable for '18' to be conducted in a manner which minimizes the exposure of reagents to air or diatomic oxygen. In some embodiments, '18' may be cooled. In some embodiments, '18' may be cooled actively, or passively, or a combination thereof. In some embodiments, '18' may be pressurized, or the internal pressure of '18' may be greater than atmospheric pressure, or a combination thereof. |
| 19 | '19' may comprise a $SO_2$(aq) aqueous solution. '19' may be transferred under conditions to minimize exposure to air or diatomic oxygen. The concentration of aqueous sulfur dioxide or dissolved sulfur dioxide in '19' may be greater than the concentration of aqueous sulfur dioxide or dissolved sulfur dioxide in '17'. In some embodiments, at least a portion of '19' may be heat exchanged with at least a portion of '3'. In some embodiments, '19' may contain aqueous sulfur dioxide in an amount equal to or greater than a molar ratio of 2:1 sulfur:calcium relative to the calcium in '1'. In some embodiments, '19' + '8' may contain aqueous sulfur dioxide in an amount equal to or greater than a molar ratio of 2:1 sulfur:calcium relative to the calcium in '1'. |

-continued

Example Figure Key for FIG. 12

| ID | Description |
|---|---|
| 20 | '20' may comprise a process for calcining, or thermal decomposition, or gas forming reaction, or a combination thereof. '20' may comprise a process for converting calcium sulfite into calcium oxide and sulfur dioxide. '20' may involve converting calcium sulfite and cement manufacturing inputs, such as clay, shale, sand, iron ore, bauxite, fly ash, and slag, into cement, or cement clinker, into cement, or cement clinker, or sulfur dioxide, or a combination thereof. '20' may comprise a kiln or calcining process. '20' may be powered by one or more or a combination of heat sources described herein or heat sources known in the art. '20' may be designed to operate to minimize exposure of reagents to diatomic oxygen or air. '20' may comprise a single step process. '20' may comprise a multi-step process. '20' may comprise a process to produce calcium oxide. '20' may comprise a process to produce calcium oxide, then convert said calcium oxide into cement in a reaction with cement manufacturing inputs, such as clay, shale, sand, iron ore, bauxite, fly ash, and slag, into cement, or cement clinker. '20' may comprise a process to produce cement in a reaction with cement manufacturing inputs, such as clay, shale, sand, iron ore, bauxite, fly ash, and slag, into cement, or cement clinker. '20' may comprise a process for producing sulfur dioxide. '20' may comprise a process for producing calcium oxide from calcium sulfite. |
| 30 | '30' may comprise a gas. '30' may comprise air. '30' may comprise a recirculated gas. '30' may comprise a combination of gases or a mixture of gases or a gas comprising multiple components. '30' may comprise oxygen. '30' may comprise nitrogen. |
| 31 | '31' may comprise energy input. '31' may comprise energy input to power a calciner, or a kiln, or a combination thereof. '31' may comprise energy input to power the conversion of calcium sulfite to calcium oxide and/or cement and/or sulfur dioxide. '31' may comprise, including, but not limited to, one or more or a combination of the following: heat, or fuel, or electricity, or light, or radiative heating, or inductive heating, or heat transfer medium. |
| 33 | '33' may comprise a process for separating or concentrating a dissolved acid, or a dissolved organic acid, such as citric acid. '33' may comprise a process for removing water from citric acid, or concentrating citric acid, or producing solid citric acid, or crystalizing citric acid, or a water removal process, or a purification process, or a combination thereof. '33' may produce separated water and a solid citric acid product. '33' may further separate residual sulfur dioxide, if any, for a solution. If any, said sulfur dioxide may be transferred to an absorption step, such as '15' or '18', or a step to re-incorporate said sulfur dioxide into the process or solution, or a combination thereof. |
| 34 | '34' may comprise water lean in sulfur dioxide or practically free of sulfur dioxide and/or lean in citric acid or practically free in citric acid. '34' may be transferred from a process for separating citric acid to an absorption step, wherein, for example, '34' may comprise an absorption solution input to absorb sulfur dioxide gas. |
| 35 | '35' may comprise separated or isolated citric acid, or other separated acid, or other separated organic acid, or a combination thereof. '35' may comprise citric acid which may be an output of the process. '35' may undergo further treatment or processing. |

Example Exemplary Embodiments

Organic Acid, or Citric Acid, or Soluble Anion or Soluble Acid

1. A process for producing an alkaline-earth oxide and carboxylic acid from an alkaline earth cation-carboxylic acid anion salt comprising:
   Reacting an alkaline-earth cation-carboxylic acid anion salt with aqueous sulfur dioxide to produce aqueous alkaline-earth-bisulfite and aqueous carboxylic acid
   Desorbing sulfur dioxide from said aqueous alkaline-earth-bisulfite and aqueous carboxylic acid solution to produce alkaline-earth-sulfite solid and aqueous carboxylic acid solution
   Separating said alkaline-earth-sulfite solid from said aqueous carboxylic acid solution
   Calcining said alkaline-earth-sulfite solid to produce alkaline-earth-oxide or cement.
2. The process of example embodiment 1 wherein said alkaline-earth comprises calcium.
3. The process of example embodiment 1 wherein said alkaline-earth comprises magnesium.
4. The process of example embodiment 1 wherein said carboxylic acid comprises citric acid.
5. The process of example embodiment 1 wherein said carboxylic acid solution is separated into isolated carboxylic acid and water.
6. The process of example embodiment 5 wherein said water is employed to absorb sulfur dioxide to regenerate the aqueous sulfur dioxide.
7. The process of example embodiment 1 wherein said desorbed sulfur dioxide is absorbed in water to produce aqueous sulfur dioxide.
8. The process of example embodiment 1 wherein said calcining of calcium sulfite produces sulfur dioxide.
9. The process of example embodiment 8 wherein said sulfur dioxide is absorbed in water to produce aqueous sulfur dioxide.
10. The process of example embodiment 1 wherein said alkaline-earth-oxide is reacted with water to produce alkaline-earth-hydroxide.
11. The process of example embodiment 10 wherein said reaction produces heat and said heat is used in one or more processes.
12. The process of example embodiment 10 wherein said alkaline-earth-hydroxide is reacted with a solution comprising at least a portion a carboxylic acid; and forming at least a portion of alkaline-earth cation-carboxylic acid anion salt
13. The process of example embodiment 12 wherein said alkaline-earth cation-carboxylic acid anion salt comprises at least a portion a solid.
14. The process of example embodiment 13 wherein said alkaline-earth cation-carboxylic acid anion salt is separated using a solid-liquid separation process.

15. The process of example embodiment 1 wherein said separating comprises a solid-liquid separation process.
16. The process of example embodiment 1 wherein the process is conducted in the presence of a low diatomic oxygen environment.
17. The process of example embodiment 1 is conducted under conditions to substantially prevent the formation of sulfate.
18. The process of example embodiment 1 wherein said alkaline-earth-hydroxide is employed to produce precipitated alkaline-earth-carbonate.
19. The process of example embodiment 18 wherein said precipitate alkaline-earth-carbonate comprises calcium carbonate, or magnesium carbonate, or both.
20. The process of example embodiment 10 wherein said alkaline-earth-hydroxide forms a solution comprising dissolved aqueous alkaline-earth-hydroxide.
21. The process of example embodiment 12 wherein said alkaline-earth-hydroxide comprises an aqueous solution of dissolved alkaline-earth-hydroxide.
21. The process of example embodiment 12 wherein said alkaline-earth-hydroxide comprises calcium hydroxide.
22. The process of example embodiment 5 wherein said separating produces at least a portion of sulfur dioxide.
23. The process of example embodiment 5 wherein said water comprises at least a portion of aqueous sulfur dioxide.
24. The process of example embodiment 22 wherein said sulfur dioxide comprises gaseous sulfur dioxide.
25. The process of example embodiment 24 wherein at least a portion of said gaseous sulfur dioxide is absorbed to form at least a portion of aqueous sulfur dioxide.
26. The process of example embodiment 11 wherein said one or more processes include desorbing sulfur dioxide, or separating water, or both.
27. A process for producing calcium oxide and carboxylic acid from a calcium cation-carboxylic acid anion salt comprising:
  Reacting a calcium cation-carboxylic acid anion salt with aqueous sulfur dioxide to produce aqueous calcium bisulfite and aqueous carboxylic acid
  Desorbing sulfur dioxide from said aqueous calcium bisulfite and aqueous carboxylic acid solution to produce calcium sulfite solid and aqueous carboxylic acid solution
  Separating said calcium sulfite solid from said aqueous carboxylic acid solution
  Calcining said calcium sulfite solid to produce calcium oxide or cement.
28. A process for producing calcium oxide and citric acid from calcium citrate comprising:
  Reacting calcium citrate with aqueous sulfur dioxide to produce aqueous calcium bisulfite and aqueous citric acid
  Desorbing sulfur dioxide from said aqueous calcium bisulfite and aqueous citric acid solution to produce calcium sulfite solid and aqueous citric acid solution
  Separating said calcium sulfite solid from said aqueous citric acid solution
  Calcining said calcium sulfite solid to produce calcium oxide or cement
  Organic Acid, or Citric Acid, or Soluble Anion or Soluble Acid
1. A process for producing a metal oxide and carboxylic acid from metal cation-carboxylic acid anion salt comprising:
  Reacting a metal-carboxylic acid anion salt with aqueous sulfur dioxide to produce aqueous metal bisulfite and aqueous carboxylic acid
  Desorbing sulfur dioxide from said aqueous metal bisulfite and aqueous carboxylic acid solution to produce metal sulfite solid and aqueous carboxylic acid solution
  Separating said metal sulfite solid from said aqueous carboxylic acid solution
  Calcining said metal sulfite solid to produce metal oxide.
2. The process of example embodiment 1 wherein said metal comprises calcium, or magnesium, or both.
3. The process of example embodiment 1 wherein said metal comprises iron, or manganese, or both.
4. The process of example embodiment 1 wherein said carboxylic acid comprises citric acid.
5. The process of example embodiment 1 wherein said carboxylic acid solution is separated into isolated carboxylic acid and water.
6. The process of example embodiment 5 wherein said water is employed to absorb sulfur dioxide to regenerate the aqueous sulfur dioxide.
7. The process of example embodiment 1 wherein said desorbed sulfur dioxide is absorbed in water to produce aqueous sulfur dioxide.
8. The process of example embodiment 1 wherein said calcining of metal sulfite produces sulfur dioxide.
9. The process of example embodiment 8 wherein said sulfur dioxide is absorbed in water to produce aqueous sulfur dioxide.
10. The process of example embodiment 1 wherein said metal oxide is reacted with water to produce a metal hydroxide.
11. The process of example embodiment 10 wherein said reaction produces heat and said heat is used in one or more processes.
12. The process of example embodiment 10 wherein said metal hydroxide is reacted with a solution comprising at least a portion a carboxylic acid; and
  forming at least a portion of metal-carboxylic acid salt.
13. The process of example embodiment 12 wherein said metal-carboxylic acid salt comprises at least a portion a solid.
14. The process of example embodiment 13 wherein said metal-carboxylic acid salt is separated using a solid-liquid separation process.
15. The process of example embodiment 1 wherein said separating comprises a solid-liquid separation process.
16. The process of example embodiment 1 wherein the process is conducted in the presence of a low diatomic oxygen environment.
17. The process of example embodiment 1 is conducted under conditions to substantially prevent the formation of sulfate.
18. The process of example embodiment 1 wherein said metal-hydroxide is employed to produce precipitated metal-carbonate.
19. The process of example embodiment 18 wherein said precipitate metal-carbonate comprises calcium carbonate, or magnesium carbonate, or iron carbonate, or manganese carbonate, or a combination thereof.
20. The process of example embodiment 10 wherein said metal-hydroxide forms a solution comprising dissolved aqueous metal-hydroxide.
21. The process of example embodiment 12 wherein said metal-hydroxide comprises an aqueous solution of dissolved metal-hydroxide.
21. The process of example embodiment 12 wherein said metal-hydroxide comprises calcium hydroxide.

22. The process of example embodiment 5 wherein said separating produces at least a portion of sulfur dioxide.

23. The process of example embodiment 5 wherein said water comprises at least a portion of aqueous sulfur dioxide.

24. The process of example embodiment 22 wherein said sulfur dioxide comprises gaseous sulfur dioxide.

25. The process of example embodiment 24 wherein at least a portion of said gaseous sulfur dioxide is absorbed to form at least a portion of aqueous sulfur dioxide.

26. The process of example embodiment 11 wherein said one or more processes include desorbing sulfur dioxide, or separating water, or both.

27. A process for producing metal oxide and carboxylic acid from a metal cation-carboxylic acid anion salt comprising:
   Reacting a metal cation-carboxylic acid anion salt with aqueous sulfur dioxide to produce aqueous metal bisulfite and aqueous carboxylic acid
   Desorbing sulfur dioxide from said aqueous metal bisulfite and aqueous carboxylic acid solution to produce metal sulfite solid and aqueous carboxylic acid solution
   Separating said metal sulfite solid from said aqueous carboxylic acid solution
   Calcining said metal sulfite solid to produce calcium oxide or cement.

28. A process for producing metal oxide and citric acid from calcium citrate comprising:
   Reacting metal citrate with aqueous sulfur dioxide to produce aqueous metal bisulfite and aqueous citric acid
   Desorbing sulfur dioxide from said aqueous metal bisulfite and aqueous citric acid solution to produce metal sulfite solid and aqueous citric acid solution
   Separating said metal sulfite solid from said aqueous citric acid solution
   Calcining said metal sulfite solid to produce metal oxide.

1. A process for producing an alkaline-earth oxide and a carboxylic acid from an alkaline earth cation-carboxylic acid anion salt wherein the process comprises:
   reacting an alkaline-earth cation-carboxylic acid anion salt with aqueous sulfur dioxide to produce aqueous alkaline-earth-bisulfite and aqueous carboxylic acid solution;
   desorbing sulfur dioxide from said aqueous alkaline-earth-bisulfite and aqueous carboxylic acid solution to produce alkaline-earth-sulfite solid and aqueous carboxylic acid solution;
   separating said alkaline-earth-sulfite solid from said aqueous carboxylic acid solution; and
   calcining said alkaline-earth-sulfite solid to produce alkaline-earth-oxide, cement, or a combination thereof.

2. The process of example exemplary embodiment 1 wherein said alkaline-earth cation comprises calcium cation.

3. The process of example exemplary embodiment 1 wherein said alkaline-earth cation comprises magnesium cation.

4. The process of example exemplary embodiment 1 wherein said carboxylic acid anion salt comprises citric acid anion salt.

5. The process of example exemplary embodiment 1 which further comprises separating aqueous carboxylic acid solution into isolated carboxylic acid and water.

6. The process of example exemplary embodiment 5 which further comprises absorbing sulfur dioxide with said water to generate aqueous sulfur dioxide for the reacting step.

7. The process of example exemplary embodiment 1 which further comprises absorbing said desorbed sulfur dioxide in water to produce aqueous sulfur dioxide.

8. The process of example exemplary embodiment 1 wherein said calcining said alkaline-earth-sulfite solid produces sulfur dioxide.

9. The process of example exemplary embodiment 8 which further comprises absorbing said sulfur dioxide in water to produce aqueous sulfur dioxide.

10. The process of example exemplary embodiment 1 which further comprises reacting said alkaline-earth-oxide with water to produce alkaline-earth-hydroxide.

11. The process of example exemplary embodiment 10 wherein said reacting produces heat and wherein said heat is used in the process.

12. The process of example exemplary embodiment 10 which further comprises reacting said alkaline-earth-hydroxide with a solution comprising a carboxylic acid to form alkaline-earth cation-carboxylic acid anion salt.

13. The process of example exemplary embodiment 12 wherein at least a portion of said alkaline-earth cation-carboxylic acid anion salt is a solid.

14. The process of example exemplary embodiment 13 which further comprises separating said alkaline-earth cation-carboxylic acid anion salt using solid-liquid separation.

15. The process of example exemplary embodiment 1 wherein said separating comprises a solid-liquid separation step.

16. The process of example exemplary embodiment 1 wherein the process is conducted in the presence of a low diatomic oxygen environment.

17. The process of example exemplary embodiment 1 wherein the process is conducted under conditions to substantially prevent the formation of sulfate.

18. The process of example exemplary embodiment 1 which further comprises producing a precipitated alkaline-earth-carbonate from said alkaline-earth-hydroxide.

19. The process of example exemplary embodiment 18 wherein said precipitated alkaline-earth-carbonate comprises calcium carbonate, magnesium carbonate, or both.

20. The process of example exemplary embodiment 10 wherein said alkaline-earth-hydroxide is dissolved in water.

21. The process of example exemplary embodiment 12 wherein said alkaline-earth-hydroxide is dissolved in water.

21. The process of example exemplary embodiment 12 wherein said alkaline-earth-hydroxide comprises calcium hydroxide.

22. The process of example exemplary embodiment 5 wherein said isolated water comprises dissolved sulfur dioxide.

23. The process of example exemplary embodiment 22 which further comprises separating sulfur dioxide from the isolated water.

24. The process of example exemplary embodiment 22 wherein said sulfur dioxide comprises gaseous sulfur dioxide.

25. The process of example exemplary embodiment 24 wherein at least a portion of said gaseous sulfur dioxide is absorbed to form at least a portion of aqueous sulfur dioxide.

26. The process of example exemplary embodiment 10 wherein said reacting produces heat and wherein said heat is used desorb sulfur dioxide, separate water, or both.

27. A process for producing calcium oxide and carboxylic acid from a calcium cation-carboxylic acid anion salt wherein the process comprises:
   reacting a calcium cation-carboxylic acid anion salt with aqueous sulfur dioxide to produce aqueous calcium bisulfite and aqueous carboxylic acid;

desorbing sulfur dioxide from said aqueous calcium bisulfite and aqueous carboxylic acid solution to produce calcium sulfite solid and aqueous carboxylic acid solution;

separating said calcium sulfite solid from said aqueous carboxylic acid solution; and calcining said calcium sulfite solid to produce calcium oxide, cement, or a combination thereof.

28. A process for producing calcium oxide and citric acid from calcium citrate wherein the process comprises:

reacting calcium citrate with aqueous sulfur dioxide to produce aqueous calcium bisulfite and aqueous citric acid;

desorbing sulfur dioxide from said aqueous calcium bisulfite and aqueous citric acid solution to produce calcium sulfite solid and aqueous citric acid solution;

separating said calcium sulfite solid from said aqueous citric acid solution; and calcining said calcium sulfite solid to produce calcium oxide, cement, or a combination thereof.

Notes

Note: Some embodiments may involve reacting a material comprising calcium and/or magnesium with supercritical, or liquid, or gaseous, or any combination thereof sulfur dioxide to form calcium sulfite and/or magnesium sulfite, then contacting at least a portion of the formed calcium sulfite and/or magnesium sulfite with water to form at least a portion of dissolve magnesium sulfite.

Note: $MgCa(CO_3)_2(s)$ may comprise a solid comprising a mixture of calcium and magnesium salts. $MgCa(CO_3)_2(s)$ may comprise, for example, including, but not limited to, limestone or dolomite. Alternatively, or additionally, $MgCa(CO_3)_2(s)$ may comprise a portion of magnesium silicate or magnesium aluminate or magnesium ferrate. Alternatively, or additionally, $MgCa(CO_3)_2(s)$ may comprise a portion of calcium silicate or calcium aluminate or calcium ferrate.

Note: In some embodiments, a solvent other than or in addition to water may be employed. For example, an organic solvent or inorganic solvent may be present in solution. For example, a glycol, or an alcohol, or a sugar alcohol may be present. For example, an organic solvent or a solvent other than water. For example, ammonia or urea may be present in solution.

Note: Concentration of aqueous magnesium sulfite in a solution comprising aqueous magnesium sulfite may be greater than or equal to one or more or a combination of the following: 0.025 g/L, or 0.05 g/L, or 0.1 g/L, or 0.2 g/L, or 0.3 g/L, 0.4 g/L, or 0.5 g/L, or 0.6 g/L, or 0.7 g/L, or 0.8 g/L, or 0.9 g/L, or 1.0 g/L, or 1.1 g/L, or 1.2 g/L, or 1.3 g/L, or 1.4 g/L, or 1.5 g/L, or 1.6 g/L, or 1.7 g/L, or 1.8 g/L, or 1.9 g/L, or 2 g/L Note: 'g/L' may comprise grams of solute per liter of solution. For example, 1 g/L of magnesium sulfate may comprise a solution with 1 gram of dissolved magnesium sulfite per liter of total solution.

Note: Temperature of at least a portion of concentrating with reverse osmosis or forward osmosis or both may be greater than or equal to one or more or a combination of the following: 0° C., or 5° C., or 10° C., or 15° C., or 20° C., or 25° C., or 30° C., or 35° C., or 40° C., or 45° C., or 50° C., or 55° C., or 60° C., or 65° C., or 70° C., or 75° C., or 80° C., or 85° C., or 90° C., or 95° C., or 100° C., or 105° C., or 110° C., or 115° C.

Note: Temperature of calcining at least a portion of calcium sulfite, or magnesium sulfite, or both may be greater than or equal to one or more or a combination of the following: 500° C., or 550° C., or 600° C., or 650° C., or 700° C., or 750° C., or 775° C., or 800° C., or 825° C., or 850° C., or 875° C., or 900° C.

Note: Temperature of drying or dehydrating or both may be less than or equal to one or more or a combination of the following: 800° C., or 750° C., or 700° C., or 650° C., or 600° C., or 550° C., or 500° C., or 450° C., or 400° C., or 350° C., or 300° C., or 250° C., or 200° C., or 150° C., or 100° C.

Note: The partial pressure of captured carbon dioxide produced by one or more or a combination of embodiments may be greater than or equal to one or more or a combination of the following: 0.05 atm, or 0.1 atm, or 0.2 atm, or 0.3 atm, or 0.4 atm, or 0.5 atm, or 0.6 atm, or 0.7 atm, or 0.8 atm, or 0.9 atm, or 1 atm, or 1.1 atm, or 1.2 atm, or 1.3 atm, or 1.4 atm, or 1.5 atm, or 1.6 atm, or 1.7 atm, or 1.8 atm, or 1.9 atm, or 2.0 atm, or 2.25 atm, or 2.5 atm, or 2.75 atm, or 3 atm, or 4 atm, or 5 atm, or 6 atm, or 7 atm, or 8 atm, or 9 atm, or 10 atm, or 12.5 atm, or 15 atm, or 17.5 atm, or 20 atm, or 25 atm, or 30 atm, or 35 atm, or 40 atm, or 45 atm, or 50 atm Note: The concentration of captured carbon dioxide produced by the process may comprise a volume percent concentration of carbon dioxide which may include, but is not limited to, greater than, or equal to, one or more or a combination of the following: 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%

Note: The concentration of captured carbon dioxide produced by the process may comprise a volume percent concentration of carbon dioxide which may include, greater than, or equal to, one or more or a combination of the following: 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: 'A portion': A portion may comprise a part of a stream or material, or all of a stream or material. A portion may include, but is not limited to, less than, or greater than, or equal to, one or more or a combination of the following: 0%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: Calcining may involve thermally decomposing calcium sulfite and/or magnesium sulfite into calcium oxide and/or magnesium oxide. Calcining may involve thermally decomposing calcium carbonate and/or magnesium carbonate into calcium oxide and/or magnesium oxide.

Note: In some embodiments, calcium sulfite and magnesium sulfite may be calcined separately. For example, in some embodiments, calcium sulfite may be calcined in a separate kiln than magnesium sulfite. For example, in some embodiments, calcium sulfite may be calcined in the same kiln as magnesium sulfite, although in different locations within the same kiln. For example, in some embodiments, calcium sulfite may be calcined in the same kiln as magnesium sulfite, although at different times.

Note: In some embodiments, calcium sulfite and magnesium sulfite may be calcined in the same kiln. For example, a material may comprise both calcium sulfite and magnesium sulfite, and said material comprising both calcium sulfite and magnesium sulfite may be calcined. For example, a separate calcium sulfite and magnesium sulfite may be mixed and may be calcined in the same kiln as a mixture.

Note: Some embodiments may involve using an input material comprising a salt of calcium and/or magnesium and a weak acid, wherein said weak acid comprises a weak acid anion other than a carbon dioxide derivative, or other than a carbonate. For example, said weak acid anion other than a carbon dioxide derivative may comprise, including, but not limited to, one or more or a combination of the following: a sulfide, or silicon derivative, or silicate, or aluminate, or ferrate, or ferrite, or iron, or zinc, or aluminum, or manganese, or copper, or a combination thereof Additional Notes Note: In some embodiments, a material comprising calcium and/or magnesium may comprise calcium silicate or magnesium silicate or both. In some embodiments, a material comprising calcium and/or magnesium may comprise, for example, including, but not limited to, cement, or concrete, or waste concrete, or steel slag, or iron slag, or slag, or a combination thereof.

Note: If non-calcium of non-magnesium metals dissolve or react with $SO_2$ or sulfurous acid, these minerals may be separated before or after separation of calcium sulfite or magnesium sulfite or both. If these non-calcium of non-magnesium metal salts are still dissolved, they may be separated by precipitation, or systems and/or methods for zero liquid discharge, or a combination thereof.

Note: Employ the calcium oxide produced by the present invention as an input to the Solvay to make reduced $CO_2$ emissions sodium carbonate and sodium bicarbonate. Calcium oxide is used in the Solvay process to remove chloride from ammonium chloride.

Note: Some embodiments may employ high temperature steam in the calcination process. In some embodiments, it may be desirable for the temperature of the steam to be greater than the decomposition temperature or decomposition temperature range of calcium hydroxide. At least a portion of the steam may be condensed after forming a mixture with sulfur dioxide. If steam is employed, it must be contacted at a temperature greater than the decomposition temperature of calcium hydroxide.

Note: Sulfur dioxide may be separated or recovered by cryogenic separation, or freezing separation, or liquification separation, or condensing separation, or deposition separation, or a combination thereof. The resulting liquid or solid or supercritical $SO_2$ may be added to water or sulfurous acid solution to form or maintain concentrated or 'excess' sulfurous acid. Alternatively or additionally, the resulting liquid or solid or supercritical $SO_2$ may be reacted with directly with the material comprising calcium and/or magnesium.

Note: Thermally decompose calcium sulfite in an electric kiln

Note: Thermally decompose calcium sulfite in a natural gas or coal or both kiln.

Note: Thermally decompose calcium sulfite using a hydrogen fuels system. If hydrogen is used for heat, there may be no $CO_2$ emissions in the end to end process. Also, green hydrogen can be produced from solar energy and stored, eliminating the challenge of solar intermittency. Alternatively or additionally, hydrogen may be blue hydrogen, or hydrogen from natural gas, where the carbon or $CO_2$ is removed from the natural gas to produce hydrogen before hydrogen is burned. Alternatively, a process may employ a combination of blue hydrogen (during the night) and solar electricity (during the day).

Note: Some embodiments may employ a hydrogen powered kiln. In some embodiments, the resulting water vapor may be condensed to form sulfurous acid. In some embodiments where combustion is employed to power the calcining and said combustion forms water, it may be desirable for a portion of said water to be condensed to form at least a portion of aqueous sulfur dioxide.

Note: 'Aqueous sulfur dioxide' and 'sulfurous acid' may be employed interchangeably Note: Recovery heat form hydrating calcium oxide to calcium hydroxide to provide heat or steam or both for applications requiring heat.

Note: Remaining flue gas after most or all SO2 is removed or recovered may comprise at least a portion CO2.

Note: Flue gas or CO2 from the flue gas may be employed as a CO2 input or CO2 source for a Solvay process to produce Sodium Bicarbonate or Sodium Carbonate. The Solvay process calcium oxide will be sourced from the present invention.

Note: Flue gas CO2 may be concentrated with pressure swing absorption or pressure swing adsorption or gas membrane or both, then the flue gas with higher concentrations of CO2 may be employed as a feedstock for the production of sodium bicarbonate or sodium carbonate.

Note: Convert calcium silicate from the Pidgeon process to calcium oxide or recovery calcium oxide from the Pidgeon process Note: a process for enabling full conversion of calcium carbonate or calcium silicate or a combination thereof to calcium oxide: CO2 production process from calcium carbonate, where the first step is to react Calcium Carbonate with equal to or less than stoichiometric amounts of sulfurous acid or with low vapor pressure sulfurous acid. The calcium sulfite solid is separated from this solution using solid-liquid separation. Then the resulting solid calcium sulfite (which may still comprise at least a portion calcium carbonate) is transferred to a step where it is dissolved in excess concentrated sulfurous acid, forming dissolve calcium bisulfate and CO2 from any unreacted calcium carbonate. Remaining CO2 is separated from the SO2 atmosphere by, for example, condensation of at least a portion of SO2 and/or a combination of other systems and/or methods. Any non-calcium sulfite or calcium carbonate (e.g. calcium sulfate or silica or other mostly insoluble chemicals) may remain as a solid and may be separated from the calcium bisulfite solution via liquid-solid separation.

Note: May employ calcium, or magnesium, or alkaline earth, or a combination thereof. Calcium or magnesium or alkaline earth may be substituted.

Note: In some embodiments, gas comprising sulfur dioxide may be compressed prior to or during absorption of sulfur dioxide in one or more or a combination of process steps described herein.

Note: In some embodiments, it may be desirable to avoid the formation of dissolved calcium bisulfite. In some embodiments, the formation of calcium bisulfite may be prevented by employing an organic solvent, or a non-water solvent, or both instead of or in addition to water as a solvent to absorb sulfur dioxide and/or react sulfur dioxide with calcium carbonate, or magnesium carbonate, or calcium silicate, or magnesium silicate, or a calcium-'WA' salt, or a magnesium-'WA' salt, or a combination thereof. The absence of water, or a lower concentration of water, or the presence of other solvents than water, or a combination thereof may inhibit the formation of dissolved calcium bisulfite in, for example, some embodiments where it is desired.

Note: 'WA' may comprise a weak acid. For example, 'WA' may comprise an acid with acidity less than or equal to sulfurous acid.

Note: A calcium silicate, or magnesium silicate, or both may comprise at least a portion calcium carbonate in some embodiments.

Note: One or more or a combination of reagents, or process steps, or a combination thereof may be heated, or cooled, or a combination thereof.

Note: Calcium silicate may comprise a material comprising silicate. A material comprising an impure limestone comprising at a portion a silicate material. For example, a material comprising silicate may comprise clay, or silicon dioxide, or alumino-silicate, or ferrite, or a combination thereof Note: Calcining of calcium sulfite may be conducted in the presence of clay, or silicon dioxide, or shale, or sand, or iron ore, or bauxite, or fly ash, and or slag or other materials employed to, for example, produce or facilitate the production of cement, or cement clinker, or a combination thereof Note: In some embodiments, it may be desirable to operate the calcination of calcium sulfite and/or cement manufacturing inputs in the presence of diatomic oxygen. For example, in some embodiments, diatomic oxygen present in a flue gas stream, or in hot gases entering or within a kiln, or a combination thereof may react or oxidize sulfur dioxide, or calcium sulfite, or derivatives thereof to form materials or chemicals which may be facilitate the manufacturing of cement or clinker or may enable advantageous properties in the cement or clinker. For example, in some embodiments, diatomic oxygen present in a flue gas stream, or in hot gases entering or within a kiln, or a combination thereof may react or oxidize sulfur dioxide, or calcium sulfite, or derivatives thereof to form calcium sulfate and/or derivatives thereof, which may be an advantageous ingredient or component of some cement or clinker compositions. For example, in some embodiments, diatomic oxygen present in a flue gas stream, or in hot gases entering or within a kiln, or a combination thereof may react or oxidize sulfur dioxide, or calcium sulfite, or derivatives thereof to form compounds or materials comprising sulfur with superior strength, or chemical resistance, or longevity, or pressure, or compressive strength, or water resistance, or temperature resilience, or other resilience, or cost, or adhesive properties, or chemical compatibility, or a combination thereof. For example, in some embodiments, diatomic oxygen present in a flue gas stream, or in hot gases entering or within a kiln, or a combination thereof may react with or oxidize sulfur dioxide, or calcium sulfite, or derivatives thereof to form compounds or materials with superior strength, or chemical resistance, or longevity, or pressure, or compressive strength, or water resistance, or temperature resilience, or other resilience, or cost, or adhesive properties, or chemical compatibility, or a combination thereof. For example, in some embodiments, diatomic oxygen present in a flue gas stream, or in hot gases entering or within a kiln, or a combination thereof may react with or oxidize sulfur dioxide, or calcium sulfite, or derivatives thereof to produce heat, which may reduce energy requirements or increase the energy efficiency of calcining.

Note: In some embodiments, the use of calcium sulfite as an input material for the production of cement may enable cement with superior properties, which may include, but are not limited to, superior strength, or chemical resistance, or longevity, or pressure, or compressive strength, or water resistance, or temperature resilience, or other resilience, or cost, or adhesive properties, or chemical compatibility, or a combination thereof.

Note: In some embodiments, calcium silicate may comprise cement manufacturing inputs. In some embodiments, cement manufacturing inputs may comprise calcium silicate. In some embodiments, cement manufacturing inputs may comprise calcium sulfite, or calcium oxide, or a combination thereof. In some embodiments, cement manufacturing inputs may comprise calcium bisulfite.

Note: Weak acids and weak acid anions may include, but are not limited to, one or more or a combination of the following: silicates, or carbonates, or aluminates, or aluminoferrites, or aluminum oxides, or zinc oxides, or iron oxides, or $Al_2O_6$, or $Al_2Fe_2O_{10}$.

Note: In some embodiments, at least a portion of the gases produced during or from the calcination of calcium sulfite may comprise water or water vapor. For example, if hydrogen, or natural gas, or ammonia, or a hydrocarbon, or other combustion, or steam, or a combination thereof is/are employed to provide heat for calcination, water vapor may be generated. In some embodiments, at least a portion of said gases produced during or from the calcination of calcium sulfite may be condensed to form an aqueous solution comprising aqueous sulfur dioxide or sulfurous acid. In some embodiments, said aqueous solution comprising aqueous sulfur dioxide or sulfurous acid may be employed as an aqueous sulfur dioxide solution or sulfurous acid solution in one or more process steps. In some embodiments, said aqueous solution comprising aqueous sulfur dioxide or sulfurous acid may undergo further concentrating, or diluting, or treating, or a combination thereof before being employed as an aqueous sulfur dioxide solution or sulfurous acid solution in one or more process steps.

Note: In some embodiments, nitrogen gas may be added to air before combustion with said air to reduce the concentration of oxygen before said air may be employed in the combustion of fuel for calcining calcium sulfite. For example, a nitrogen concentrating process may be employed. For example, an oxygen concentrating or oxygen removal process may be employed.

Note: In some embodiments, at least a portion of oxygen may be removed from air before combustion with said air to reduce the concentration of oxygen before said air may be employed in the combustion of fuel for calcining calcium sulfite. For example, a nitrogen concentrating process may be employed. For example, an oxygen concentrating or oxygen removal process may be employed.

Note: In some embodiments, a portion of gases after combustion and after sulfur dioxide removal may be added to air to reduce the concentration of diatomic oxygen before said air may be employed in the combustion of fuel for calcining calcium sulfite.

Note: In some embodiments, sulfur dioxide or carbon dioxide or both may be added to air to reduce the concentration of diatomic oxygen before said air may be employed in the combustion of fuel for calcining calcium sulfite.

Note: It may be desirable to calcine the calcium sulfite under conditions where the temperature is sufficiently low to prevent produced CaO crystallites from fusing. It may be desirable to calcine calcium sulfite under conditions and temperatures where the specific surface of the calcium oxide remains intact. It may be desirable to produce CaO with non-fused crystals, or where the specific surface of the calcium oxide remains intact, or a combination thereof for applications, which may include, but are not limited to, the steel industry.

Note: It may be desirable to calcine the calcium sulfite under conditions where the temperature is sufficiently high to facilitate the production of fused CaO crystallites. It may be desirable to calcine calcium sulfite under conditions and temperatures which reduce the specific surface of the calcium oxide. It may be desirable to produce CaO with fused crystals, or where the specific surface of the calcium oxide is reduced, or a combination thereof for applications, which may include, but are not limited to, the production of aerated concrete, or sand lime bricks, or a combination thereof.

Note: Heat sources may include, but are not limited to, one or more or a combination of the following: combustion of a fuel, hydrogen, ammonia, natural gas, heavy fuel oil, pulverised coal, liquefied gas, off-gas from steel-making process, wood dust, waste oil, biomass, biofuel, electricity, heat pump, solar thermal, chemical reaction, sulfur, sulfurous fuel, sulfuric acid production, salt production, waste heat, waste gases, nuclear heat, geothermal, quicklime, hydration reaction, oxidation.

Note: One or more of the present embodiments may produce strongly carbon dioxide negative or negative emissions calcium oxide Note: In some embodiments, produced calcium oxide may be reacted with carbon dioxide originating from the air or separated from the air. For example, calcium oxide may be reacted with sodium carbonate or potassium carbonate or sodium carbonate or potassium carbonate solution to produce sodium hydroxide or potassium hydroxide solution and calcium carbonate, which may be a permanent sequestration byproduct. Said sodium hydroxide or potassium hydroxide solution may then be contacted with air or $CO_2$ originating from air to produce a solution comprising sodium carbonate, or potassium carbonate, or a combination thereof Note: A portion of the calcium oxide produced may be converted to calcium carbonate by reaction, with, for example, carbon dioxide in the air, or carbon dioxide originating from the air, or an air capture process, or regenerating an alkali-carbonate to an alkali-oxide in an absorption loop, or regenerating an alkali-carbonate to an alkali-oxide in an absorption or separation process, or a combination thereof.

Note: A portion of the cement produced may be employed in the production of non-hydraulic cement, or cement employing at least a portion of $CO_2$ input, or a combination thereof to increase the net $CO_2$ removal or emissions reduction.

Note: Magnesium and calcium may be present in the same input material. For example, slags, or waste concrete, or minerals may comprise at least a portion of magnesium. For example, dolomite may comprise a portion of magnesium. In some embodiments, at least a portion of magnesium sulfite and/or magnesium oxide and/or magnesium hydroxide may be produced separately from calcium sulfite and/or calcium oxide and/or calcium hydroxide. For example, the separation of calcium and magnesium may be conducted by including, but not limited to, the significant difference in solubility in water between magnesium sulfite and calcium sulfite and/or the significant temperature dependent solubility of magnesium sulfite.

Note: The concentration of sulfur dioxide in aqueous sulfur dioxide may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: The concentration of sulfur dioxide gas in a gas comprising sulfur dioxide may be greater than or equal to one or more of the following volume percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: The concentration of magnesium oxide in the output comprising magnesium oxide may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: The concentration of calcium oxide in the output comprising magnesium oxide may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Additional Notes

Note: '$H_2SO_3(aq)$' or '$2\ SO_2(aq)+H_2O(l)$' may be employed interchangeably.

Note: The weight percent concentration of $SO_2$ in one or more aqueous sulfurous acid solutions or one or more solutions comprising sulfur dioxide may be greater than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Note: The volume percent concentration of $SO_2$ in one or more gases described herein may be greater than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Note: 'WA' may comprise a weak acid, which may include, but not limited to, silicic acid, or orthosilicic acid, or silicon acid derivatives, or silicon minerals, or silicon acids, or aluminates, or ferrates, or a combination thereof.

Note: Some embodiments may involve reacting calcium silicate or a material comprising silicon directly with sulfur dioxide or sulfur dioxide in an non-aqueous solution or a combination thereof.

Note: In some embodiments, contaminants or impurities may dissolve in a solution comprising sulfur dioxide, or due to the presence of sulfuric acid, or a combination thereof. Contaminants or impurities may include, but are not limited to, one or more or a combination of the following: iron, or aluminum, or alkali metals, or transition metals, or other non-bisulfite soluble salts, or non-alkaline earth bisulfite salts, or a combination thereof. In some embodiments, dissolved contaminants may be present after solid-liquid separation, and/or after calcium sulfite precipitation. In some embodiments, at least a portion of contaminants may be separated periodically or continuously. Contaminants may be separated by, including, but not limited to, precipitation, or membrane based process, or cooling, or heating, or crystallization, or cryodesalination, or a separation process described herein, or a separation process in the art, or a combination thereof Note: 'Calcium' may also refer to magnesium and/or other alkaline earth metals.

Note: In some embodiments, one absorption column, or absorption step, or absorption process, or a combination thereof may be employed to absorb sulfur dioxide gas and form aqueous sulfur dioxide or a sulfurous acid solution. In some embodiments, more than one absorption column, or absorption step, or absorption process, or a combination thereof may be employed to absorb sulfur dioxide gas and form aqueous sulfur dioxide or a sulfurous acid solution.

Note: Calcining kilns may include, but are not limited to, one or more or a combination of the following: Shaft kilns, or Counter-current shaft kilns, or Regenerative kilns, or Annular kilns, or Rotary kilns.

Additional Notes

Note: 'WA' may comprise a weak acid, which may include, but not limited to, silicic acid, or orthosilicic acid, or silicon acid derivatives, or silicon minerals, or silicon acids, or aluminates, or ferrates, or a combination thereof.

Note: Calcium or magnesium—weak acid input may comprise, for example, including, but not limited to, one or more or a combination of the following: carbonates, or bicarbonates, or silicates, or silicate derivatives, or minerals, or concrete, or cement, or waste concrete, or waste cement, or steel slag, or fly ash, or ash, or limestone, or rock.

Note: In some embodiments, higher partial pressure $CO_2$, or higher concentration $CO_2$, or pure $CO_2(g)$, or high partial pressure $CO_2(g)$, or $CO_2(l)$, or $CO_2(g)$, may be employed to facilitate formation of bicarbonate salts. For example, in some embodiments, one or more or a combination of the following may be employed:
 At least a portion of $CO_2$ input may be sourced from a reaction of calcium carbonate with sulfurous acid
 At least a portion of $CO_2$ input may be sources from $CO_2$ sources produced within the process, or other $CO_2$ sources, or a combination thereof
 At least a portion of $CO_2$ input may be sourced from $CO_2$ captured from a combustion source, or a combustion source employed to produce heat, or emissions source, or air, or geological $CO_2$ source, or natural $CO_2$ source, or a combination thereof.

Note: CO2 sources include, but are not limited to, those described herein.

Note: Some embodiments may be designed to operate as a low temperature process, where the solutions and/or solid reagents in thermal desorption or decomposition may undergo or operate thermal desorption or decomposition at less than 150° C., or less than 200° C., or less than 250° C., or less than 300° C., or less than 350° C.

Note: In some embodiments, at least a portion of heat may be supplied by a heat pump, or a refrigeration cycle, or a combination thereof. A heat pump may comprise, including, but not limited to, a mechanical, or thermal, or absorption, or a combination thereof process. A heat pump may be powered by, including, but not limited to, electricity, or heat, or photons, or chemical reaction, or radiation, or mechanical work, or pneumatic process, or hydraulic process, or expansion, or compression, or evaporation, or absorption, or vapor pressure differences, or osmotic pressure differences, or temperature differences, or pressure differences, or a combination thereof Note: In some embodiments, sulfides and/or hydrogen sulfide may comprise a weak acid or weak acid anion.

Note: Separations for removing accumulating water, or removing water, or recovering water, or concentrating, or crystalizing, or precipitating, or separating, or removing, or a combination thereof may include, but are not limited to, one or more or a combination of the following: falling film evaporator, mechanical vapor compression (MVC), or mechanical vapor recompression, or multi-effect distillation (MED), or multi-stage flash distillation (MSF), or vapor compression (VC) distillation, or vacuum vapor compression (VVC), or membrane distillation, or evaporation, or distillation, or forward osmosis, or reverse osmosis, or nanofiltration, or hot nanofiltration, or hot reverse osmosis, or hot concentrating followed by cooling precipitation, or hot concentrating followed by cooling precipitation and solid-liquid separation, or heating precipitation, centrifuge, settling, or filter, or rotary filter, or calcining, or desorption, or absorption, or coalescing, or decanting, or aggregation, or coagulation, or frothing, or density based methods, or surface tension based methods, or foaming separation, emulsification, or de-emulsification, or flocculation, solventing out, or salting out, or cooling precipitation, or heating, or cryodesalination, or zero liquid discharge processes, or crystallization processes, or electrodialysis reversal (EDR), or electrodialysis process, or magnetic separation, or eddy currents, or electromagnetic induction, or filtration, or activated carbon, or ion exchange, or ion exchange membrane, or precipitation process, or cryodesalination, or cooling desalination, or cooling, or heating, or salting-out, or solventing-out, or adding a solvent to precipitate a solid and then removing the added solvent, or a combination thereof.

Note: Some embodiments may employ an inert gas, such as nitrogen or argon, or a gas other than diatomic oxygen, such as $CO_2$, or a combination thereof in the headspace to prevent, for example, oxidation of or reaction of oxygen with sulfite, metabisulfite, bisulfite, sulfur dioxide, sulfurous acid, or a combination thereof Note: Magnesium or other alkaline earth or alkaline earth salts may be employed instead of or in addition to calcium.

Note: Concrete waste may be produced in excess of 600 million tons annually in the USA alone, which is more than twice the amount of generated municipal solid waste.

Note: At least a portion of sulfur dioxide may be lost in one or more or a combination of steps. Alternatively, or additionally, sulfur dioxide may be exit the process as a, for example, a residual, in one or more outputs. Sulfur dioxide or 'make-up sulfur dioxide' may be added to the process. In some embodiments, sulfur dioxide may be stored on site and added as desired or needed to the process. In some embodiments, elemental sulfur, or hydrogen sulfide, or a salt comprising sulfur, or sulfide salt, or sulfite salt, or sulfate salt, or a combination thereof may be a source of sulfur dioxide or sulfurous acid, by, for example, including, but not limited to, one or more or a combination thereof: combustion, or acid-base reaction, or reaction with an acid, or carbothermic reduction, or thermal or decomposition, or electrolysis, or electrodialysis, or electrochemical reaction.

Note: In some embodiments, at least a portion of calcium sulfate may be removed. For example, a portion of residual dissolved calcium sulfate may precipitate and may be removed by, for example, including, but not limited to, solid-liquid separation, or removal of calcium sulfate scaling, or a combination thereof Note: One or more or a combination of steps in one or more embodiments may require heating and/or cooling. For example, a reaction of sulfurous acid with a calcium-weak acid or magnesium-weak acid may require or may be facilitated by cooling or heating. Alternatively, or additionally, heat or heating or cooling or a combination thereof may be recovered from one or more or a combination of reaction steps. In some embodiments, heat or heating or cooling or a combination thereof may be recovered and said recovered heat or heating or cooling or a combination thereof may be transferred or employed in one or more other steps, or in the same step, or in other applications.

Note: Losses may occur during the process. Makeup streams of one or more or a combination of reagents may be added.

Note: Contaminants may exist or accumulate in the process. If desired, one or more contaminants may be at least partially removed periodically, or continuously, or as desired, or a combination thereof.

Note: Other acid gases may be employed instead of or in addition to sulfur dioxide, which may include, but are not limited to, nitrogen oxides, or nitrogen dioxide, or nitrogen monoxide, or dinitrogen tetroxide, or nitric acid, or carbon dioxide, or carbonic acid, or hydrogen sulfuric, or sulfonic acid, or hydrosulfuric acid, or organo-sulfurous compounds, or hydrochloric acid, or hydrobromic acid, or hydroiodic acid, or hydrogen cyanide, or sulfuric acid, or perchloric acid, or nitrous acid, or hydrofluoric acid, or nitrogen derivative acids, or halogen derivative acids, or derivatives thereof, or a combination thereof.

Note: At least a portion of heat may be provided from the reaction of calcium oxide with water to form calcium hydroxide or a calcium hydroxide solution.

Note: Calcium-weak acid or magnesium-weak acid salts or 'WA' may include, but are not limited, salts of organic acids. Organic acids, or carboxylic acids, or organic acid anions, or a combination thereof may include, but are not limited to, one or more or a combination of the following: citric acid, or aconitates, or citrates, or isocitrates, or alloisocitrate, or oxalic acid, or acetic acid, or carboxylic acids, or lactic acid, or aconitic acid, or formic acid, or uric acid, or malic acid, or tartaric acid, methanoic acid, or hydroxymethanoic acid, or ethanoic acid, or 2-hydroxyethanoic acid, or oxoethanoic acid, or ethanedioic acid, or propanoic acid, or propenoic acid, or propynoic acid, or 2-hydroxypropanoic acid, or 3-hydroxypropanoic acid, or 2,3-dihydroxypropanoic acid, or 2-oxopropanoic acid, or 3-oxopropanoic acid, or 2,3-dioxopropanoic acid, or propanedioic acid, or 2-hydroxypropanedioic acid, or 2,2-dihydroxypropanedioic acid, or oxopropanedioic acid, or oxirane-2-carboxylic acid, or butanoic acid, or 2-methylpropanoic acid, or (E)-but-2-enoic acid, or (Z)-but-2-enoic acid, or 2-methylpropenoic acid, or but-3-enoic acid, or but-2-ynoic acid, or 2-hydroxybutanoic acid, or 3-hydroxybutanoic acid, or 4-hydroxybutanoic acid, or 2-oxobutanoic acid, or 3-oxobutanoic acid, or 4-oxobutanoic acid, or butanedioic acid, or 2-methylpropanedioic acid, or (E)-butenedioic acid, or (Z)-butenedioic acid, or butynedioic acid, or hydroxybutanedioic acid, or 2,3-dihydroxybutanedioic acid, or oxobutanedioic acid, or dioxobutanedioic acid, or pentanoic acid, or 3-methylbutanoic acid, or 2-methylbutanoic acid, or 2,2-dimethylpropanoic acid, or 3-hydroxypentanoic acid, or 4-hydroxypentanoic acid, or 3-hydroxy-3-methylbutanoic acid, or pentanedioic acid, or 2-oxopentanedioic acid, or 3-oxopentanedioic acid, or furan-2-carboxylic acid, or tetrahydrofuran-2-carboxylic acid, or hexanoic acid, or hexanedioic acid, or 2,3-dimethylbutanoic acid, or 3,3-dimethylbutanoic acid, or 2-hydroxypropane-1,2,3-tricarboxylic acid, or prop-1-ene-1,2,3-tricarboxylic acid, or 1-hydroxypropane-1,2,3-tricarboxylic acid, or (2E,4E)-hexa-2,4-dienoic acid, or heptanoic acid, or heptanedioic acid, or cyclohexanecarboxylic acid, or benzenecarboxylic acid, or 2-hydroxybenzoic acid, or 4-carboxybenzoic acid, or 2,2-dimethylpentanoic acid, or 2,3-dimethylpentanoic acid, or 2,4-dimethylpentanoic acid, or 3,3-dimethylpentanoic acid, or 2-ethylpentanoic acid, or 3-ethylpentanoic acid, or 2-methylhexanoic acid, or 3-methylhexanoic acid, or 2,2,3-trimethylbutanoic acid, or 2-ethyl-2-methylbutanoic acid, or 2-ethyl-3-, or methylbutanoic acid, or octanoic acid, or benzene-1,2-dicarboxylic acid, or 2-methylheptanoic acid, or 3-methylheptanoic acid, or 4-methylheptanoic acid, or 5-methylheptanoic acid, or 6-methylheptanoic acid, or 2,2-dimethylhexanoic acid, or 2,3-dimethylhexanoic acid, or 2,4-dimethylhexanoic acid, or 2,5-dimethylhexanoic acid, or 3,3-dimethylhexanoic acid, or 3,4-dimethylhexanoic acid, or 3,5-dimethylhexanoic acid, or 4,4-dimethylhexanoic acid, or 4,5-dimethylhexanoic acid, or 5,5-dimethylhexanoic acid, or 2-ethanehexanoic acid, or 3-ethanehexanoic acid, or 4-ethanehexanoic acid, or 5-ethanehexanoic acid, or 2-octenoic acid, or 3-octenoic acid, or 4-octenoic acid, or 5-octenoic acid, or 6-octenoic acid, or 7-octenoic acid, or nonanoic acid, or benzene-1,3,5-tricarboxylic acid, or (E)-3-phenylprop-2-enoic acid, or decanoic acid, or decanedioic acid, or undecanoic acid, or dodecanoic acid, or benzene-1,2,3,4,5,6-hexacarboxylic acid, or tridecanoic acid, or tetradecanoic acid, or pentadecanoic acid, or hexadecanoic acid, or heptadecanoic acid, or octadecanoic acid, or (9Z)-octadec-9-enoic acid, or (9Z,12Z)-octadeca-9,12-dienoic acid, or (9Z,12Z,15Z)-octadeca-9,12,15-trienoic acid, or (6Z,9Z,12Z)-octadeca-6,9,12-trienoic acid, or (6Z,9Z,12Z,15Z)-octadeca-6,9,12,15-tetraenoic acid, or nonadecanoic acid, or eicosanoic acid, or (5Z,8Z,11Z)-eicosa-5,8,11-trienoic acid, or (5Z,8Z,11Z,14Z)-eicosa-5,8,11,14-tetraenoic acid, or (5Z,8Z,11Z,14Z,17Z)-eicosa-5,8,11,14-pentaenoic acid, or heneicosanoic acid, or docosanoic acid, or (4Z,7Z,10Z,13Z,16Z,19Z)-docosa-4,7,10,13,16,19-hexaenoic acid, or tricosanoic acid, or tetracosanoic acid, or pentacosanoic acid, or hexacosanoic acid, or amino acids, or glutamate, or glutamic acid.

Note: Weak acids or organic acids may include, but are not limited to, one or more or a combination of the following: carboxylic acids, or sulfonic acids, or alcohols, or thiols, or enols, or phenols, or carbonic acid Note: Calcium citrate may be in the form of tri-calcium citrate tetrahydrate.

Note: Separated citric acid may be in the form of an aqueous solution, or citric acid monohydrate, or anhydrous citric acid, or a combination thereof.

Note: Remaining solution after removal of citric acid may be treated with activated carbon, or passed through cation or anion exchangers, or an anion exchange resin, or a cation exchanger resin, or a combination thereof Note: Citric acid, or other carboxylic acid, or organic acid, or a combination thereof may be separated from or recovered from including, but not limited to, one or more or a combination of the following: fermentation broth, or sugar broths, or sugars, or raw sugars, or raw agricultural feedstocks, or agricultural byproducts, or sugar refining liquids, or mold produced citric acid, or juices, or fungi produced acids, or liquids or acids produced by *Aspergillus niger*, or sucrose broth, or dextrose broth, or glucose broth, or corn steep liquor, or molasses, or hydrolyzed corn starch, or citrus fruits, or fruit juices. Said separating or recovering may involve reaction or contacting with calcium hydroxide or aqueous calcium hydroxide solution.

Note: Heat may be recovered in one or more process steps and may employed in one or more other process steps, or within the same process step, or both.

Note: Calcium citrate may be provided as an example organic acid salt of calcium.

Note: Calcium may be provided as an example alkaline earth metal or alkaline earth metal cation or alkaline earth metal cation salt.

Note: Calcium silicate may be provided as an example weak acid salt of calcium or an example reagent representing a wide array of compositions or minerals comprising calcium, magnesium, silicon, oxygen, and derivatives thereof.

Note: Calcium oxide produced may be reacted with water to produce calcium hydroxide or a solution comprising aqueous calcium hydroxide. The aqueous calcium hydroxide may be reacted with $CO_2$, such as a gas comprising $CO_2$, to produce precipitate calcium carbonate and water. For example, aqueous sodium hydroxide may be reacted with flue gas, or raw gas, or air, or gases produced from fuel combusted to power the calciner, or remaining gases after absorption of sulfur dioxide, or other gas comprising at least a portion $CO_2$, or a combination thereof. Some embodiments of the present invention may be employed to produce $CO_2$-emissions neutral or negative precipitated calcium carbonate. Some embodiments of the present invention may involve producing $CO_2$-emissions neutral or negative precipitated calcium carbonate using $CO_2$ from the air or captured from the air using the presently described process.

Note: Calcium oxide produced may be reacted with water to produce calcium hydroxide or a solution comprising aqueous calcium hydroxide. The aqueous calcium hydroxide may be reacted sodium carbonate, such as an aqueous solution of sodium carbonate, to produce precipitate calcium carbonate and aqueous sodium hydroxide. The precipitated calcium carbonate may be separated from the aqueous sodium hydroxide and may comprise a valuable byproduct. The aqueous sodium hydroxide may be reacted with a gas comprising carbon dioxide to produce aqueous sodium carbonate. For example, aqueous sodium hydroxide may be reacted with flue gas, or raw gas, or air, or gases produced from fuel combusted to power the calciner, or remaining gases after absorption of sulfur dioxide, or other gas comprising at least a portion $CO_2$, or a combination thereof. Some embodiments of the present invention may be employed to produce $CO_2$-emissions neutral or negative precipitated calcium carbonate. Some embodiments of the present invention may involve producing $CO_2$-emissions neutral or negative precipitated calcium carbonate using $CO_2$ from the air or captured from the air using the presently described process. Some embodiments of the present invention may involve producing $CO_2$-emissions neutral or negative precipitated calcium carbonate using $CO_2$ from emissions sources, or air, or both using the presently described process.

Note: The weight percent concentration of one or more or a combination of reagents may include, but is not limited to, less than, or equal to, or greater than one or more or a combination of the following: 0%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: Calcium silicate input or magnesium silicate input may comprise a slag. For example, global iron slag production is estimated to be 320 million to 384 million tons annually and steel stag is estimated to be between 190 million to 280 million tons annually. Other slags may include, but are not limited to, slags from magnesium production. Slags are generally produced when calcium oxide or magnesium oxide are added to a metal production process to remove impurities, or facilitate certain conditions or properties, or a combination thereof. The present invention may convert said slags into calcium oxide or magnesium oxide or other alkaline earth oxide. The present invention may enable a circular economy in the iron-marking, or steel-making, or other metal production industries because calcium oxide and/or magnesium oxide are used as the inputs which result in the production of slag. If iron or steel makers can recycle at least a portion of slag into calcium oxide or magnesium oxide, iron or steel makers may greatly reduce or eliminate their need to purchase calcium oxide or magnesium oxide, significantly reducing operating costs. If at least a portion of iron or steel stag is recycled into calcium oxide or magnesium oxide, iron and/or steel production lifecycle carbon dioxide emissions will be greatly reduced.

Note: Calcium sulfite and/or magnesium sulfite may comprise hydrates. For example, magnesium sulfite may form a hexahydrate, or a trihydrate, or may be anhydrous. For example, calcium sulfite may form a tetrahydrate, or a hemihydrate, or may be anhydrous. It may be desirable to dehydrate at least a portion of the hydrate of calcium sulfite, or magnesium sulfite, or both before or during calcining of a sulfite into an oxide and sulfur dioxide. It may be desirable to dehydrate at least a portion of the hydrate of calcium sulfite, or magnesium sulfite, or both before calcining of a sulfite into an oxide and sulfur dioxide. For example, magnesium sulfite hexahydrate may be heated to above 40° C., where magnesium sulfite hexahydrate may decompose or dehydrate into magnesium sulfite trihydrate. For example, calcium sulfite tetrahydrate may be heated to decompose or dehydrate into calcium sulfite hemihydrate. For example, calcium and/or magnesium hydrates may be decomposed or dehydrated into anhydrous forms. For example, calcium sulfite hydrate and/or magnesium sulfite hydrate may be heated to decompose or dehydrate into anhydrous forms. Dehydrating hydrates may require heat or other energy. It may be desirable to supply said heat or other energy for dehydrating hydrates from lower cost, or lower quality heat sources, such as, including, but not limited to, one or more or a combination of the following: waste heat, or heat from other process steps, or low quality steam, or medium quality steam, or high quality step, or combustion of one or more fuels, or or solar thermal, or slacking lime, or hydrating a oxide to a hydroxide, or other heat source.

Note: Systems and methods may be employed to remove impurities, or prevent or minimize accumulation of impurities, or a combination thereof. For example, input materials may comprise impurities other than desired reagents. In some instances, said impurities or contaminants may accumulate, or may result in the formation of other impurities, or a combination thereof. In some instances, impurities may dissolve in one or more solutions in the process. Impurities may be removed, or treated, or separated, by, including, but not limited to, one or more or a combination of the following: chemical reaction, or electrodialysis, or ion-exchanger, or precipitation, or cooling, or heating, or distillation, or membrane-based process, or solventing-out, or salting out.

Note: At least a portion of the weak acid product, or undissolved materials, or a combination thereof are employed as a concrete aggregate.

Note: At least a portion of the weak acid product, or undissolved materials, or a combination thereof may be disposed of or may comprise a waste product.

Note: A material comprising calcium and/or magnesium may comprise a material comprising an alkaline-earth. Alkaline-earths may include one or more or a combination of the following: beryllium (Be), or magnesium (Mg), or calcium (Ca), or strontium (Sr), or barium (Ba), or radium (Ra)

Note: In some embodiments, a material comprising calcium and/or magnesium may further comprise one or more or a combination of the following: iron oxides, or iron, or manganese oxide, or manganese, may include, but are not limited to, one or more or a combination of the following: iron (II), or iron (II,III), or iron (III), or iron (II) oxide, or iron (II,II) oxide, or iron (III) oxide, or iron sulfite, or iron sulfate, or iron sulfide, or iron, or ferrites, or ferrates, or calcium-iron salts, or magnesium iron salts, or iron silicate salts, or iron silicon salts, or iron carbon salts, or manganese salts, or manganese −3, or manganese −2, or manganese −1, or manganese 0, or manganese +1, or manganese +2, or manganese, or manganese +3, or manganese +4, or manganese +5, or manganese +6, or manganese +7, or manganese sulfite, or manganese oxide, or manganese carbonate, or manganese-iron, or calcium-manganese, or calcium-manganese salts, or magnesium manganese, or magnesium-manganese salts, or manganese silicon, or manganese carbon, or manganese Note: The properties of iron and manganese may be similar. Manganese may be present in some materials which may comprise iron, such as some slags, or concretes, or minerals. In some embodiments, iron and manganese may be used interchangeably.

Note: Solutions comprising salts of metals lead, or copper, or gold, or silver, or zinc, or aluminum, or chromium, or cobalt, or manganese, or rare-earth metals, or iron, or molybdenum, or cadmium, or nickel, or silver, or cobalt, or zinc, or gold, or platinum, or platinum group metals, or a combination thereof may undergo a separations and/or refining process. For example, one or more or a combination of said metals may be separated or produced from solution or from a separated state or both by means of, for example, including, but not limited to, one or more or a combination of the following: electrolytic refining, or electrowinning, or electroextraction, or electrodeposition. For example, a solution comprising aqueous iron bisulfite, or manganese bisulfite, or iron sulfate, or manganese bisulfate, or iron chloride, or magnesium chloride may undergo electroextraction to produce manganese, iron, or a combination thereof. In some embodiments, one or more or a combination of the aforementioned metals may be separated by reaction with hydrogen sulfide or sulfur to produce a sulfide or an insoluble sulfide, then said sulfide may be converted into a form for use as in input to an electroextraction process.

Note: Separation of at least a portion of iron sulfite solid from at least a portion of calcium sulfite solid, or separation of iron from calcium or magnesium, or a combination thereof may be conducted by, including, but not limited to, one or more or a combination of the following: density based separation, or floatation and sinking separation using a dense liquid, or separation using a dense liquid, or separation using a liquid with a lower density than iron sulfite and a greater density than calcium sulfite, or magnetic separation, or magnetic separation of iron from calcium, or oxidation of iron, or reaction of solution comprising dissolved iron with hydrogen sulfide to produce iron sulfide solid precipitate, or reaction of solution comprising calcium with sulfuric acid to form calcium sulfate precipitate, or frothing, or floatation, or solid separation, or centrifuge, or grinding, or pulverization, or reaction of iron sulfite and calcium sulfite solids with sulfuric acid to form dissolved or aqueous iron sulfate and calcium sulfate solid, or reaction of a mixture of calcium oxide and iron oxide with water to form calcium hydroxide dissolved or aqueous and iron oxide solid, or precipitation of iron sulfite before calcium sulfite, or precipitation of calcium sulfite before iron sulfite, or electrodialysis, or electrodialysis reversal, or ion exchange, or iron exchange resin, or iron reaction, or double-salt reaction, or precipitation reaction, or temperature driven precipitation, or concentration driven precipitation Note: Oxygen or 'oxide' or 'hydroxide' or a combination thereof may be considered weak acids or 'weak acid anions' or a combination thereof.

Note: Desorption of sulfur dioxide form a solution comprising bisulfite may be conducted by, for example, including, but not limited to, one or more or a combination of the following: thermal desorption, or steam stripping, or a combination thereof. A solution comprising bisulfite may include, but is not limited to, a solution comprising one or more or a combination of the following: alkaline earth bisulfite, or magnesium bisulfite, or calcium bisulfite, or iron bisulfite, or manganese bisulfite, or zinc bisulfite, or sulfur dioxide, or water, or sulfurous acid.

Note: Separations may include, but are not limited to, one or more or a combination of the following: Separation by density, or Separation by magnetism, or Separation by frothing or surface tension, or Separation by residual solubility differences, or Separation by oxidation, or Separation by ion exchange, or Separation by reaction with an alkali hydroxide solution, or Separation by reaction with hydrogen sulfide, or Separation by reaction with aqueous sulfuric acid, or Separation by density using a high density liquid with a density less than at least one salt and a density greater than one salt, or Separation by density using a high density liquid with a density less than iron sulfite and a density greater than calcium sulfite, or Separation by density using a centrifuge, or Separation by a magnetic field using a mixing and an externally applied magnetic field, or Separation by reaction with and/or dissolution in water, or Grinding or pulverization, or Separation by froth flotation, or Other solid-solid separation method, or Other method for separating iron from calcium, or Other separation method Note: In some embodiments, remaining solution after separating magnesium sulfite solid using a solid-liquid separate process may be further treated with, including, but not limited to, one or more or a combination of the following: ion exchange, or resins, or filters, or chemical treatments, or chemical reactions, or membrane based process, or distillation, or cooling, or heating, or freezing, or crydesalination, or solventing-out, or solvent induced precipitation, or salting-out, or other treatment. One or more solutions comprising water may be transferred to a sulfur dioxide absorption step, or mixed with a solution transferred to a sulfur dioxide absorption step, or a combination thereof.

EMBODIMENTS

Metal Oxide Embodiments

1. A process for producing calcium oxide, magnesium oxide, or both from a material comprising calcium and magnesium wherein the process comprises:
   reacting a material comprising calcium carbonate and magnesium carbonate with a solution comprising aqueous sulfur dioxide to form a gas comprising $CO_2$, a liquid solution comprising aqueous magnesium sulfite, and a solid comprising calcium sulfite;
   separating said solid comprising calcium sulfite from said liquid solution comprising aqueous magnesium sulfite;
   concentrating said aqueous magnesium sulfite using a membrane based process to form a concentrate solution comprising magnesium sulfite and a permeate comprising water;
   precipitating solid magnesium sulfite from said concentrate solution comprising aqueous magnesium sulfite; and
   calcining said solid calcium sulfite to produce calcium oxide or cement or calcining said solid magnesium sulfite to produce magnesium oxide or cement.
2. The process of embodiment 1 wherein said membrane based process comprises reverse osmosis, or forward osmosis, or both.
3. The process of embodiment wherein said concentrating is conducted at a temperature greater than about 35° C. and less than about 100° C.
4. The process of embodiment wherein said precipitating comprises cooling said concentrate solution to a temperature of less than about 35° C.
5. The process of embodiment 1 which further comprises drying before calcining.
6. The process of embodiment 5 wherein said drying is at least partially conducted at a temperature less than a temperature of calcining.
7. The process of embodiment 5 wherein at least a portion of heat for said drying is supplied by reacting calcium oxide with water, or reacting magnesium oxide with water, or both.
8. The process of embodiment 5 wherein a carrier gas comprising water vapor is employed during drying and wherein the process further comprising removing at least a portion of water vapor from said carrier gas.
9. The process of embodiment 8 wherein the removing comprises reacting the water vapor with calcium oxide to form calcium hydroxide.
10. The process of embodiment 8 wherein the removing comprises reacting the water vapor with a non-regenerated desiccant.
11. The process of embodiment 8 wherein the removing comprises employing a liquid desiccant, or a solid desiccant, or both.
12. The process of embodiment 8 wherein the removing comprises employing a membrane-based process.
13. The process of embodiment 8 wherein the removing comprises condensing.
14. The process of embodiment 8 wherein said carrier gas comprises less than about 2 percent by volume of diatomic oxygen.
14. The process of embodiment 1 wherein the concentration of $CO_2$ in the gas comprising $CO_2$ is greater than about 95 volume percent.
15. The process of embodiment 1 wherein the partial pressure of $CO_2$ in the gas comprising $CO_2$ is greater than about 1.5 atm.
16. The process of embodiment 1 wherein the calcining of calcium sulfite to calcium oxide, or the calcining of magnesium sulfite to magnesium oxide, or both further comprises forming a gas comprising sulfur dioxide.
17. The process of embodiment 16 further comprising absorbing at least a portion of said gas comprising sulfur dioxide into a solution comprising water to form aqueous sulfur dioxide.
18. The process of embodiment 17 wherein at least a portion of said solution comprising water comprises the permeate comprising water.
19. The process of embodiment 1 further comprising employing an ant-scaling chemical.
20. The process of embodiment 1 which further comprises heating a remaining solution after precipitating magnesium sulfite mixed said remaining solution with said aqueous magnesium sulfite before or during concentrating by the membrane based process.
21. The process of embodiment 1 which further comprises removing at least a portion of non-magnesium sulfite impurities from a remaining solution after precipitating magnesium sulfite.
22. The process of embodiment 22 which further comprises heating and mixing the solution with at least a portion of impurities removed with the aqueous magnesium sulfite before or during concentrating by the membrane based process.
23. The process of embodiment 1 which further comprising employing a remaining solution after precipitating magnesium sulfite to absorb at least a portion of any sulfur dioxide produced calcining of calcium sulfite or calcining of magnesium sulfite.
24. The process of embodiment 1 which further comprises recovering at least a portion of any sulfur dioxide produced by calcining of calcium sulfite or calcining of magnesium sulfite by cryogenic separation.

25. The process of embodiment 1 which further comprises distilling at least a portion of a remaining solution after precipitating magnesium sulfite.

26. A process for producing calcium oxide, magnesium oxide, or both from a material comprising calcium and magnesium comprising:
reacting a material comprising calcium and magnesium with sulfur dioxide to form a solid comprising calcium sulfite and magnesium sulfite;
contacting said solid comprising calcium sulfite and magnesium sulfite with water to form a liquid solution comprising aqueous magnesium sulfite; and
separating said solid comprising calcium sulfite from said liquid solution comprising aqueous magnesium sulfite.

27. The process of embodiment 26 further comprising concentrating said aqueous magnesium sulfite using a membrane based process to form a concentrate solution comprising magnesium sulfite and a permeate comprising water.

28. The process of embodiment 26 further comprising precipitating solid magnesium sulfite from said concentrate solution comprising aqueous magnesium sulfite.

29. The process of embodiment 26 further comprising drying said precipitated solid magnesium sulfite using a carrier gas with a diatomic oxygen concentration of less than about 3 volume percent.

30. A process for producing magnesium oxide from a material comprising calcium and magnesium comprising:
reacting a material comprising calcium and magnesium with a solution comprising aqueous sulfur dioxide to form a liquid solution comprising aqueous magnesium sulfite, and a solid comprising calcium sulfite;
separating said solid comprising calcium sulfite from said liquid solution comprising aqueous magnesium sulfite;
concentrating said aqueous magnesium sulfite using a membrane-based process to form a concentrate solution comprising magnesium sulfite;
precipitating solid magnesium sulfite from said concentrate solution comprising aqueous magnesium sulfite; and
calcining said solid magnesium sulfite to produce magnesium oxide.

Citric Acid Embodiments

1. A process for producing an alkaline-earth oxide and a carboxylic acid from an alkaline earth cation-carboxylic acid anion salt wherein the process comprises:
reacting an alkaline-earth cation-carboxylic acid anion salt with aqueous sulfur dioxide to produce aqueous alkaline-earth-bisulfite and aqueous carboxylic acid solution;
desorbing sulfur dioxide from said aqueous alkaline-earth-bisulfite and aqueous carboxylic acid solution to produce alkaline-earth-sulfite solid and aqueous carboxylic acid solution;
separating said alkaline-earth-sulfite solid from said aqueous carboxylic acid solution; and
calcining said alkaline-earth-sulfite solid to produce alkaline-earth-oxide, cement, or a combination thereof.

2. The process of embodiment 1 wherein said alkaline-earth cation comprises calcium cation.

3. The process of embodiment 1 wherein said alkaline-earth cation comprises magnesium cation.

4. The process of embodiment 1 wherein said carboxylic acid anion salt comprises citric acid anion salt.

5. The process of embodiment 1 which further comprises separating aqueous carboxylic acid solution into isolated carboxylic acid and water.

6. The process of embodiment 5 which further comprises absorbing sulfur dioxide with said water to generate aqueous sulfur dioxide for the reacting step.

7. The process of embodiment 1 which further comprises absorbing said desorbed sulfur dioxide in water to produce aqueous sulfur dioxide.

8. The process of embodiment 1 wherein said calcining said alkaline-earth-sulfite solid produces sulfur dioxide.

9. The process of embodiment 8 which further comprises absorbing said sulfur dioxide in water to produce aqueous sulfur dioxide.

10. The process of embodiment 1 which further comprises reacting said alkaline-earth-oxide with water to produce alkaline-earth-hydroxide.

11. The process of embodiment 10 wherein said reacting produces heat and wherein said heat is used in the process.

12. The process of embodiment 10 which further comprises reacting said alkaline-earth-hydroxide with a solution comprising a carboxylic acid to form alkaline-earth cation-carboxylic acid anion salt.

13. The process of embodiment 12 wherein at least a portion of said alkaline-earth cation-carboxylic acid anion salt is a solid.

14. The process of embodiment 13 which further comprises separating said alkaline-earth cation-carboxylic acid anion salt using solid-liquid separation.

15. The process of embodiment 1 wherein said separating comprises a solid-liquid separation step.

16. The process of embodiment 1 wherein the process is conducted in the presence of a low diatomic oxygen environment.

17. The process of embodiment 1 wherein said calcining is conducted under conditions to substantially prevent the formation of sulfate.

18. The process of embodiment 1 which further comprises producing a precipitated alkaline-earth-carbonate from said alkaline-earth-hydroxide.

19. The process of embodiment 18 wherein said precipitated alkaline-earth-carbonate comprises calcium carbonate, magnesium carbonate, or both.

20. The process of embodiment 10 wherein said alkaline-earth-hydroxide is dissolved in water.

21. The process of embodiment 12 wherein said alkaline-earth-hydroxide is dissolved in water.

21. The process of embodiment 12 wherein said alkaline-earth-hydroxide comprises calcium hydroxide.

22. The process of embodiment 5 wherein said isolated water comprises dissolved sulfur dioxide.

23. The process of embodiment 22 which further comprises separating sulfur dioxide from the isolated water.

24. The process of embodiment 10 wherein said reacting produces heat and wherein said heat is used desorb sulfur dioxide, separate water, or both.

25. A process for producing calcium oxide and carboxylic acid from a calcium cation-carboxylic acid anion salt wherein the process comprises:
reacting a calcium cation-carboxylic acid anion salt with aqueous sulfur dioxide to produce aqueous calcium bisulfite and aqueous carboxylic acid;
desorbing sulfur dioxide from said aqueous calcium bisulfite and aqueous carboxylic acid solution to produce calcium sulfite solid and aqueous carboxylic acid solution;

separating said calcium sulfite solid from said aqueous carboxylic acid solution; and calcining said calcium sulfite solid to produce calcium oxide, cement, or a combination thereof.

26. A process for producing calcium oxide and citric acid from calcium citrate wherein the process comprises:

reacting calcium citrate with aqueous sulfur dioxide to produce aqueous calcium bisulfite and aqueous citric acid;

desorbing sulfur dioxide from said aqueous calcium bisulfite and aqueous citric acid solution to produce calcium sulfite solid and aqueous citric acid solution;

separating said calcium sulfite solid from said aqueous citric acid solution; and calcining said calcium sulfite solid to produce calcium oxide, cement, or a combination thereof.

The invention claimed is:

1. A process for producing an alkaline-earth oxide and a carboxylic acid from an alkaline earth cation-carboxylic acid anion salt wherein the process comprises:

reacting an alkaline-earth cation-carboxylic acid anion salt with aqueous sulfur dioxide to produce aqueous alkaline-earth-bisulfite and aqueous carboxylic acid solution;

desorbing sulfur dioxide from said aqueous alkaline-earth-bisulfite and aqueous carboxylic acid solution to produce alkaline-earth-sulfite solid and aqueous carboxylic acid solution;

separating said alkaline-earth-sulfite solid from said aqueous carboxylic acid solution; and calcining said alkaline-earth-sulfite solid to produce alkaline-earth-oxide, cement, or a combination thereof.

2. The process of claim 1 wherein said alkaline-earth cation comprises calcium cation.

3. The process of claim 1 wherein said alkaline-earth cation comprises magnesium cation.

4. The process of claim 1 wherein said carboxylic acid anion salt comprises citric acid anion salt.

5. The process of claim 1 which further comprises separating aqueous carboxylic acid solution into isolated carboxylic acid and water.

6. The process of claim 5 which further comprises absorbing sulfur dioxide with said water to generate aqueous sulfur dioxide for the reacting step.

7. The process of claim 5 wherein said isolated water comprises dissolved sulfur dioxide.

8. The process of claim 7 which further comprises separating sulfur dioxide from the isolated water.

9. The process of claim 1 which further comprises absorbing said desorbed sulfur dioxide in water to produce aqueous sulfur dioxide.

10. The process of claim 1 wherein said calcining said alkaline-earth-sulfite solid produces sulfur dioxide.

11. The process of claim 10 which further comprises absorbing said sulfur dioxide in water to produce aqueous sulfur dioxide.

12. The process of claim 1 which further comprises reacting said alkaline-earth-oxide with water to produce alkaline-earth-hydroxide.

13. The process of claim 12 wherein said alkaline-earth-hydroxide is dissolved in water.

14. The process of claim 12 wherein said reacting produces heat and wherein said heat is used desorb sulfur dioxide, separate water, or both.

15. The process of claim 12 wherein said reacting produces heat and wherein said heat is used in the process.

16. The process of claim 12 which further comprises reacting said alkaline-earth-hydroxide with a solution comprising a carboxylic acid to form alkaline-earth cation-carboxylic acid anion salt.

17. The process of claim 16 wherein said alkaline-earth-hydroxide is dissolved in water.

18. The process of claim 16 wherein said alkaline-earth-hydroxide comprises calcium hydroxide.

19. The process of claim 16 wherein at least a portion of said alkaline-earth cation-carboxylic acid anion salt is a solid.

20. The process of claim 19 which further comprises separating said alkaline-earth cation-carboxylic acid anion salt using solid-liquid separation.

21. The process of claim 1 wherein said separating comprises a solid-liquid separation step.

22. The process of claim 1 wherein the process is conducted in the presence of a low diatomic oxygen environment.

23. The process of claim 1 wherein said calcining is conducted under conditions to substantially prevent the formation of sulfate.

24. The process of claim 1 which further comprises producing a precipitated alkaline-earth-carbonate from said alkaline-earth-hydroxide.

25. The process of claim 24 wherein said precipitated alkaline-earth-carbonate comprises calcium carbonate, magnesium carbonate, or both.

26. A process for producing calcium oxide and carboxylic acid from a calcium cation-carboxylic acid anion salt wherein the process comprises:

reacting a calcium cation-carboxylic acid anion salt with aqueous sulfur dioxide to produce aqueous calcium bisulfite and aqueous carboxylic acid;

desorbing sulfur dioxide from said aqueous calcium bisulfite and aqueous carboxylic acid solution to produce calcium sulfite solid and aqueous carboxylic acid solution;

separating said calcium sulfite solid from said aqueous carboxylic acid solution; and calcining said calcium sulfite solid to produce calcium oxide, cement, or a combination thereof.

27. A process for producing calcium oxide and citric acid from calcium citrate wherein the process comprises:

reacting calcium citrate with aqueous sulfur dioxide to produce aqueous calcium bisulfite and aqueous citric acid;

desorbing sulfur dioxide from said aqueous calcium bisulfite and aqueous citric acid solution to produce calcium sulfite solid and aqueous citric acid solution;

separating said calcium sulfite solid from said aqueous citric acid solution; and calcining said calcium sulfite solid to produce calcium oxide, cement, or a combination thereof.

* * * * *